US007820180B2

(12) United States Patent
Singh et al.

(10) Patent No.: US 7,820,180 B2
(45) Date of Patent: *Oct. 26, 2010

(54) LISTERIA-BASED AND LLO-BASED VACCINES

(75) Inventors: Reshma Singh, Philadelphia, PA (US); Yvonne Paterson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/223,945

(22) Filed: Sep. 13, 2005

(65) Prior Publication Data

US 2006/0093582 A1    May 4, 2006

Related U.S. Application Data

(63) Continuation-in-part of application No. 10/949,667, filed on Sep. 24, 2004.

(51) Int. Cl.
*A61K 39/02* (2006.01)
*A61K 38/04* (2006.01)
*A61K 38/16* (2006.01)

(52) U.S. Cl. .................. 424/200.1; 424/93.1; 424/93.2; 424/93.21; 424/184.1; 424/190.1; 424/192.1; 424/207.1; 424/210.1; 424/234.1; 424/237.1

(58) Field of Classification Search ................ 424/93.1, 424/93.2, 93.21, 93.4, 184.1, 190.1, 192.1, 424/193.1, 200.1, 207.1, 210.1, 234.1, 237.1
See application file for complete search history.

(56) References Cited

U.S. PATENT DOCUMENTS

| | | | |
|---|---|---|---|
| 4,458,066 A | 7/1984 | Caruthers et al. | |
| 4,521,382 A | 6/1985 | Kessick | |
| 4,777,239 A | 10/1988 | Schoolnik et al. | |
| 4,816,253 A | 3/1989 | Likhite et al. | |
| 5,262,177 A | 11/1993 | Brown et al. | |
| 5,342,774 A | 8/1994 | Boon et al. | |
| 5,681,570 A | 10/1997 | Yang et al. | |
| 5,824,538 A | 10/1998 | Branstrom et al. | |
| 5,830,702 A | 11/1998 | Portnoy et al. | |
| 5,858,682 A | 1/1999 | Gruenwald et al. | |
| 5,877,159 A | 3/1999 | Powell et al. | |
| 6,015,567 A * | 1/2000 | Hudziak et al. | 424/277.1 |
| 6,017,705 A | 1/2000 | Lurquin et al. | |
| 6,051,237 A | 4/2000 | Paterson | |
| 6,099,848 A | 8/2000 | Frankel et al. | |
| 6,306,404 B1 | 10/2001 | LaPosta et al. | |
| 6,479,258 B1 | 11/2002 | Short | |
| 6,521,449 B1 | 2/2003 | Polack et al. | |
| 6,565,852 B1 * | 5/2003 | Paterson | 424/200.1 |
| 6,740,516 B2 | 5/2004 | Savitzky et al. | |
| 6,767,542 B2 | 7/2004 | Paterson et al. | |
| 7,588,930 B2 | 6/2005 | Paterson et al. | |
| 7,135,188 B2 * | 11/2006 | Paterson | 424/277.1 |
| 2003/0028206 A1 | 2/2003 | Shiber | |
| 2003/0202985 A1 | 10/2003 | Paterson | |
| 2003/0220239 A1 | 11/2003 | Simard et al. | |
| 2004/0228877 A1 | 11/2004 | Dubensky et al. | |
| 2005/0118184 A1 | 6/2005 | Paterson et al. | |
| 2005/0129715 A1 | 6/2005 | Paterson et al. | |
| 2006/0051380 A1 | 3/2006 | Schulick et al. | |
| 2006/0093582 A1 | 5/2006 | Paterson et al. | |
| 2006/0104991 A1 | 5/2006 | Paterson et al. | |
| 2006/0121053 A1 | 6/2006 | Sweeney et al. | |
| 2006/0205067 A1 | 9/2006 | Paterson et al. | |
| 2006/0210540 A1 | 9/2006 | Paterson et al. | |
| 2006/0233835 A1 | 10/2006 | Paterson et al. | |

FOREIGN PATENT DOCUMENTS

| | | |
|---|---|---|
| EP | 0 902 086 | 3/1999 |
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 98/48026 | 10/1998 |
| WO | WO 99/06544 | 2/1999 |

(Continued)

OTHER PUBLICATIONS

Renard, V. et al. The Journal of Immunology, 171: 1588-1595, 2003.*
Paterson, Y., Immunologic Research, 27(2-3): 451-462, 2003, June.*
Beatly, Dissertation Abstracts Interntational, 2000, 61/10B:5224 Abstract Only.
Burnham, Drug Discovery Today, Jan. 2003, 8/2:54-55.
Gunn et al, J. Immunology, 2001, 167: 6471-6479.

(Continued)

*Primary Examiner*—Alana M. Harris
*Assistant Examiner*—Anne L Holleran
(74) *Attorney, Agent, or Firm*—Mark S. Cohen; Pearl Cohen Zedek Latzer, LLP

(57) ABSTRACT

This invention provides methods of treating and vaccinating against an antigen-expressing tumor and inducing an immune response against a sub-dominant epitope of antigen, comprising a fusion of an LLO fragment to the antigen or a recombinant *Listeria* strain expressing the antigen. The present invention also provides recombinant peptides comprising a listeriolysin (LLO) protein fragment fused to a Her-2 protein or fragment thereof, recombinant *Listeria* strains expressing a Her-2 protein, vaccines and immunogenic compositions comprising same, and methods of inducing an anti-Her-2 immune response and treating and vaccinating against a Her-2-expressing tumor, comprising same.

62 Claims, 12 Drawing Sheets

FOREIGN PATENT DOCUMENTS

| | | |
|---|---|---|
| WO | WO 99/07861 | 2/1999 |
| WO | WO 99/10496 | 3/1999 |
| WO | WO 01/27295 | 3/2001 |
| WO | WO 01/72329 | 10/2001 |
| WO | WO 03/092600 | 11/2003 |
| WO | WO 2004/006837 | 1/2004 |

OTHER PUBLICATIONS

Gunn, Dissertaiton Abstracts International, 2001, 62/5B:2244 Abstract Only.
Harty, et al, Current Opinion in Immunology, 1996, 8: 526-530.
Hu, et al, J. Immunology, 172: 1595-1601, 2004.
Kerksiek, et al, Current Opinion in Immunology, 1999. 11:40-405.
Lara-Tejero, et al, Current Opinion in Immunology, 2004, 7: 45-50.
Mandal, et al, BBA, 2002, 1563: 7-17.
Paterson, et al, Current Opinion in Immunology, 1996, 8:664-669.
Shen, et al, Current Opinion in Immunology, 1998, 10: 450-458.
Gunn, et al, TRENDS in Microbiology, Apr. 2001, 9/4: 161-162.
Ikonomidis, et al, J. Exp. Med., Dec. 1994, 180: 2209-2218.
Lamikanra, et al, J. Virology, Oct. 2001, 75/20:9654-9664.
Pan, et al, Cancer Research, 1999, 59: 5264-5269.
Peng, et al, J. Immunology, 2004, 172: 6030-6038.
Radford, et al, Gene Therapy, 2002, 9: 1455-1463.
Radford, et al, Int. J. Cancer, 2003, 105: 811-819.
Barry, et al (1992) "Pathogenicity and immunogenicity of Listeria monocytogenes small-plaque mutants defective for intracellular growth and cell-to-cell spread." Infection and Immunity 60 (4): 1625-32.
Schafer, et al (1992) "Induction of a cellular immune response to a foreign antigen by a recombinant Listeria monocytogenes vaccine." J Immunology, 149(1) 53-59.
Bast, et al (1975) "Antitumor activity of bacterial infection. II. effect of Listeria monocytogenes on growth of a guinea pig hepatoma." J Natl. Cancer Inst., 54(3): 757-761.
Brasseur, et al (1992) "Human gene MAGE-1, which codes for a tumor-rejection antigen, is expressed by some breast tumors." Int. J Cancer 52(5):839-841.
Chamberlain, et al (2000) "Innovations and strategies for the development of anticancer vaccines." Expert Opinion on Pharmacotherapy, 1(4): 603-614.
Scardino, et al (2002) "HER-2/neu and hTERT Cryptic Epitopes as Novel Targets for Broad Spectrum Tumor Immunotherapy." The Journal of Immunology, vol. 168, 5900-5906.
Disis, et al (1996) Peptide-Based, but Not Whole Protein, Vaccines Elicit Immunity to HER-2/neu, an Oncogenic Self Protein. The Journal of Immunology, vol. 156, 3151-3158.
Coussens, et al (1985)"Tyrosine Kinase Receptor with Extensive Homology to EGF Receptor Shares Chromosomal Location with neu Oncogene." Science. vol. 230, 1132-1139.
Adams et al. (1992) "Cre-*lox* recombination in *Escherichia coli* cells. Mechanistic differences from the in vitro reaction." *J. Mol. Biol.* 226:661-673.
Allison et al. (1997) "Cloning and characterization of a Prevotella melaninogenica hemolysin." *Infect Immun*. 65(7):2765-71.
Amici et al, "DNA vaccination with full-length or truncated Neu induces protective immunity against the development of spontaneous mammary tumors in HER-2/neu transgenic mice" Gene Therapy (2000) 7, 703-706.
An et al. (1996) "A recombinant minigene vaccine containing a nonameric cytoxic-T-Lymphocyte epitope confers limited protection against Listeria monocytogenes infection" *Infect. Immun* 64,(5):1685-1693.
Anderson (1998) "Human gene therapy." *Nature*. Apr. 30;392(6679 Suppl):25-30.
Angelakopoulos et al. (2002) "Safety and shedding of an attenuated strain of Listeria monocytogenes with a deletion of actA/plcB in adult volunteers: a dose escalation study of oral inoculation." *Infect Immun*. 70(7):3592-601.
Angelov et al., "Therapeutic vaccine for acute and chronic motor neuron diseases: implication for amyotrophic lateral sclerosis" PNAS Apr. 15, 2003 vol. 100 No. 8 4790-4795.
Attwood et al. (2000) "The Babel of Bioinformatics" *Science* 290(5491):471-473.
Awwad (1989) "Cyclophosphamide-induced immunologically mediated regression of a cyclophosphamide-resistant murine tumor: a consequence of eliminating precursor L3T4+ suppressor T-cells." *Cancer Res*. 49(7): 1649-1654.
Bear (1986) "Tumor-specific suppressor T-cells which inhibit the in vitro generation of cytolytic T-cells from immune and early tumor-bearing host spleens." *Cancer Res*. Apr;46(4 Pt 1):1805-12.
Bernhard et al. (2002) "Vaccination against the HER-2/neu oncogenic protein." *Endocrine-Related Cancer*, 9:33-44.
Bielecki et al. (1990) "Bacillus subtilis expressing a haemolysin gene from Listeria monocytogenes can grow in mammalian cells" *Nature* 354:175-176.
Billington et al. (1997) "The Arcanobacterium (Actinomyces) pyogenes hemolysin, pyolysin, is a novel member of the thiol-activated cytolysin family." *J Bacteriol*. Oct;179(19):6100-6.
Bodmer et al. (1988) "Enhanced recognition of a modified peptide antigen by cytotoxic T cells specific for influenza nucleoprotein." *Cell* 52: 253-258.
Boon et al. (2006) "Human T cell responses against melanoma" *Annu Rev Immunol*. 24:175-208.
Bourquin et al. (2000) "Myelin oligodendrocyte glycoprotein-DNA vaccination induces antibody-mediated autoaggression in experimental autoimmune encephalomyelitis" *Eur J Immunol* 30:3663-3671.
Boyer et al. (2005) "DNA prime Listeria boost induces a cellular immune response to SIV antigens in the rhesus macaque model that is capable of limited suppression of SIV239 viral replication." *Virology*. Mar. 1;333(1):88-101.
Brockstedt et al. (2004) "Listeria-based cancer vaccines that segregate immunogenicity from toxicity." *Proc Natl Acad Sci USA*. 101(38):13832-7.
Bron et al. (2004) "Identification of Lactobacillus plantarum genes that are induced in the gastrointestinal tract of mice." *J Bacteriol*. Sep;186(17):5721-9.
Brown et al. (1988) "Site-specific integration in Saccaropolyspora erythraea and multisite integration in Streptomyces lividans of actinomycete plasmid pSE101." *J. Bacteriology* 170: 2287-2295.
Bruhn et al. (2005) "Characterization of anti-self CD8 T-cell responses stimulated by recombinant Listeria monocytogenes expressing the melanoma antigen TRP-2." *Vaccine*. Jul. 21;23(33):4263-72.
Brundage et al. (1993) "Expression and phosphorylation of the Listeria monocytogenes ActA protein in mammalian cells." *Proc. Natl. Acad. Sci. USA* 90: 11890-11894.
Bubert et al. (1997) "The Listeria monocytogenes iap gene as an indicator gene for the sudy of PrfA-dependent regulation." *Mol Gen Genet*. Sep;256(1):54-62.
Calendar et al. Poster presented at the ISOPOL Meeting 2001, http://64.233.169.104/search?q=cache:mA_uJpQsCrcJ.www.ma.uni-heidelberg.de/inst/imh/download/isopol.doc+Portnoy+Isopol+2001&hl=en&ct=clnk&cd=3&gl=us.
Camilli et al. (1993) "Dual roles of plcA in Listeria monocytogenes pathogenesis." *Mol. Microbiol*. 8:143-157.
Carbone (1989) "Induction of ovalbumin-specific cytotoxic T cells by in vivo peptide immunization." *J Exp Med* 169:603-612.
Carbone (1990) "Class I-restricted processing and presentation of exogenous cell-associated antigen in vivo." *J Exp Med* 171:377-387.
Chen et al, "DNA Vaccines Encoding Full-Length or Truncated Neu Induce Protective Immunity against Neu-expressing Mammary Tumors" [Cancer Research 58. 1965-1971. May 1, 1998.
Concetti et al, "Autoantibody to p185erbB2/neu oncoprotein by vaccination with xenogenic DNA" Cancer Immunol Immunother. Dec. 1996;43(5):307-15.
Courvalin et al. (1995) "Gene transfer from bacteria to mammalian cells." *C R Acad Sci III*. Dec;318(12):1207-12.
Cunto-Amesty et al. (2003) "Strategies in cancer vaccines development." *Int J Parasitol*. 33(5-6):597-613.

Dakappagari et al. (2000) "Prevention of mammary tumors with a chimeric HER-2 B-cell epitope peptide vaccine." *Cancer Res.* Jul. 15;60(14):3782-9.

Darji et al. (2003) "Induction of immune responses by attenuated isogenic mutant strains of Listeria monocytogenes." *Vaccine* 1;21 Suppl 2:S102-9.

Darji et al. (1997) "Oral somatic transgene vaccination using attenuated *S. typhimurium*" *Cell* 91:765-775.

Darji et al. (1995) "Hyperexpression of listeriolysin in the nonpathogenic species Listeria innocua and high yield purification." *J Biotechnol.* Dec. 15;43(3):205-12.

Darji et al. (1995) "Listeriolysin generates a route for the presentation of exogenous antigens by major histocompatibility complex class I." *Eur J Immunol.* Oct;25(10).2967-71.

Darji et al. (1997) "TAP-dependent major histocompatibility complex class I presentation of soluble proteins using listeriolysin." *Eur J Immunol.* Jun;27(6):1353-9.

Decatur et al. (2000) "A Pest-like sequence in Listeriolysin O essential for Listeria monocytogenes pathogenicity" *Science* 290(5493):992-995.

Dermime et al. (2004) "Vaccine and antibody-directed T cell tumour immunotherapy." *Biochim Biophys Acta.* 1704(1):11-35.

Deshpande et al. (1997) "Isolation of a contact-dependent haemolysin from Mycobacterium tuberculosis." *J Med Microbiol.* Mar;46(3):233-8.

Di Carlo et al, "Inhibition of mammary carcinogenesis by systemic interleukin 12 or p185neu DNA vaccination in Her-2/neu transgenic BALB/c mice" Clin Cancer Res. Mar. 2001;7(3 Suppl):830s-837s.

Dietrich et al. (1998) "Delivery of antigen-encoding plasmid DNA into the cytosol of macrophages by attenuated suicide Listeria monocytogenes" *Nature Biotechnology* 15:181-185.

Dietrich et al. (2001) "From evil to good: a cytolysin in vaccine development." *Trends Microbiol.* Jan;9(1):23-8.

Disis et al., "Generation of T-Cell Immunity to the HER-2/neu Protein After Active Immunization With HER-2/neu Peptide—Based Vaccines" J Clin Oncol 20:2624-2632, 2002.

Dramsi et al. (1995) "Entry of Listeria monocytogenes into hepatocytes requires expression of inIB, a surface protein of the internalin multigene family." *Mol Microbiol.* 16(2):251-61.

Dunn et al. (1991) "Selective radiation resistance of immunologically induced T cells as the basis for irradiation-induced T-cell-mediated regression of immunogenic tumor." *J Leukoc Biol.* 49(4):388-396.

Dumitrescu et al, "Understanding breast cancer risk—where do we stand in 2005?" J. Cell. Mol. Med. vol. 9, No. 1, 2005 pp. 208-221.

Ebert et al. (1990) "Selective immunosuppressive action of a factor produced by colon cancer cells." *Cancer Res.* 50(19): 6158-6161.

Esserman et al, "Vaccination with the extracellular domain of p185neu prevents mammary tumor development in neu transgenic mice" Cancer Immunol Immunother. Feb. 1999;47(6):337-42.

Ezzel (1995) "Cancer Vaccines: An Idea Whose Time Has Come?" J. NIH Res., 7:46-49.

Falk et al. (1991) "Identification of naturally processed viral nonapeptides allows their quantification in infected cells and suggests an allele-specific T cell epitope forecast." *J Exp Med.* 174(2):425-434.

Finn et al. (2003) "Cancer vaccines: between the idea and the reality." *Nature Reviews Immunology* 3:630-641.

Foy et al, "Vaccination with Her-2/neu DNA or protein subunits protects against growth of a Her-2/neu-expressing murine tumor" Vaccine. Mar. 21, 2001;19(17-19):2598-606.

Frankel et al. (1995) "Induction of cell-mediated immune responses to human immunodeficiency virus type 1 Gag protein by using Listeria monocytogenes as a live vaccine vector." *J. Immunol.* 155:4775-4782.

Frey (1993) "Rat adenocarcinoma 13762 expresses tumor rejection antigens but tumor-bearing animals exhibit tumor-specific immunosuppression." *Clin Immunol Immunopathol.* 69(2):223-233.

Friedman et al. (2000) "Induction of human immunodeficiency virus (HIV)-specific CD8 T-cell responses by Listeria monocytogenes and a hyperattenuated Listeria strain engineered to express HIV antigens." *J. Virology* 74 9987-9993.

Fu et al. (1990) "Expansion of immunoregulatory macrophages by granulocyte-macrophage colony-stimulating factor derived from a murine mammary tumor." *Cancer Res.* 50(2):227-234.

Fujii (1987) "Significance of suppressor macrophages for immunosurveillance of tumor-bearing mice." *J Natl Cancer Inst.* 78(3):509-517.

Furukawa (1993) "Nude mouse metastatic models of human stomach cancer constructed using orthotopic implantation of histologically intact tissue." *Cancer Res.* 53(5):1204-1208.

Galen et al. (2001) "Can a 'flawless' live vector vaccine strain be engineered?" *Trends Microbiol.* 9(8):372-6.

Gentschev et al. (1995) "Salmonella strain secreting active Listeriolysin changes its intracellular localization" *Infect. Immun.* 63:4202-4205.

Gentschev et al. (1996) "Development of antigen-delivery systems, based on the *Escherichia coli* hemolysin secreatiohn pathway." *Gene* 179:133-140.

Gilmore et al. (1989) "A Bacillus cereus cytolytic determinant, cereolysin AB, which comprises the phospholipase C and sphingomyelinase genes: nucleotide sequence and genetic linkage." *J Bacteriol.* Feb;171(2):744-53.

Glomski et al. (2002) "The Listeria monocytogenes hemolysin has an acidic pH optimum to compartmentalize activity and prevent damage to infected host cells." *J Cell Biol.* Mar. 18;156(6):1029-38.

Goebel et al. (1993) "Listeria monocytogenes—a model system for studying the pathomechanisms of an intracellular microorganism." *Zbt. Bakt.* 278:334-347.

Goossens et al. (1992) "Induction of protective CD8+ T lymphocytes by an attenuated Listeria monocytogenes actA mutant." *Int Immunol.* Dec:4(12):1413-8.

Goossens et al. (1995) "Attenuated Listeria monocytogenes as a live vector for induction of CD8+ T cells in vivo: a study with the nucleoprotein of the lymphocytic choriomeningitis virus." *Int Immunol.* May;7(5):797-805.

Gregory et al. (1997) "Internalin B promotes the replication of Listeria monocytogenes in mouse hepatocytes". *Infect Immun.* 65(12):5137-41.

Gunn et al. (2002) "Recombinant Intra-cellular Bacteria as Carriers for Tumor Antigens." In *Vaccine Delivery Strategies*, Chapter 14, Eds. Guido Dietrich and Werner Goebel, Horizon Scientific Press, UK.

Hassan et al. (2004) "Mesothelin: a new target for immunotherapy." *Clin Cancer Res.* 10(12 Pt 1):3937-42.

Hauf et al. (1997) "Listeria monocytogenes infection of P388D1 macrophages results in a biphasic NF-kappaB (RelA/p50) activation induced by lipoteichoic acid and bacterial phospholipases and mediated by IkappaBalpha and IkappaBbeta degradation." *Proc Natl Acad Sci U S A.* Aug. 19:94(17):9394-9.

Hess et al. (1995) "Listeria monocytogenes p60 supports host cell invasion by and in vivo survival of attenuated Salmonella typhimurium." *Infect Immun.* May;63(5):2047-53.

Hess et al. (1996) "Salmonella typhimurium aroA- infection in gene-targeted immunodeficient mice: major role of CD4+ TCR-alpha beta cells and IFN-gamma in bacterial clearance independent of intracellular location." *J Immunol.* May 1;156(9):3321-6.

Hess et al. (1996) "Superior efficacy of secreted over somatic antigen display in recombinant Salmonella vaccine induced protection against listeriosis" *Proc. Nat. Acad. Sci.* 93:1458-1463.

Hess et al. (1997) "Protection against murine listeriosis by an attenuated recombinant Salmonella typhimurium vaccine strain that secretes the naturally somatic antigen superoxide dismutase." *Infect Immun.* Apr;65(4):1286-92.

Hess et al. (1998) "Mycobacterium bovis bacilli Calmette-Guerin strains secreting listeriolysin of Listeria monocytogenes" *Proc. Natl. Acad. Sci.* 95:5299-5304.

Higgins et al. (1998) "Bacterial delivery of DNA evolves." *Nat Biotechnol.* Feb;16(2):138-9.

Hodgson (2000) "Generalized transduction of serotype 1/2 and serotype 4b strains of Listeria monocytogenes." *Mol Microbiol.* 35(2):312-23.

Huang et al. (1994) "Role of bone marrow-derived cells in presenting MHC class I-restricted tumor antigens." *Science* 264961-965.

Hussain et al. (2004) "CD4+CD25+ regulatory T cells that secrete TGFbeta and IL-10 are preferentially induced by a vaccine vector." *J Immunother.* Sep-Oct;27(5):339-46.

Ikonomidis et al. (1994) Abstract E-90, Abstracts, 94th General Meeting of the American Society for Microbiology, May 23-27.

Jensen (1997) "Recombinant Listeria monocytogenes vaccination eliminates papillomavirus-induced tumors and prevents papilloma formation from viral DNA." *J Virol.* 71(11):8467-8474.

Jones et al. (1994) "Characterization of Listeria monocytogenes pathogenesis in a strain expressing perfringolysin O in place of listeriolysin O." *Infect. Immun.* 62:5608-5613.

Kaufman et al. (1999) "Impact of intracellular location of and antigen display by intracellular bacteria: implications for vaccine development" *J Immunol. Lett,* 65(1-2):81-84.

Kocks et al. (1992) "L. monocytogenes-induced actin assembly requires the ActA gene product" *Cell* 68(3):521-531.

Kovacsovics-Bankowski at al. (1993) "Efficient major histocompatibility complex class I presentation of exogenous antigen upon phagocytosis by macrophages." *Proc. Natl. Acad. Sci. USA* 90:4942-4946.

Lacey et al., "Phase IIa Safety and Immunogenicity of a Therapeutic Vaccine, TA-GW, in Persons with Genital Warts" The Journal of Infectious Diseases 1999;179:612-618.

Lampson et al. (1993) "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ." *Cancer Research* 53:176-182.

Lasa et al. (1997) "Identification of two regions in the N-terminal domain of ActA involved in the actin comet tail formation by Listeria monocytogenes" *EMBO* 16(7):1531-40.

Lauer et al. (2002) "Construction, characterization, and use of two Listeria monocytogenes site-specific phage integration vectors." *J. Bacteriology* 184: 4177-4186.

Lauer at al. ASM Meeting, Abstract 1999.

Leão et al. (1995) "A species-specific nucleotide sequence of Mycobacterium tuberculosis encodes a protein that exhibits hemolytic activity when expressed in *Escherichia coli.*" *Infect Immun.* Nov;63(11):4301-6.

Lee et al. (1991) "Construction of single-copy integration vectors for *Staphylococcus aureus.*" *Gene* 103:101-5.

Lehner at al. (1996) "Processing and delivery of peptides presented by MHC class I molecules." *Curr Opin Immunol.* 8(1):59-67.

Lejeune (1994) "Nitric oxide involvement in tumor-induced immunosuppression." *J Immunol.* 152(10):5077-5083.

Liau et al. (2002) "Tumor immunity within the central nervous system stimulated by recombinant Listeria monocytogenes vaccination." *Cancer Res.* 62(8):2287-93.

Lin et al. (1996) Treatment of established tumors with a novel vaccine that enhances Major Histocompatibility Class II presentation of tumor antigen *Cancer Res.* 56:21-26.

Lin et al. (2002) "Oral vaccination with recombinant Listeria monocytogenes expressing human papillomavirus type 16 E7 can cause tumor growth in mice to regress." *Int J Cancer.* Dec. 20;102(6):629-37.

Lingnau et al. (1995) "Expression of the Listeria monocytogenes EGD inlA and inlB genes, whose products mediate bacterial entry into tissue culture cell lines, by PrfA-dependent and -independent mechanisms." *Infect Immun.* Oct;63(10):3896-903.

Loeffler et al. (2006) "Comparison of different live vaccine strategies in vivo for delivery of protein antigen or antigen-encoding DNA and mRNA by virulence-attenuated Listeria monocytogenes." *Infect Immun.* Jul;74(7):3946-57.

Loessner et al. (1995) "Heterogeneous endolysins in Listeria monocytogenes bacteriophages: a new class of enzymes and evidence for conserved holin genes within the siphoviral lysis cassettes." *Mol Microbiol.* Jun;16(6):1231-41.

Loessner et al. (2000) "Complete nucleotide sequence, molecular analysis and genome structure of bacteriophage A118 of Listeria monocytogenes: implications for phage evolution." *Molecular Microbiology* 35(2):324-40.

Makela et al. (1987) Hand Book of Experimental Immunology, vol. 1, chapter 3, pp. 3.1-3.13.

Manjili et al. (2003) "HSP110-HER2/neu chaperone complex vaccine induces protective immunity against spontaneous mammary tumors in HER-2/neu transgenic mice," *J Immunol.* Oct. 15;171(8):4054-61.

Marquis et al. (1997) "Proteolytic pathways of activation and degradation of a bacterial phospholipase C during intracellular infection by Listeria monocytogenes." *J. Cell Biol.* 137:1381-1392.

Martin et al. (1986) "Nucleotide sequence of the tetM tetracycline resistance determinant of the streptococcal conjugative shuttle transposon Tn1545." *Nucleic Acid Res.* 14:7047-7058.

Marx et al. (2002) "Broad-host-range cre-lox system for antibiotic marker recycling in gram-negative bacteria." *Biotechniques.* Nov;33(5):1062-7.

McLaughlan et al. (1998) "Molecular characterization of an autolytic amidase of Listeria monocytogenes EGD." *Microbiology.* May;144(Pt 5):1359-67.

Mengaud et al. (1988) "Expression in *Escherichia coli* and sequence analysis of the Listeriolysin O determinant of Listeria Monocytogenes" *Infection and Immunity* 56(4):766-772.

Mikayama et al. (1993) "Molecular cloning and functional expression of a CDNA encoding gycosylation-inhibiting factor" *Proc. Natl. Acad. Sci. USA* 90:10056-10060.

Mlynárová et al. (2002) "The promiscuity of heterospecific lox sites increases dramatically in the presence of palindromic DNA." *Gene.* Aug. 21;296(1-2):129-37.

Mollet et al. (1993) "Directed genomic integration, gene replacement, and integrative gene expression in Streptococcus thermophilus." *J. Bacteriology* 175:4315-4324.

Moriishi et al. (1998) "Sequence analysis of the actA gene of Listeria monocytogenes isolated from human" *Microbiol. Immunol.* 42(2):129-132.

Ngo et al. (1994) "Computational complexity, protein structure prediction, and the Levinthal paradox" Chptr 14 (492-495) in *The Protein Folding Problem and Tertiary Structure Prediction,* Merz and Le Grand, eds., Birkhauser.

Ochsenbein et al. (1999) "A comparison of T cell memory against the same antigen induced by virus versus intracellular bacteria." *Proc Natl Acad Sci U S A.* Aug. 3;96(16):9293-8.

Oscarsson et al. (1996) "Induction of haemolytic activity in *Escherichia coli* by the slyA gene product." *Mol Microbiol.* Apr;20(1):191-9.

Palmeros et al. (2000) "A family of removable cassettes designed to obtain antibiotic-resistance-free genomic modifications of *Escherichia coli* and other bacteria." *Gene.* Apr. 18;247(1-2):255-64.

Pan et al. (1995) "A recombinant Listeria monocytogenes vaccine expressing a model tumour antigen protects mice against lethal tumour cell challenge and causes regression of established tumours." *Nature Med.* 1:471-477.

Pan et al. (1995) "Regression of established tumors in mice mediated by the oral administration of a recombinant Listeria monocytogenes vaccine" *Cancer Res* 55:4776-4779.

Parida et al. (1998) "Internalin B is essential for adhesion and mediates the invasion of Listeria monocytogenes into human endothelial cells." *Mol Microbiol.* Apr;28(1):81-93.

Paul et al. (1989) "Fundamental Immunology", Second Edition, Raven Press, 987-988.

Penichet et al. (2001) "Antibody-cytokine fusion proteins for the therapy of cancer." *J. Immunological Methods* 248:91-101.

Peters et al. (2003) "Tailoring host immune responses to Listeria by manipulation of virulence genes—the interface between innate and acquired immunity." *FEMS Immunol Med Microbiol.* Apr. 1;35(3):243-53.

Pfeifer et al. (1993) "Phagocytic processing of bacterial antigens for class I MHC presentation to T cells." *Nature.* Jan. 28;361(6410):359-62.

Piechocki et al., "Complementary Antitumor Immunity Induced by Plasmid DNA Encoding Secreted and Cytoplasmic Human ErbB-2" The Journal of Immunology, 2001, 167: 3367-3374.

Pilon et al, "Vaccination with Cytoplasmic ErbB-2 DNA Protects Mice from Mammary Tumor Growth Without Anti-ErbB-2 Antibody" The Journal of Immunology, 2001, 167: 3201-3206.

Pupa et al. (2001) "Prevention of spontaneous neu-expressing mammary tumor development in mice transgenic for rat proto-neu by DNA vaccination." *Gene Ther.* Jan;8(1):75-9.

Quénée et al. (2005) "Combined sacB-based negative selection and cre-lox antibiotic marker recycling for efficient gene deletion in pseudomonas aeruginosa." *Biotechniques.* Jan;38(1):63-7.

Raveneau et al. (1992) "Reduced virulence of a Listeria monocytogenes phospholipase-deficient mutant obtained by transposon insertion into the zinc metalloprotease gene." *Infect. Immun.* 60: 916-921.

Realini et al. (1994) "KEKE motifs. Proposed roles in protein-protein association and presentation of peptides by MHC class I receptors" *FEBS Letters* 348:109-113.

Rechsteiner et al. (1996) "PEST sequences and regulation by proteolysis" *TIBS* 21:267-271.

Reiter et al. (1989) "Transfer RNA genes frequently serve as integration sites for prokaryotic genetic elements." *Nucleic Acids Research* 17(5)1907-14.

Renard et al. (2003) "HER-2 DNA and protein vaccines containing potent Th cell epitopes induce distinct protective and therapeutic antitumor responses in HER-2 transgenic mice." *J Immunol.* 171(3):1588-95.

Repique (1992) "Immunosuppression derived from human B-lymphoblastoid and melanoma cell lines." *Cancer Invest.* 10(3):201-208.

Roden et al. (2004) "Vaccination to prevent and treat cervical cancer." *Hum Pathol* 35(8):971-82.

Rovero et al., "DNA Vaccination Against Rat Her-2/Neu p185 More Effectively Inhibits Carcinogenesis Than Transplantable Carcinomas in Transgenic BALB/c Mice" The Journal of Immunology, 2000, 165: 5133-5142.

Rüssmann et al. (1998) "Delivery of epitopes by the Salmonella type III secretion system for vaccine development." *Science.* Jul. 24;281(5376):565-8.

Safley et al. (1991) "Role of Listeriolysin-o (LLO) in the T Lymphocyte response to infection with Listeria Monocytogenes" *J Immunol.* 146(10):3604-3616.

Scheirlinck et al. (1989) "Integration and expression of alpha-amylase and endoglucanase genes in the Lactobacillus plantarum chromosome." *Appl Environ Microbiol* 55(9):2130-7.

Schlom et al., "Cancer Vaccines:Moving Beyond Current Paradigms" Clin Cancer Res 2007;13(13) Jul. 1, 2007.

Schmidt et al. (1995) "Molecular Analysis of the Plasmid-Encoded Hemolysin of *Escherichia coli* O157:H7 Strain EDL 933" *Infection and Immunity*, 63(3):1055-1061.

Scortti et al. (2007) "The PrfA virulence regulon." *Microbes Infect.* Aug;9(10):1196-207.

Sewell et al. (2004) "Regression of HPV-positive tumors treated with a new Listeria monocytogenes vaccine." *Arch Otolaryngol Head Neck Surg* 130:92-97.

Sewell et al. (2004) "Recombinant Listeria vaccines containing PEST sequences are potent immune adjuvants for the tumor-associated antigen human papillomavirus-16 E7." *Cancer Res.* Dec. 15;64(24):8821-5.

Shen et al. (1998) "Compartmentalization of bacterial antigens: differential effects on priming of CD8 T cells and protective immunity." *Cell.* Feb. 20;92(4):535-45.

Shetron-Rama et al. (2002) "Intracellular induction of Listeria monocytogenes actA expression." *Infect. Immun.* 70:1087-1096.

Shimizu et al. (1994) "Effects of CD4+ and CD8+ T cells in tumor-bearing mice on antibody production." *Cancer Immunol Immunother.* 38(4):272-276.

Singh et al. (2005) "Fusion to Listeriolysin O and delivery by Listeria monocytogenes enhances the immunogenicity of HER-2/neu and reveals subdominant epitopes in the FVB/N mouse." *J Immunol.* Sep. 15;175(6):3663-73.

Sirard et al. (1997) "Intracytoplasmic delivery of Listeriolysin O by a vaccinal strain of Bacillus anthracis induces CD8-mediated protection against listeria monocytogenes" *J Immun.* 159:4435-4443.

Skolnick et al. (2000) "From genes to protein structure and function: novel applications of computational approached in the genomic era" *Trends in Biotech.* 18(1):34-39.

Slifka et al. (1996) "Antiviral cytotoxic T-cell memory by vaccination with recombinant Listeria monocytogenes." *J. Virol.* 70(5):2902-10.

Smith et al. (1995) "The two distinct phospholipases C of Listeria monocytogenes have overlapping roles in escape from a vacuole and cell-to-cell spread." *Infect. Immun.* 63 4231-4237.

Souders et al. (2006) "In vivo bactofection: listeria can function as a DNA-cancer vaccine." *DNA Cell Biol.* Mar;25(3):142-51.

Stahl et al. (1984) "Replacement of the Bacillus subtilis subtilisin structural gene with an In vitro-derived deletion mutation." *J. Bacteriol* 158:411-418.

Starks et al. (2004) "Listeria monocytogenes as a vaccine vector: virulence attenuation or existing antivector immunity does not diminish therapeutic efficacy." *J. Immunology* 173:420-427.

Stitz et al. (1990) "Characterization and immunological properties of influenza A virus nucleoprotein (NP): cell-associated NP isolated from infected cells or viral NP expressed by vaccinia recombinant virus do not confer protection." *J Gen Virol.* 71(Pt 5):1169-1179.

Strugnell et al. (1990) "Stable expression of foreign antigens from the chromosome of Salmonella typhimurium vaccine strains." *Gene* 88:57-63.

Stryer et al. (1998) Biochemistry, Third Edition, WH Freeman Company, New York, 31-33.

Sun et al. (1990) "Isolation of Listeria monocytogenes small-plaque mutants defective for intracellular growth and cell-to-cell spread." *Infect. Immun.* 58 3770-3778.

Tanabe et al. (1999) "Induction of Protective T Cells against Listeria monocytogenes in Mice by Immunization with a Listeriolysin O-Negative Avirulent Strain of Bacteria and Liposome-Encapsulated Listeriolysin O" *Infect. Immun.* 67(2):568-575.

Thull et al, "Recogntion and management of hereditary breast cancer syndromes" The Oncologist, 2004; 9: 13-24.

Tilney et al. (1989) "Actin filaments and the growth, movement, and spread of the intracellula bacterial parasite, Listeria monocytogenes." *J Cell Biol.* Oct;109(4 Pt 1):1597-608.

Vasil et al. (1982) "Cloning of a phosphate-regulated hemolysin gene (phospholipase C) from Pseudomonas aeruginosa." *J Bacteriol.* Oct;152(1):431-40.

Vazquez-Boland et al. (1992) "Nucleotide sequence of the lecithinase operon of Listeria monocytogenes and possible role of lecithinase in cell-to-cell spread." *Infect. Immun.* 60:219-230.

Verch et al. (2004) "Listeria monocytogenes-based antibiotic resistance gene-free antigen delivery system applicable to other bacterial vectors and DNA vaccines." *Infect Immun.* Nov;72(11):6418-25.

Verma et al. (1995) "Delivery of class I and class II MHC-restricted T-cell epitopes of listerolysin of listeria monocytogenes by attenuated salmonella", *Vaccine* 13(2):142-150.

Vitiello et al. "Development of a Lipopeptide-based therapeutic vaccine to treat chronic HBV infection" J Clin Invest. Jan. 1995; 95(1): 341-349.

Walker et al. (1994) "Tumor growth alters T cell and macrophage production of and responsiveness to granulocyte-macrophage colony-stimulating factor: partial dysregulation through interleukin-10." *Cell Immunol.* 154(1):342-357.

Wei et al, "Protection against mammary tumor growth by vaccination with full-length, modified human ErbB-2 DNA." Int J Cancer. May 31, 1999;81(5):748-54.

Watson et al. (1991) "Splenic macrophages from tumor-bearing mice co-expressing MAC-1 and MAC-2 antigens exert immunoregulatory functions via two distinct mechanisms." *J Leukoc Biol.* 49(2): 126-138.

Wei et al. (2005) "Listeria monocytogenes phosphatidylinositol-specific phospholipase C has evolved for virulence by greatly reduced activity on GPI anchors." *Proc. Natl. Acad. Sci. USA* 102:12927-12931.

Weidt et al. (1994) "CD8+ T lymphocyte-mediated antiviral immunity in mice as a result of injection of recombinant viral proteins." *J Immunol.* Sep. 15;153(6):2554-61.

Weiskirch et al. (1997) "Listeria monocytogenes: a potent vaccine vector for neoplastic and infectious disease." *Immunological Reviews* 158:159-169.

Wirth et al. (1986) "Highly efficient protoplast transformation system for Streptococcus faecalis and a new *Escherichia coli*-S. faecalis shuttle vector." *J Bacteriol.* 165(3):831-6.

Wu et al. (1995) "Engineering an intracellular pathway for major histocompatibility complex class II presentation of antigens" *Cancer Res.* 56:21-26.

Young et al, (1992) "Tumor-derived cytokines induce bone marrow suppressor cells that mediate immunosuppression through transforming growth factor beta." *Cancer Immunol Immunother.* 35(1): 14-18.

Young et al. (1995) "Holins: form and function in bacteriophage lysis." *FEMS Microbiol Rev.* Aug;17(1-2):191-205.

Zhang et al. (1993) "Functional replacement of the hemolysin A transport signal by a different primary sequence." *Proc Natl Acad Sci U S A.* May 1;90(9):4211-5.

Beattie IA, Swaminathan B, Ziegler HK, Cloning and charcterization of T-cell-reactive protein antogens from Listeria monocytogenes, infect Immune. Sep. 1990, 58(9):2792-803.

Beaucage et al., "Deoxynucelotide phosphoramidites—a new class of key intermediates for deoxypolynucleotide synthesis", 1981, Tetra. Lett., 22:1859-1862.

Bouwer HG, Barry RA, Hinrichs DJ, Acquired immunity to an intracellular pathogen: immunologic recognition of L. monocytogenes-infected cells, Immunol. Rev. Aug. 1997; 158:137-46.

Bouwer HG, Hinrichs DJ, Cytotoxic-T-Iymphocyte responses to epitopes of listeriolysin O and p60 following infection with Listeria monocytogenes, Infect. Immune. Jul. 1996; 64(7):2515-22.

Brown et al., "Chemical synthesis and cloning of a tyrosine tRNA gene" 1979, Meth. Enzymol. 68:109-151 .

Bruder D, Darji A, Gakamsky DM, Chakraborty T, Pecht I, Wehland J, Wehland J, Weiss S, Efficient induction of cytotoxic CD8+ T cells against exogenous proteins: establishment and characterization of a T cell line specific for the membrane protein ActA OF Listeria monocytogenes, Eur. J. Immunol. Sep. 1998; 28(9):2630-9.

Catic A, Dietrich G, Gentschev I, Goebel W, Kaufmann SH, Hess J., Introduction of protein or DNA delivered via recombinant Salmonella typhimurium into the major histocompatibility complex class I presentation pathway of macrophages, Microbes Infect., Feb. 1999, 1(2):113-21.

Cenatiempo, "Prokaryotic gene expression in vitro: transcription-translation coupled systems." 1986, Biochimie 68:505-516.

Darji A, Bruder D, Zur Lage S, Gerstel B, Chakraborty T, Wehland J, Weiss S, The role of the bacterial membrane protein ActA in immunity and protection against Listeria monocytogenes, J. Immunol. Sep. 1, 1998, 161(5):2414-20.

Darji A, Stockinger B, Wehland J, Chakraborty T, Weiss S, Antigen-specific T cell receptor antagonism by antigen-presenting cells treated with the hemolysin of Listeria monocytogenes: a noval type of immune escape, Eur. J. Immunol. Jul. 1997; 27(7):1696-703.

Darji A, Stockinger B, Wehland J, Chakraborty T, Weiss S, T-cell anergy induced by antigen presenting cells treated with the hemolysin of Listeria monocytogenes, Immunol. Lett. Jun. 1, 1997, 57(1-3):33-7.

De Boer et al., "A division inhibitor and a topological specificity factor coded for by the minicell locus determine proper placement of the division septum in *E. coli*." 1989, Cell 56:641-649.

Doling AM, Ballard JD, Shen H, Krishna KM, Ahmed R, Collier RJ, Starnbach MN, Cytotoxic T-lymphocyte epitopes fused to anthrax toxin induce protective antiviral immunity, Infect. Immun. Jul. 1999; 67(7):3290-6.

Ezzel, 1995, "Cancer Vaccines: An Idea Whose Time Has Come?" J. NIH Res., 7:46-49.

Garay-Malparticla HM, et al., "CaSPredictor: a new computer-based tool for caspase substrate prediction", Bioinformatics Jun. 2005; 21 Suppl. 1: i169-76.

Gilman et al., "Isolation of sigma-28-specific promoters from Bacillus subtilis DNA" 1984, Gene 32:11-20.

Glick, "Factors affecting the expression of foreign proteins in *Escherichia coli*" 1987, J. Ind. Microbiol. 1:277-282.

Gold L. et al., "Translational initiation in prokaryotes." 1981, Ann. Rev. Microbiol. 35:365-404.

Gottesman, "Bacterial regulation: global regulatory networks." 1984, Ann. Rev. Genet. 18:415-442.

Guzman Carlos A et al.: "Attenuated Listeria monocytogenes carrier strains can deliver an HIV-1 gp120 T helper epitope to MHC class II-restricted human CD4+ T cells", European Journal of Immunology, vol. 28, No. 6, Jun. 1998, pp. 1807-1814.

Harty JT, Pamer EG, CD8 T lymphocytes specific for the secreted p60 antigen protect against Listeria monocytogenes infection, J. Immunol. May 1, 1995; 154(9):4642-50.

Hess J., Kaufmann SH, Abstract, Live antigen carriers as tools for improved anti-tuberculosis vaccines, FEMS Immunol, Med. Microbiol. Feb. 1999; 23(2):165-73.

Higgins DE, Shastri N, Portnoy DA, Abstract, Delivery of protein to the cytosol of macrophages using *Escherichia coli* K-12, Mol. Microbiol. Mar. 1999 31(6)1631-41.

Hiltbold EM, Safley SA, Ziegler HK, The presentation of class I and class II epitopes of listeriolysin O is regulated by intracellular localization and by intracelluar spread of Listeria monocytogenes, J. Immunol. Aug. 1, 1996; 157(3):1163-75.

Hiltbold EM, Ziegler HK, Mechanisms of processing and presentation of the antigens of Listeria monocytogenes, Infect Agents Dis. Oct. 1993; 2(5):314-23.

International Search Report of Application No. PCT/US07/06292 issued on Jun. 17, 2008.

International Search Reports of Application No. PCT/US07/10635.

International Search Reports of Application No. PCT/US08/03067.

Jensen et al., 1997, "Recombinant Listeria monocytogenes as a live vaccine vehicle and a probe for studying-cell-mediated immunity" Immunological Review 158:147-157.

Knutson K. L. et al., "Immunization with a HER-2/neu helper peptide vaccine generates HER-2/neu CD8 T-cell immunity in cancer patients." The Journal of Clinical Investegation, 107:477-484, 2001.

Kyte J. and Dootlittle RF, "A simple method for displaying the hydropathic character of a protein" J. Mol. Biol. 157, 105, 1982.

Lauer et al., "Systematic mutational analysis of the amino-terminal domain of the Listeria monocytogenes ActA protein reveals novel functions in actin-based motility" Molecular Microbiology 42(5):1163-1177, 2001.

Lebrun M. et al., Aug. 1996, "Internallan must be on the Bacterial Surface to mediate Entry of Listeria monocytogenes into Epilhalial Cells", Molecullar Microbiology 21:579-592.

Lee KD, Oh YK, Portnoy DA, Swanson JA, Delivery of macromolecules into cytosol using liposomes containig hemolysin from Listeria monocytogenes, J. Biol. Chem., Mar. 29, 1996, 271(13):7249-52.

Lipford GB, Wagner H, Heeg K, Vaccination with immunodominant peptides encapsulated in Quil A-containing liposomes induces peptide-specific primary CD8+ cytotoxic T cells, Vaccine Jan. 1994; 12(1):73-80.

Mazzaccaro RJ, Gedde M, Jensen ER, Van Santen HM, Polegh HL, Rock KL, Bloom BR, Major histocompatibility class I presentation of soluble antigen facilitated by Mycobacterium tuberculosis infection, Proc. Natl. Acad. Sci. U.S.A. Oct. 15, 1996; 93(21):11786-91.

Merrifiled et al., "Solid phase peptide synthesis. 1. The synthesis of a tetrapeptide" J. Am. Chem. Soc., 85:2149-2156 (1963).

Miller et al., "Targeted vectors for gene therapy" 1995, FASEB J., 9:190-199.

Narang et al., "Improved phosphotriester method for the synthesis of gene fragments" 1979. Meth. Enzymol. 68:90-99.

Naz NK et al., "Novel human prostate-specific cDNA: molecular cloning, expression, and immunobiology of the recombinant protein" Biochem Biophys Res. Commun. 297:1075-84, 2002.

Nielsen PE, "Peptide nucleic acids as therapeutic agents" Curr. Opin. Struct Biol. 9:353-57, 1999.

Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.

Paterson, "Rational approaches to immune regulation", Immunologic Research, 2003; 27/2-3:451-462.

Schnupf et al., "Phosphorylation, ubiquitination and degradation of listeriolysic O in mammalian cells: role of the PEST-like sequence" Cellular microbiology 8(2):353-364, 2006.

Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.

Skoble J. et al., Aug. 7, 2000, "Three Regions within ActA Promote Atp2/3 Complex-mediated Actin Nucleation and Listeria monocytogenes Motility", The Journal of cell Biology 150(3):527-537.

Smith G.A. et al., Sep. 1995, "Asymmetric Distribution of the Listeria monocytogenes ActA Protein is Required and Sufficient to Direct Actin-Based Motility", Molecular Microbiology 17:945-951.

Szalay G, Hess J. Kaufmann SH, Presentation of Listeria monocytogenes antigens by major histocompatibility complex class I molecules to CD8 cytotoxic T lymphocytes independent of listeriolysin secretion and virulence, Eur. J. Immunol. Jul. 1994; 24(7):1471-7.

Teitelbaum R, Cammer M, Maitland ML, Freitag NE, Condeelis J., Bloom BR, Mycobacterial infection of macrophages results in membrane-permeable phagosomes, Proc. Natl. Acad. Sci. U.S.A, Dec. 21, 1999, 96(26):15190-5.

Ulmanen et al., "Transcription and translation of foreign genes in Bacillus Subtilis by the aid of a secretion vector" 1985, J. Bacteriol. 162:176-182.

Vazquez MA, Sicher SC, Proctor ML, Crowley JC, Lu CY, Differential regulation of la expression and antigen presentation by listeriolysin-producing versus non-producing strains of Listens monocytogenes, J. Leukoc Biol. May 1996; 59(5):683-90.

Villanueva MS, Sijts AJ, Pamer EG, Listeriolysin is processed efficiently into an MHC class l-associated epitope in Listeria monocytogenes-infected cells, J. Immunol. Dec. 1, 1995; 155(11):5227-33.

Vines A. et al., "Identfication and characterization of nucleotide sequence difference in three virulence-associate genes of listeria monocytogenes strains representing clinically important serotypes", Current Microbiology, May 1998, vol. 36, No. 5, pp. 309-318.

Ward et al., "Construction and characterisation of a series of multicopy promoter-probe plasmid vectors for Streptomyces using the aminoglycoside phosphotransferase gene from Tn5 as indicator" 1986, Mol. Gen. Genet. 203:468-478.

Welch M.D. et al., Jul. 3, 1998, "Interaction of Human Arp2/3 Complex and the Listeria monocytogenes ActA Protein in Actin Filament Nucleation" Science 281:105-108; pa-998020.

Wilson RL, White DW, Harty JT, Transient expression of bacterial gene fragments in eukaryotic cells implications for CD8(+) T cell epitope analaysis, J. Immunol. Methods, Feb. 3, 2000; 234 (1-2):137-47.

Wu et al., "Engineering an itracellular pathway for major histrocompatibility complex class II presentation of antigens", Proc. Natl. Acad. Sci. USA, 1995, 92:11671-5.

Zwickey HL, Potter TA, Antigen secreted from noncytosolic Listeria monocytogenes is processed by the classical MHC class I processing pathway, J. Immunol. Jun. 1, 1999; 162(11):6341-50.

Zwickey HL, Potter TA, "Peptide epitopes from noncytosolic Listeria monocytogenes can be presented by major histocompatibility complex class I molecules", Infect. Immun. May 1996; 64(5):1870-2.

Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.

Ikonomidis et al., "Influenze-specific immunity induced by recombinant Listeria monoctogenese vaccines", Vaccine, vol. 15, No. 4, 1997, pp. 433-440.

Rogers et al., "Amino acid sequences common to rapidly degraded proteins: The pest hypothesis", Science, vol. 234, 1986, pp. 364-368.

Dustoor, "Antitumor activity of listeria monocytogenes on a guinea pig fibrosarcoma", infection and immunity, 1999, vol, 23, No. 1, pp. 54-60.

* cited by examiner

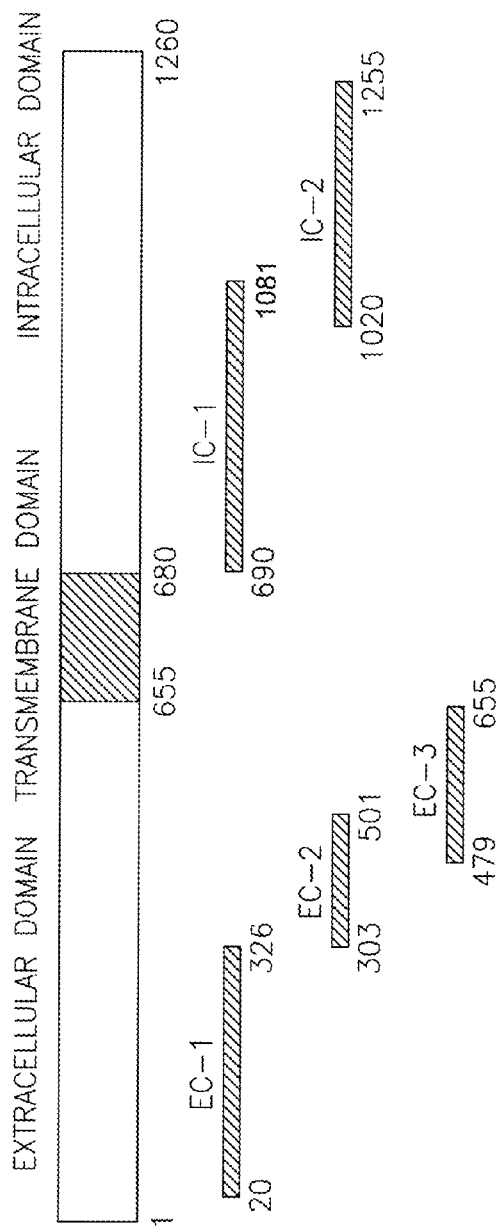
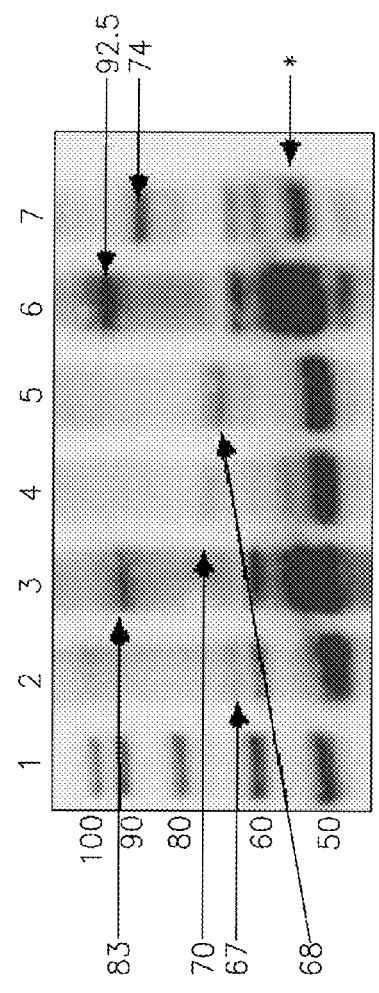
FIG.2A
FIG.2B

SEQUENCE LISTING

<160> NUMBER OF SEQ ID NOS: 54

<210> SEQ ID NO 1
<211> LENGTH: 47
<212> TYPE: DNA
<213> ORGANISM: Artificial
<220> FEATURE:
<223> OTHER INFORMATION: primer

<400> SEQUENCE: 1
cacgcggatg aaatcgataa gctcgagccc cccggaatcg cgggcac                47

<210> SEQ ID NO 2
<211> LENGTH: 38
<212> TYPE: DNA
<213> ORGANISM: Artificial
<220> FEATURE:
<223> OTHER INFORMATION: primer

<400> SEQUENCE: 2
ccggactagt gacctcttgg ttattcgggg gacacacc                38

<210> SEQ ID NO 3
<211> LENGTH: 34
<212> TYPE: DNA
<213> ORGANISM: Artificial
<220> FEATURE:
<223> OTHER INFORMATION: primer

<400> SEQUENCE: 3
ccgggtcgac tgcccctaca actacctgtc tacg                34

<210> SEQ ID NO 4
<211> LENGTH: 58
<212> TYPE: DNA
<213> ORGANISM: Artificial

```
<220> FEATURE:
<223> OTHER INFORMATION: primer

<400> SEQUENCE: 4
ccggactagt ttacttgtca tcgtcgtcct tgtagtcccc actgtggagc agggcctg          58

<210> SEQ ID NO 5
<211> LENGTH: 34
<212> TYPE: DNA
<213> ORGANISM: Artificial
<220> FEATURE:
<223> OTHER INFORMATION: primer

<400> SEQUENCE: 5
ccgggtcgac tgctttgtac acactgtacc ttgg                                    34

<210> SEQ ID NO 6
<211> LENGTH: 58
<212> TYPE: DNA
<213> ORGANISM: Artificial
<220> FEATURE:
<223> OTHER INFORMATION: primer

<400> SEQUENCE: 6
ccggactagt ttacttgtca tcgtcgtcct tgtagtccgg gctggctctc tgctctgc          58

<210> SEQ ID NO 7
<211> LENGTH: 35
<212> TYPE: DNA
<213> ORGANISM: Artificial
<220> FEATURE:
<223> OTHER INFORMATION: primer

<400> SEQUENCE: 7
ccggctcgag tatacgatgc gtaggctgct gcagg                                   35

<210> SEQ ID NO 8
<211> LENGTH: 34
<212> TYPE: DNA
<213> ORGANISM: Artificial
<220> FEATURE:
<223> OTHER INFORMATION: primer

<400> SEQUENCE: 8
ccggactagt agccagtgga gatctggggg gccc                                    34

<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
ccggctcgag ggtgacctgg tagacgctga ag                                      32

<210> SEQ ID NO 10
<211> LENGTH: 32
<212> TYPE: DNA
<213> ORGANISM: Artificial
<220> FEATURE:
<223> OTHER INFORMATION: primer

<400> SEQUENCE: 10
ccggctcgag ggtgacctgg tagacgctga ag                                      32
```

<210> SEQ ID NO 11
<211> LENGTH: 22
<212> TYPE: DNA
<213> ORGANISM: Rattus rattus

<400> SEQUENCE: 11
ccgggccgaa ttcgcaatga tc                                         22

<210> SEQ ID NO 12
<211> LENGTH: 34
<212> TYPE: DNA
<213> ORGANISM: Rattus rattus

<400> SEQUENCE: 12
ccccgaattc ctactgaggg ttcccacgga tcaa                            34

<210> SEQ ID NO 13
<211> LENGTH: 42
<212> TYPE: DNA
<213> ORGANISM: Rattus rattus

<400> SEQUENCE: 13
gacatgaagt tgcggctccc tagtctcaca gagatcctga ag                   42

<210> SEQ ID NO 14
<211> LENGTH: 34
<212> TYPE: DNA
<213> ORGANISM: Rattus rattus

<400> SEQUENCE: 14
ccccgaattc ctactcaggg ttgtgcatgg actc                            34

<210> SEQ ID NO 15
<211> LENGTH: 42
<212> TYPE: DNA
<213> ORGANISM: Rattus rattus

<400> SEQUENCE: 15
gacatgaagt tgcggctccc tgccctcgtc acctacaaca ca                   42

<210> SEQ ID NO 16
<211> LENGTH: 34
<212> TYPE: DNA
<213> ORGANISM: Rattus rattus

<400> SEQUENCE: 16
ccccgaattc ctagaggtca cggagactgt ctgg                            34

<210> SEQ ID NO 17
<211> LENGTH: 42
<212> TYPE: DNA
<213> ORGANISM: Artificial
<220> FEATURE:
<223> OTHER INFORMATION: primer

<400> SEQUENCE: 17
gacatgaagt tgcggctccc tatcacaggt tacctgtaca tc                   42

<210> SEQ ID NO 18
<211> LENGTH: 34
<212> TYPE: DNA
<213> ORGANISM: Artificial
<220> FEATURE:
<223> OTHER INFORMATION: primer

<400> SEQUENCE: 18
ccccgaattc ctacttccat actcggcact cctc                          34

<210> SEQ ID NO 19
<211> LENGTH: 42
<212> TYPE: DNA
<213> ORGANISM: Artificial
<220> FEATURE:
<223> OTHER INFORMATION: primer

<400> SEQUENCE: 19
gacatgaagt tgcggctccc tacccagtgt gtcaactgca gt                 42

<210> SEQ ID NO 20
<211> LENGTH: 34
<212> TYPE: DNA
<213> ORGANISM: Artificial
<220> FEATURE:
<223> OTHER INFORMATION: primer

<400> SEQUENCE: 20
ccccggtacc ctagatcttc tgtctccttc gttt                          34

<210> SEQ ID NO 21
<211> LENGTH: 42
<212> TYPE: DNA
<213> ORGANISM: Artificial
<220> FEATURE:
<223> OTHER INFORMATION: primer

<400> SEQUENCE: 21
gacatgaagt tgcggctccc tggcgtcctg ctgttcctga tc                 42

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
ccccggtacc ctaacctcgg tgttctcgga catg                          34

<210> SEQ ID NO 23
<211> LENGTH: 42
<212> TYPE: DNA
<213> ORGANISM: Artificial
<220> FEATURE:
<223> OTHER INFORMATION: primer

<400> SEQUENCE: 23
gacatgaagt tgcggctccc ttccacagta cagctggtga ca                 42

<210> SEQ ID NO 24
<211> LENGTH: 34
<212> TYPE: DNA
<213> ORGANISM: Artificial
<220> FEATURE:
<223> OTHER INFORMATION: primer

<400> SEQUENCE: 24
ccccggtacc ctagcagatt ggaggctgag gtag                          34

<210> SEQ ID NO 25

```
<211> LENGTH: 42
<212> TYPE: DNA
<213> ORGANISM: Artificial
<220> FEATURE:
<223> OTHER INFORMATION: primer

<400> SEQUENCE: 25
gacatgaagt tgcggctccc tgatggaatc ccagcccggg ag                 42

<210> SEQ ID NO 26
<211> LENGTH: 34
<212> TYPE: DNA
<213> ORGANISM: Artificial
<220> FEATURE:
<223> OTHER INFORMATION: primer

<400> SEQUENCE: 26
ccccggtacc ctaccctttcc gagggagcca gtgg                         34

<210> SEQ ID NO 27
<211> LENGTH: 42
<212> TYPE: DNA
<213> ORGANISM: Artificial
<220> FEATURE:
<223> OTHER INFORMATION: primer

<400> SEQUENCE: 27
gacatgaagt tgcggctccc tgagctgaca ctgggcctgg ag                 42

<210> SEQ ID NO 28
<211> LENGTH: 34
<212> TYPE: DNA
<213> ORGANISM: Artificial
<220> FEATURE:
<223> OTHER INFORMATION: primer

<400> SEQUENCE: 28
ccccggtacc ctatacaggt acatccaggc ctag                          34

<210> SEQ ID NO 29
<211> LENGTH: 33
<212> TYPE: DNA
<213> ORGANISM: Artificial
<220> FEATURE:
<223> OTHER INFORMATION: primer

<400> SEQUENCE: 29
ccgggctagc atggtcatca tggagctggc cgg                           33

<210> SEQ ID NO 30
<211> LENGTH: 58
<212> TYPE: DNA
<213> ORGANISM: Artificial
<220> FEATURE:
<223> OTHER INFORMATION: primer

<400> SEQUENCE: 30
ccgggatatc ttacttgtca tcgtcgtcct tgtagtctca tacaggtaca tccaggcc 58

<210> SEQ ID NO 31
<211> LENGTH: 33
<212> TYPE: DNA
<213> ORGANISM: Artificial
<220> FEATURE:
<223> OTHER INFORMATION: primer

<400> SEQUENCE: 31
```
ccgggtcgac atggtcatca tggagctggc cgg                              33

<210> SEQ ID NO 32
<211> LENGTH: 61
<212> TYPE: DNA
<213> ORGANISM: Artificial
<220> FEATURE:
<223> OTHER INFORMATION: primer

<400> SEQUENCE: 32
ccgggatatc ttacttgtca tcgtcgtcct tgtagtctca gacctcttgg ttattcgggg    60
g                                                                    61

<210> SEQ ID NO 33
<211> LENGTH: 1877
<212> TYPE: DNA
<213> ORGANISM: Listeria monocytogenes

<400> SEQUENCE: 33
atgaaaaaaa taatgctagt ttttattaca cttatattag ttagtctacc aattgcgcaa    60
caaactgaag caaaggatgc atctgcattc aataaagaaa attcaatttc atccatggca   120
ccaccagcat ctccgcctgc aagtcctaag acgccaatcg aaagaaaca cgcggatgaa    180 atcgataagt atatacaagg attggattac aataaaaaca atgtattagt ataccacgga   240
gatgcagtga caaatgtgcc gccaagaaaa ggttacaaag atggaaatga atatattgtt   300
gtggagaaaa agaagaaatc catcaatcaa ataatgcag acattcaagt tgtgaatgca    360
atttcgagcc taacctatcc aggtgctctc gtaaaagcga attcggaatt agtagaaaat   420
caaccagatg ttctccctgt aaaacgtgat tcattaacac tcagcattga tttgccaggt   480
atgactaatc aagacaataa aatcgttgta aaaaatgcca ctaaatcaaa cgttaacaac   540
gcagtaaata cattagtgga agatggaat gaaaaatatg ctcaagctta tccaaatgta   600
agtgcaaaaa ttgattatga tgacgaaatg gcttacagtg aatcacaatt aattgcgaaa   660
tttggtacag catttaaagc tgtaaataat agcttgaatg taaacttcgg cgcaatcagt   720
gaagggaaaa tgcaagaaga agtcattagt tttaaacaaa tttactataa cgtgaatgtt   780
aatgaaccta caagaccttc cagattttc ggcaaagctg ttactaaaga gcagttgcaa    840
gcgcttggag tgaatgcaga aaatcctcct gcatatatct caagtgtggc gtatggccgt   900
caagtttatt tgaaattatc aactaattcc catagtacta agtaaaagc tgcttttgat    960 gctgccgtaa gcggaaaatc tgtctcaggt gatgtagaac taacaaatat catcaaaaat  1020
tcttccttca agccgtaat ttacggaggt tccgcaaaag atgaagttca atcatcgac    1080 ggcaacctcg gagacttacg cgatattttg aaaaaaggcg ctactttaa tcgagaaaca  1140 ccaggagttc ccattgctta tacaacaaac ttcctaaaag acaatgaatt agctgttatt  1200
aaaaacaact cagaatatat tgaaacaact tcaaaagctt atacagatgg aaaaattaac  1260
atcgatcact ctggaggata cgttgctcaa ttcaacattt cttgggatga agtaaattat  1320
gatcctgaag gtaacgaaat tgttcaacat aaaaactgga gcgaaaacaa taaaagcaag  1380
ctagctcatt tcacatcgtc catctatttg ccaggtaacg cgagaaatat taatgtttac  1440
gctaaagaat gcactggttt agcttgggaa tggtggagaa cggtaattga tgaccggaac  1500
ttaccacttg tgaaaaatag aaatatctcc atctggggca ccacgctttta tccgaaatat  1560 agtaataaag tagataatcc aatcgaataa ttgtaaaagt aataaaaaat taagaataaa  1620

```
accgcttaac acacacgaaa aaataagctt gttttgcact cttcgtaaat tatttttgtga   1680 agaatgtaga aacaggctta ttttttaatt tttttagaag aattaacaaa tgtaaaagaa   1740
tatctgactg tttatccata taatataagc atatcccaaa gtttaagcca cctatagttt   1800
ctactgcaaa acgtataatt tagttcccac atatactaaa aaacgtgtcc ttaactctct   1860
ctgtcagatt agttgta                                                   1877
```

<210> SEQ ID NO 34
<211> LENGTH: 529
<212> TYPE: PRT
<213> ORGANISM: Listeria monocytogenes

<400> SEQUENCE: 34

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
```

```
            325                 330                 335
Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Lys Ser Lys Leu Ala His Phe
            450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu

<210> SEQ ID NO 35
<211> LENGTH: 307
<212> TYPE: PRT
<213> ORGANISM: Rattus rattus

<400> SEQUENCE: 35

Pro Pro Gly Ile Ala Gly Thr Gln Val Cys Thr Gly Thr Asp Met Lys
1               5                   10                  15

Leu Arg Leu Pro Ala Ser Pro Glu Thr His Leu Asp Met Leu Arg His
            20                  25                  30

Leu Tyr Gln Gly Cys Gln Val Val Gln Gly Asn Leu Glu Leu Thr Tyr
        35                  40                  45

Val Pro Ala Asn Ala Ser Leu Ser Phe Leu Gln Asp Ile Gln Glu Val
    50                  55                  60

Gln Gly Tyr Met Leu Ile Ala His Asn Gln Val Lys Arg Val Pro Leu
65                  70                  75                  80

Gln Arg Leu Arg Ile Val Arg Gly Thr Gln Leu Phe Glu Asp Lys Tyr
                85                  90                  95

Ala Leu Ala Val Leu Asp Asn Arg Asp Pro Gln Asp Asn Val Ala Ala
            100                 105                 110

Ser Thr Pro Gly Arg Thr Pro Glu Gly Leu Arg Glu Leu Gln Leu Arg
        115                 120                 125

Ser Leu Thr Glu Ile Leu Lys Gly Gly Val Leu Ile Arg Gly Asn Pro
    130                 135                 140

Gln Leu Cys Tyr Gln Asp Met Val Leu Trp Lys Asp Val Phe Arg Lys
145                 150                 155                 160

Asn Asn Gln Leu Ala Pro Val Asp Ile Asp Thr Asn Arg Ser Arg Ala
```

```
                    165                 170                 175
Cys Pro Pro Cys Ala Pro Ala Cys Lys Asp Asn His Cys Trp Gly Glu
            180                 185                 190

Ser Pro Glu Asp Cys Gln Ile Leu Thr Gly Thr Ile Cys Thr Ser Gly
        195                 200                 205

Cys Ala Arg Cys Lys Gly Arg Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
            245                 250                 255

Val Thr Tyr Asn Thr Asp Thr Phe Glu Ser Met His Asn Pro Glu Gly
        260                 265                 270

Arg Tyr Thr Phe Gly Ala Ser Cys Val Thr Cys Pro Tyr Asn Tyr
    275                 280                 285

Leu Ser Thr Glu Val Gly Ser Cys Thr Leu Val Cys Pro Pro Asn Asn
    290                 295                 300

Gln Glu Val
305

<210> SEQ ID NO 36
<211> LENGTH: 199
<212> TYPE: PRT
<213> ORGANISM: Rattus rattus

<400> SEQUENCE: 36

Cys Pro Tyr Asn Tyr Leu Ser Thr Glu Val Gly Ser Cys Thr Leu Val
1               5                   10                  15

Cys Pro Pro Asn Asn Gln Glu Val Thr Ala Glu Asp Gly Thr Gln Arg
            20                  25                  30

Cys Glu Lys Cys Ser Lys Pro Cys Ala Arg Val Cys Tyr Gly Leu Gly
        35                  40                  45

Met Glu His Leu Arg Gly Ala Arg Ala Ile Thr Ser Asp Asn Val Gln
    50                  55                  60

Glu Phe Asp Gly Cys Lys Lys Ile Phe Gly Ser Leu Ala Phe Leu Pro
65                  70                  75                  80

Glu Ser Phe Asp Gly Asp Pro Ser Ser Gly Ile Ala Pro Leu Arg Pro
            85                  90                  95

Glu Gln Leu Gln Val Phe Glu Thr Leu Glu Glu Ile Thr Gly Tyr Leu
        100                 105                 110

Tyr Ile Ser Ala Trp Pro Asp Ser Leu Arg Asp Leu Ser Val Phe Gln
    115                 120                 125

Asn Leu Arg Ile Ile Arg Gly Arg Ile Leu His Asp Gly Ala Tyr Ser
    130                 135                 140

Leu Thr Leu Gln Gly Leu Gly Ile His Ser Leu Gly Leu Arg Ser Leu
145                 150                 155                 160

Arg Glu Leu Gly Ser Gly Leu Ala Leu Ile His Arg Asn Ala His Leu
            165                 170                 175

Cys Phe Val His Thr Val Pro Trp Asp Gln Leu Phe Arg Asn Pro His
        180                 185                 190

Gln Ala Leu Leu His Ser Gly
    195

<210> SEQ ID NO 37
<211> LENGTH: 177
```

```
<212> TYPE: PRT
<213> ORGANISM: Rattus rattus

<400> SEQUENCE: 37

Cys Phe Val His Thr Val Pro Trp Asp Gln Leu Phe Arg Asn Pro His
1               5                   10                  15

Gln Ala Leu Leu His Ser Gly Asn Arg Pro Glu Glu Asp Leu Cys Val
            20                  25                  30

Ser Ser Gly Leu Val Cys Asn Ser Leu Cys Ala His Gly His Cys Trp
        35                  40                  45

Gly Pro Gly Pro Thr Gln Cys Val Asn Cys Ser His Phe Leu Arg Gly
    50                  55                  60

Gln Glu Cys Val Glu Glu Cys Arg Val Trp Lys Gly Leu Pro Arg Glu
65                  70                  75                  80

Tyr Val Ser Asp Lys Arg Cys Leu Pro Cys His Pro Glu Cys Gln Pro
                85                  90                  95

Gln Asn Ser Ser Glu Thr Cys Phe Gly Ser Glu Ala Asp Gln Cys Ala
            100                 105                 110

Ala Cys Ala His Tyr Lys Asp Ser Ser Cys Val Ala Arg Cys Pro
        115                 120                 125

Ser Gly Val Lys Pro Asp Leu Ser Tyr Met Pro Ile Trp Lys Tyr Pro
    130                 135                 140

Asp Glu Glu Gly Ile Cys Gln Pro Cys Pro Ile Asn Cys Thr His Ser
145                 150                 155                 160

Cys Val Asp Leu Asp Glu Arg Gly Cys Pro Ala Glu Gln Arg Ala Ser
                165                 170                 175

Pro

<210> SEQ ID NO 38
<211> LENGTH: 391
<212> TYPE: PRT
<213> ORGANISM: Rattus rattus

<400> SEQUENCE: 38

Thr Met Arg Arg Leu Leu Gln Glu Thr Glu Leu Val Glu Pro Leu Thr
1               5                   10                  15

Pro Ser Gly Ala Met Pro Asn Gln Ala Gln Met Arg Ile Leu Lys Glu
            20                  25                  30

Thr Glu Leu Arg Lys Val Lys Val Leu Gly Ser Gly Ala Phe Gly Thr
        35                  40                  45

Val Tyr Lys Gly Ile Trp Ile Pro Asp Gly Glu Asn Val Lys Ile Pro
    50                  55                  60

Val Ala Ile Lys Val Leu Arg Glu Asn Thr Ser Pro Lys Ala Asn Lys
65                  70                  75                  80

Glu Ile Leu Asp Glu Ala Tyr Val Met Ala Gly Val Gly Ser Pro Tyr
                85                  90                  95

Val Ser Arg Leu Leu Gly Ile Cys Leu Thr Ser Thr Val Gln Leu Val
            100                 105                 110

Thr Gln Leu Met Pro Tyr Gly Cys Leu Leu Asp His Val Arg Glu His
        115                 120                 125

Arg Gly Arg Leu Gly Ser Gln Asp Leu Leu Asn Trp Cys Val Gln Ile
    130                 135                 140

Ala Lys Gly Met Ser Tyr Leu Glu Asp Val Arg Leu Val His Arg Asp
145                 150                 155                 160

Leu Ala Ala Arg Asn Val Leu Val Lys Ser Pro Asn His Val Lys Ile
```

```
                165                 170                 175
Thr Asp Phe Gly Leu Ala Arg Leu Leu Asp Ile Asp Glu Thr Glu Tyr
            180                 185                 190

His Ala Asp Gly Gly Lys Val Pro Ile Lys Trp Met Ala Leu Glu Ser
            195                 200                 205

Ile Leu Arg Arg Arg Phe Thr His Gln Ser Asp Val Trp Ser Tyr Gly
            210                 215                 220

Val Thr Val Trp Glu Leu Met Thr Phe Gly Ala Lys Pro Tyr Asp Gly
225                 230                 235                 240

Ile Pro Ala Arg Glu Ile Pro Asp Leu Leu Glu Lys Gly Glu Arg Leu
            245                 250                 255

Pro Gln Pro Pro Ile Cys Thr Ile Asp Val Tyr Met Ile Met Val Lys
            260                 265                 270

Cys Trp Met Ile Asp Ser Glu Cys Arg Pro Arg Phe Arg Glu Leu Val
            275                 280                 285

Ser Glu Phe Ser Arg Met Ala Arg Asp Pro Gln Arg Phe Val Val Ile
            290                 295                 300

Gln Asn Glu Asp Leu Gly Pro Ser Ser Pro Met Asp Ser Thr Phe Tyr
305                 310                 315                 320

Arg Ser Leu Leu Glu Asp Asp Asp Met Gly Asp Leu Val Asp Ala Glu
            325                 330                 335

Glu Tyr Leu Val Pro Gln Gln Gly Phe Pro Ser Pro Asp Pro Thr Pro
            340                 345                 350

Gly Thr Gly Ser Thr Ala His Arg Arg His Arg Ser Ser Ser Thr Arg
            355                 360                 365

Ser Gly Gly Gly Glu Leu Thr Leu Gly Leu Glu Pro Ser Glu Glu Gly
            370                 375                 380

Pro Pro Arg Ser Pro Leu Ala
385                 390

<210> SEQ ID NO 39
<211> LENGTH: 241
<212> TYPE: PRT
<213> ORGANISM: Rattus rattus

<400> SEQUENCE: 39

Gly Asp Leu Val Asp Ala Glu Glu Tyr Leu Val Pro Gln Gln Gly Phe
1               5                   10                  15

Phe Ser Pro Asp Pro Thr Pro Gly Thr Gly Ser Thr Ala His Arg Arg
            20                  25                  30

His Arg Ser Ser Ser Thr Arg Ser Gly Gly Gly Glu Leu Thr Leu Gly
        35                  40                  45

Leu Glu Pro Ser Glu Glu Gly Pro Pro Arg Ser Pro Leu Ala Pro Ser
    50                  55                  60

Glu Gly Ala Gly Ser Asp Val Phe Asp Gly Asp Leu Ala Met Gly Val
65                  70                  75                  80

Thr Lys Gly Leu Gln Ser Leu Ser Pro His Asp Leu Ser Pro Leu Gln
                85                  90                  95

Arg Tyr Ser Glu Asp Pro Thr Leu Pro Leu Pro Glu Thr Asp Gly
            100                 105                 110

Tyr Val Ala Pro Leu Ala Cys Ser Pro Gln Pro Glu Tyr Val Asn Gln
            115                 120                 125

Ser Glu Val Gln Pro Gln Pro Pro Leu Thr Pro Glu Gly Pro Leu Pro
        130                 135                 140
```

```
Pro Val Arg Pro Ala Gly Ala Thr Leu Glu Arg Pro Lys Thr Leu Ser
145                 150                 155                 160

Pro Gly Lys Asn Gly Val Val Lys Asp Val Phe Ala Phe Gly Gly Ala
                165                 170                 175

Val Glu Asn Pro Glu Tyr Leu Val Pro Arg Glu Gly Thr Ala Ser Pro
            180                 185                 190

Pro His Pro Ser Pro Ala Phe Ser Pro Ala Phe Asp Asn Leu Tyr Tyr
        195                 200                 205

Trp Asp Gln Asn Ser Ser Glu Gln Gly Pro Pro Ser Asn Phe Glu
    210                 215                 220

Gly Thr Pro Thr Ala Glu Asn Pro Glu Tyr Leu Gly Leu Asp Val Pro
225                 230                 235                 240

Val
```

<210> SEQ ID NO 40
<211> LENGTH: 1259
<212> TYPE: PRT
<213> ORGANISM: Rattus rattus

<400> SEQUENCE: 40

```
Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
                20                  25                  30

Asp Met Lys Leu Arg Leu Pro Ala Ser Pro Glu Thr His Leu Asp Met
            35                  40                  45

Leu Arg His Leu Tyr Gln Gly Cys Gln Val Val Gln Gly Asn Leu Glu
        50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
        115                 120                 125

Val Ala Ala Ser Thr Pro Gly Arg Thr Pro Glu Gly Leu Arg Glu Leu
    130                 135                 140

Gln Leu Arg Ser Leu Thr Glu Ile Leu Lys Gly Gly Val Leu Ile Arg
145                 150                 155                 160

Gly Asn Pro Gln Leu Cys Tyr Gln Asp Met Val Leu Trp Lys Asp Val
                165                 170                 175

Phe Arg Lys Asn Asn Gln Leu Ala Pro Val Asp Ile Asp Thr Asn Arg
            180                 185                 190

Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
                245                 250                 255

Leu Ala Cys Leu His Phe Asn His Ser Gly Ile Cys Glu Leu His Cys
            260                 265                 270
```

```
Pro Ala Leu Val Thr Tyr Asn Thr Asp Thr Phe Glu Ser Met His Asn
        275                 280                 285
Pro Glu Gly Arg Tyr Thr Phe Gly Ala Ser Cys Val Thr Thr Cys Pro
        290                 295                 300
Tyr Asn Tyr Leu Ser Thr Glu Val Gly Ser Cys Thr Leu Val Cys Pro
305                 310                 315                 320
Pro Asn Asn Gln Glu Val Thr Ala Glu Asp Gly Thr Gln Arg Cys Glu
                325                 330                 335
Lys Cys Ser Lys Pro Cys Ala Arg Val Cys Tyr Gly Leu Gly Met Glu
            340                 345                 350
His Leu Arg Gly Ala Arg Ala Ile Thr Ser Asp Asn Val Gln Glu Phe
        355                 360                 365
Asp Gly Cys Lys Lys Ile Phe Gly Ser Leu Ala Phe Leu Pro Glu Ser
        370                 375                 380
Phe Asp Gly Asp Pro Ser Ser Gly Ile Ala Pro Leu Arg Pro Glu Gln
385                 390                 395                 400
Leu Gln Val Phe Glu Thr Leu Glu Glu Ile Thr Gly Tyr Leu Tyr Ile
                405                 410                 415
Ser Ala Trp Pro Asp Ser Leu Arg Asp Leu Ser Val Phe Gln Asn Leu
            420                 425                 430
Arg Ile Ile Arg Gly Arg Ile Leu His Asp Gly Ala Tyr Ser Leu Thr
        435                 440                 445
Leu Gln Gly Leu Gly Ile His Ser Leu Gly Leu Arg Ser Leu Arg Glu
        450                 455                 460
Leu Gly Ser Gly Leu Ala Leu Ile His Arg Asn Ala His Leu Cys Phe
465                 470                 475                 480
Val His Thr Val Pro Trp Asp Gln Leu Phe Arg Asn Pro His Gln Ala
                485                 490                 495
Leu Leu His Ser Gly Asn Arg Pro Glu Glu Asp Cys Gly Leu Glu Gly
            500                 505                 510
Leu Val Cys Asn Ser Leu Cys Ala His Gly His Cys Trp Gly Pro Gly
        515                 520                 525
Pro Thr Gln Cys Val Asn Cys Ser His Phe Leu Arg Gly Gln Glu Cys
        530                 535                 540
Val Glu Glu Cys Arg Val Trp Lys Gly Leu Pro Arg Glu Tyr Val Ser
545                 550                 555                 560
Asp Lys Arg Cys Leu Pro Cys His Pro Glu Cys Gln Pro Gln Asn Ser
                565                 570                 575
Ser Glu Thr Cys Phe Gly Ser Glu Ala Asp Gln Cys Ala Ala Cys Ala
            580                 585                 590
His Tyr Lys Asp Ser Ser Ser Cys Val Ala Arg Cys Pro Ser Gly Val
        595                 600                 605
Lys Pro Asp Leu Ser Tyr Met Pro Ile Trp Lys Tyr Pro Asp Glu Glu
        610                 615                 620
Gly Ile Cys Gln Pro Cys Pro Ile Asn Cys Thr His Ser Cys Val Asp
625                 630                 635                 640
Leu Asp Glu Arg Gly Cys Pro Ala Glu Gln Arg Ala Ser Pro Val Thr
                645                 650                 655
Phe Ile Ile Ala Thr Val Glu Gly Val Leu Phe Leu Ile Leu Val
            660                 665                 670
Val Val Val Gly Ile Leu Ile Lys Arg Arg Arg Gln Lys Ile Arg Lys
        675                 680                 685
Tyr Thr Met Arg Arg Leu Leu Gln Glu Thr Glu Leu Val Glu Pro Leu
```

-continued

```
            690                 695                 700
Thr Pro Ser Gly Ala Met Pro Asn Gln Ala Gln Met Arg Ile Leu Lys
705                 710                 715                 720

Glu Thr Glu Leu Arg Lys Val Lys Val Leu Gly Ser Gly Ala Phe Gly
                    725                 730                 735

Thr Val Tyr Lys Gly Ile Trp Ile Pro Asp Gly Glu Asn Val Lys Ile
                740                 745                 750

Pro Val Ala Ile Lys Val Leu Arg Glu Asn Thr Ser Pro Lys Ala Asn
                755                 760                 765

Lys Glu Ile Leu Asp Glu Ala Tyr Val Met Ala Gly Val Gly Ser Pro
770                 775                 780

Tyr Val Ser Arg Leu Leu Gly Ile Cys Leu Thr Ser Thr Val Gln Leu
785                 790                 795                 800

Val Thr Gln Leu Met Pro Tyr Gly Cys Leu Leu Asp His Val Arg Glu
                805                 810                 815

His Arg Gly Arg Leu Gly Ser Gln Asp Leu Leu Asn Trp Cys Val Gln
                820                 825                 830

Ile Ala Lys Gly Met Ser Tyr Leu Glu Asp Val Arg Leu Val His Arg
                835                 840                 845

Asp Leu Ala Ala Arg Asn Val Leu Val Lys Ser Pro Asn His Val Lys
850                 855                 860

Ile Thr Asp Phe Gly Leu Ala Arg Leu Leu Asp Ile Asp Glu Thr Glu
865                 870                 875                 880

Tyr His Ala Asp Gly Gly Lys Val Pro Ile Lys Trp Met Ala Leu Glu
                885                 890                 895

Ser Ile Leu Arg Arg Arg Phe Thr His Gln Ser Asp Val Trp Ser Tyr
                900                 905                 910

Gly Val Thr Val Trp Glu Leu Met Thr Phe Gly Ala Lys Pro Tyr Asp
                915                 920                 925

Gly Ile Pro Ala Arg Glu Ile Pro Asp Leu Leu Glu Lys Gly Glu Arg
                930                 935                 940

Leu Pro Gln Pro Pro Ile Cys Thr Ile Asp Val Tyr Met Ile Met Val
945                 950                 955                 960

Lys Cys Trp Met Ile Asp Ser Glu Cys Arg Pro Arg Phe Arg Glu Leu
                965                 970                 975

Val Ser Glu Phe Ser Arg Met Ala Arg Asp Pro Gln Arg Phe Val Val
                980                 985                 990

Ile Gln Asn Glu Asp Leu Gly Pro Ser Ser Pro Met Asp Ser Thr Phe
                995                 1000                1005

Tyr Arg Ser Leu Leu Glu Asp Asp Asp Met Gly Asp Leu Val Asp
        1010                1015                1020

Ala Glu Glu Tyr Leu Val Pro Gln Gln Gly Phe Phe Ser Pro Asp
        1025                1030                1035

Pro Thr Pro Gly Thr Gly Ser Thr Ala His Arg Arg His Arg Ser
        1040                1045                1050

Ser Ser Thr Arg Ser Gly Gly Gly Glu Leu Thr Leu Gly Leu Glu
        1055                1060                1065

Pro Ser Glu Glu Gly Pro Pro Arg Ser Pro Leu Ala Pro Ser Glu
        1070                1075                1080

Gly Ala Gly Ser Asp Val Phe Asp Gly Asp Leu Ala Met Gly Val
        1085                1090                1095

Thr Lys Gly Leu Gln Ser Leu Ser Pro His Asp Leu Ser Pro Leu
        1100                1105                1110
```

Gln Arg Tyr Ser Glu Asp Pro Thr Leu Pro Leu Pro Pro Glu Thr
    1115                1120                1125

Asp Gly Tyr Val Ala Pro Leu Ala Cys Ser Pro Gln Pro Glu Tyr
    1130                1135                1140

Val Asn Gln Ser Glu Val Gln Pro Gln Pro Pro Leu Thr Pro Glu
    1145                1150                1155

Gly Pro Leu Pro Pro Val Arg Pro Ala Gly Ala Thr Leu Glu Arg
    1160                1165                1170

Pro Lys Thr Leu Ser Pro Gly Lys Asn Gly Val Val Lys Asp Val
    1175                1180                1185

Phe Ala Phe Gly Gly Ala Val Glu Asn Pro Glu Tyr Leu Val Pro
    1190                1195                1200

Arg Glu Gly Thr Ala Ser Pro Pro His Pro Ser Pro Ala Phe Ser
    1205                1210                1215

Pro Ala Phe Asp Asn Leu Tyr Tyr Trp Asp Gln Asn Ser Ser Glu
    1220                1225                1230

Gln Gly Pro Pro Pro Ser Asn Phe Glu Gly Thr Pro Thr Ala Glu
    1235                1240                1245

Asn Pro Glu Tyr Leu Gly Leu Asp Val Pro Val
    1250                1255

<210> SEQ ID NO 41
<211> LENGTH: 3952
<212> TYPE: DNA
<213> ORGANISM: Rattus rattus

<400> SEQUENCE: 41
ccgggccgga gccgcaatga tcatcatgga gctggcggcc tggtgccgct gggggttcct      60
cctcgccctc ctgcccccg gaatcgcggg cacccaagtg tgtaccggca cagacatgaa     120
gttgcggctc cctgccagtc ctgagaccca cctggacatg ctccgccacc tgtaccaggg     180
ctgtcaggta gtgcagggca acttggagct tacctacgtg cctgccaatg ccagcctctc     240
attcctgcag gacatccagg aagttcaggg ttacatgctc atcgctcaca accaggtgaa     300
gcgcgtccca ctgcaaaggc tgcgcatcgt gagagggacc cagctctttg aggacaagta     360
tgccctggct gtgctagaca accgagatcc tcaggacaat gtcgccgcct ccaccccagg     420
cagaacccca gagggctgc gggagctgca gcttcgaagt ctcacagaga tcctgaaggg     480
aggagttttg atccgtggga accctcagct ctgctaccag acatggttt tgtggaagga     540
cgtcttccgc aagaataacc aactggctcc tgtcgatata gacaccaatc gttcccgggc     600
ctgtccacct tgtgcccccg cctgcaaaga caatcactgt tggggtgaga gtccggaaga     660
ctgtcagatc ttgactggca ccatctgtac cagtggttgt gcccggtgca agggccggct     720
gcccactgac tgctgccatg agcagtgtgc cgcaggctgc acgggcccca agcattctga     780
ctgcctggcc tgcctccact tcaatcatag tggtatctgt gagctgcact gcccagccct     840
cgtcacctac aacacagaca cctttgagtc catgcacaac cctgagggtc gctacacctt     900
tggtgccagc tgcgtgacca cctgccccta caactacctg tctacggaag tgggatcctg     960
cactctggtg tgtccccga ataaccaaga ggtcacagct gaggacgaa cacagcgttg    1020
tgagaaatgc agcaagccct gtgctcgagt gtgctatggt ctgggcatgg agcaccttcg    1080
aggggcgagg gccatcacca gtgacaatgt ccaggagttt gatggctgca agaagatctc    1140
tgggagcctg gcattttgc ggagagctt tgatgggac cctcctccg gcattgctcc    1200

-continued

```
gctgaggcct gagcagctcc aagtgttcga aaccctggag gagatcacag gttacctgta    1260
catctcagca tggccagaca gtctccgtga cctcagtgtc ttccagaacc ttcgaatcat    1320
tcggggacgg attctccacg atggcgcgta ctcattgaca ctgcaaggcc tgggatcca     1380
ctcgctgggg ctgcgctcac tgcgggagct gggcagtgga ttggctctga ttcaccgcaa    1440
cgcccatctc tgctttgtac acactgtacc ttgggaccag ctcttccgga acccacatca    1500
ggccctgctc cacagtggga accggccgga agaggattgt ggtctcgagg gcttggtctg    1560
taactcactg tgtgcccacg ggcactgctg ggggccaggg cccacccagt gtgtcaactg    1620
cagtcatttc cttcggggcc aggagtgtgt ggaggagtgc cgagtatgga aggggctccc    1680
ccgggagtat gtgagtgaca agcgctgtct gccgtgtcac cccgagtgtc agcctcaaaa    1740
cagctcagag acctgctttg gatcggaggc tgatcagtgt gcagcctgcg cccactacaa    1800
ggactcgtcc tcctgtgtgg ctcgctgccc cagtggtgtg aaaccggacc tctcctacat    1860
gcccatctgg aagtacccgg atgaggaggg catatgccag ccgtgcccca tcaactgcac    1920
ccactcctgt gtggatctgg atgaacgagg ctgcccagca gagcagagag ccagcccggt    1980
gacattcatc attgcaactg tagagggcgt cctgctgttc ctgatcttag tggtggtcgt    2040
tggaatccta atcaaacgaa ggagacagaa gatccggaag tatacgatgc gtaggctgct    2100
gcaggaaact gagttagtgg agccgctgac gcccagcgga gcaatgccca accaggctca    2160
gatgcggatc ctaaaagaga cggagctaag gaaggtgaag gtgcttggat caggagcttt    2220
tggcactgtc tacaagggca tctggatccc agatggggga aatgtgaaaa tccccgtggc    2280
tatcaaggtg ttgagagaaa acacatctcc taaagccaac aaagaaattc tagatgaagc    2340
gtatgtgatg ctggtgtgg ttctccgta tgtgtcccgc ctcctgggca tctgcctgac     2400
atccacagta cagctggtga cacagcttat gccctacggc tgccttctgg accatgtccg    2460
agaacaccga ggtcgcctag ctcccaggga cctgctcaac tggtgtgttc agattgccaa    2520
ggggatgagc tacctggagg acgtgcggct tgtacacagg gacctggctg cccggaatgt    2580
gctagtcaag agtcccaacc acgtcaagat tacagatttc gggctggctc ggctgctgga    2640
cattgatgag acagagtacc atgcagatgg gggcaaggtg cccatcaaat ggatggcatt    2700
ggaatctatt ctcagacgcc ggttcaccca tcagagtgat gtgtggagct atggagtgac    2760
tgtgtgggag ctgatgactt ttgggggccaa accttacgat ggaatcccag cccgggagat    2820
ccctgatttg ctgagaaagg gagaacgcct acctcagcct ccaatctgca ccattgatgt    2880
ctacatgatt atggtcaaat gttggatgat tgactctgaa tgtcgcccga gattccggga    2940
gttggtgtca gaattttcac gtatggcgag gaccccccag cgttttgtgg tcatccagaa    3000
cgaggacttg ggcccatcca gccccatgga cagtaccttc taccgttcac tgctggaaga    3060
tgatgacatg ggtgacctgg tagacgctga agagtatctg gtgccccagc agggattctt    3120
ctcccccgga ccctacccag gcactgggag cacagcccat agaaggcacc gcagctcgtc    3180
caccaggagt ggaggtggtg agctgacact gggcctggag ccctcggaag aagggccccc    3240
cagatctcca ctggctccct cggaaggggc tggctccgat gtgtttgatg gtgacctggc    3300
aatgggggta accaaagggc tgcagagcct ctctccacat gacctcagcc ctctacagcg    3360
gtacagcgag gaccccacat acctctgcc ccccagagact gatggctatg ttgctccccct    3420
ggcctgcagc cccagcccg agtatgtgaa ccaatcagag gttcagcctc agcctccttt    3480
aaccccagag ggtcctctgc ctcctgtccg gcctgctggt gctactctag aaagacccaa    3540
gactctctct cctgggaaga atgggggttgt caaagacgtt tttgccttcg ggggtgctgt    3600
```

```
ggagaaccct gaatacttag taccgagaga aggcactgcc tctccgcccc acccttctcc    3660
tgccttcagc ccagcctttg acaacctcta ttactgggac cagaactcat cggagcaggg    3720
gcctccacca agtaactttg aagggacccc cactgcagag aaccctgagt acctaggcct    3780
ggatgtacct gtatgagacg tgtgcagacg tcctgtgctt tcagagtggg gaaggcctga    3840
cttgtggtct ccatcgccac aaagcaggga gagggtcctc tggccacatt acatccaggg    3900
cagacggctc taccaggaac ctgccccgag gaacctttcc ttgctgcttg aa            3952
```

<210> SEQ ID NO 42
<211> LENGTH: 32
<212> TYPE: PRT
<213> ORGANISM: Rattus rattus

<400> SEQUENCE: 42

Lys Glu Asn Ser Ile Ser Ser Met Ala Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 43
<211> LENGTH: 1255
<212> TYPE: PRT
<213> ORGANISM: Homo sapiens

<400> SEQUENCE: 43

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

-continued

```
Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655
```

```
Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                1020

Leu Val Pro Gln Gln Gly Phe Phe Cys Pro Asp Pro Ala Pro Gly
        1025                1030                1035

Ala Gly Gly Met Val His His Arg His Arg Ser Ser Ser Thr Arg
        1040                1045                1050

Ser Gly Gly Gly Asp Leu Thr Leu Gly Leu Glu Pro Ser Glu Glu
        1055                1060                1065

Glu Ala Pro Arg Ser Pro Leu Ala Pro Ser Glu Gly Ala Gly Ser
```

```
                    1070              1075              1080
Asp Val Phe Asp Gly Asp Leu Gly Met Gly Ala Ala Lys Gly Leu
    1085              1090              1095

Gln Ser Leu Pro Thr His Asp Pro Ser Pro Leu Gln Arg Tyr Ser
    1100              1105              1110

Glu Asp Pro Thr Val Pro Leu Pro Ser Glu Thr Asp Gly Tyr Val
    1115              1120              1125

Ala Pro Leu Thr Cys Ser Pro Gln Pro Glu Tyr Val Asn Gln Pro
    1130              1135              1140

Asp Val Arg Pro Gln Pro Pro Ser Pro Arg Glu Gly Pro Leu Pro
    1145              1150              1155

Ala Ala Arg Pro Ala Gly Ala Thr Leu Glu Arg Pro Lys Thr Leu
    1160              1165              1170

Ser Pro Gly Lys Asn Gly Val Val Lys Asp Val Phe Ala Phe Gly
    1175              1180              1185

Gly Ala Val Glu Asn Pro Glu Tyr Leu Thr Pro Gln Gly Gly Ala
    1190              1195              1200

Ala Pro Gln Pro His Pro Pro Ala Phe Ser Pro Ala Phe Asp
    1205              1210              1215

Asn Leu Tyr Tyr Trp Asp Gln Asp Pro Pro Glu Arg Gly Ala Pro
    1220              1225              1230

Pro Ser Thr Phe Lys Gly Thr Pro Thr Ala Glu Asn Pro Glu Tyr
    1235              1240              1245

Leu Gly Leu Asp Val Pro Val
    1250              1255

<210> SEQ ID NO 44
<211> LENGTH: 4624
<212> TYPE: DNA
<213> ORGANISM: Homo sapiens

<400> SEQUENCE: 44
ggaggaggtg gaggaggagg gctgcttgag gaagtataag aatgaagttg tgaagctgag      60
attcccctcc attgggaccg gagaaaccag gggagccccc cgggcagccg cgcgcccctt     120 cccacgggc  cctttactgc gccgcgcgcc cggcccccac ccctcgcagc accccgcgcc     180
ccgcgccctc ccagccgggt ccagccggag ccatggggcc ggagccgcag tgagcaccat     240
ggagctggcg gccttgtgcc gctgggggct cctcctcgcc ctcttgcccc cggagccgc      300 gagcacccaa gtgtgcaccg gcacagacat gaagctgcgg ctccctgcca gtcccgagac     360
ccacctggac atgctccgcc acctctacca gggctgccag gtggtgcagg gaaacctgga     420
actcacctac ctgcccacca atgccagcct gtccttcctg caggatatcc aggaggtgca     480
gggctacgtg ctcatcgctc acaaccaagt gaggcaggtc ccactgcaga ggctgcggat     540
tgtgcgaggc acccagctct ttgaggacaa ctatgccctg gccgtgctag acaatggaga     600
cccgctgaac aataccaccc ctgtcacagg ggcctcccca ggaggcctgc gggagctgca     660
gcttcgaagc ctcacagaga tcttgaaagg aggggtcttg atccagcgga accccccagct    720 ctgctaccag gacacgattt tgtggaagga catcttccac aagaacaacc agctggctct     780
cacactgata gacaccaacc gctctcgggc ctgccacccc tgttctccga tgtgtaaggg     840
ctcccgctgc tggggagaga gttctgagga ttgtcagagc ctgacgcgca ctgtctgtgc     900
cggtggctgt gcccgctgca aggggccact gcccactgac tgctgccatg agcagtgtgc     960
tgccggctgc acgggcccca agcactctga ctgcctggcc tgcctccact tcaaccacag    1020
```

```
tggcatctgt gagctgcact gcccagccct ggtcacctac aacacagaca cgtttgagtc    1080
catgcccaat cccgagggcc ggtatacatt cggcgccagc tgtgtgactg cctgtcccta    1140
caactacctt tctacggacg tgggatcctg caccctcgtc tgccccctgc acaaccaaga    1200
ggtgacagca gaggatggaa cacagcggtg tgagaagtgc agcaagccct gtgcccgagt    1260
gtgctatggt ctgggcatgg agcacttgcg agaggtgagg gcagttacca gtgccaatat    1320
ccaggagttt gctggctgca agaagatctt tgggagcctg gcatttctgc cggagagctt    1380
tgatggggac ccagcctcca acactgcccc gctccagcca gagcagctcc aagtgtttga    1440
gactctggaa gagatcacag gttacctata catctcagca tggccggaca gcctgcctga    1500
cctcagcgtc ttccagaacc tgcaagtaat ccggggacga attctgcaca atggcgccta    1560
ctcgctgacc ctgcaagggc tgggcatcag ctggctgggg ctgcgctcac tgagggaact    1620
gggcagtgga ctggccctca tccaccataa cacccacctc tgcttcgtgc acacggtgcc    1680
ctgggaccag ctcttccgga acccgcacca agctctgctc cacactgcca accggccaga    1740
ggacgagtgt gtgggcgagg gcctggcctg ccaccagctg tgcgcccgag ggcactgctg    1800
gggtccaggg cccacccagt gtgtcaactg cagccagttc cttcggggcc aggagtgcgt    1860
ggaggaatgc cgagtactgc aggggctccc caggggagtat gtgaatgcca ggcactgttt    1920
gccgtgccac cctgagtgtc agcccagaa tggctcagtg acctgttttg gaccggaggc    1980
tgaccagtgt gtgggcctgtg cccactataa ggaccctccc ttctgcgtgg cccgctgccc    2040
cagcggtgtg aaacctgacc tctcctacat gcccatctgg aagtttccag atgaggaggg    2100
cgcatgccag ccttgcccca tcaactgcac ccactcctgt gtggacctgg atgacaaggg    2160
ctgccccgcc gagcagagag ccagccctct gacgtccatc atctctgcgg tggttggcat    2220
tctgctggtc gtggtcttgg gggtggtctt tgggatcctc atcaagcgac ggcagcagaa    2280
gatccggaag tacacgatgc ggagactgct gcaggaaacg gagctggtgg agccgctgac    2340
acctagcgga gcgatgccca accaggcgca gatgcggatc ctgaaagaga cggagctgag    2400
gaaggtgaag gtgcttggat ctggcgcttt tggcacagtc tacaagggca tctggatccc    2460
tgatggggag aatgtgaaaa ttccagtggc catcaaagtg ttgagggaaa acacatcccc    2520
caaagccaac aaagaaatct agacgaagc atacgtgatg ctggtgtgg ctccccata    2580 tgtctcccgc cttctgggca tctgcctgac atccacggtg cagctggtga cacagcttat    2640
gccctatggc tgcctcttag accatgtccg ggaaaaccgc ggacgcctgg gctcccagga    2700
cctgctgaac tggtgtatgc agattgccaa ggggatgagc tacctggagg atgtgcggct    2760
cgtacacagg gacttggccg ctcggaacgt gctggtcaag agtcccaacc atgtcaaaat    2820
tacagacttc gggctggctc ggctgctgga cattgacgag acagagtacc atgcagatgg    2880
gggcaaggtg cccatcaagt ggatggcgct ggagtccatt ctccgccggc ggttcacccca    2940 ccagagtgat gtgtggagtt atggtgtgac tgtgtgggag ctgatgactt ttggggccaa    3000
accttacgat gggatcccag cccgggagat ccctgacctg ctggaaaagg gggagcggct    3060
gccccagccc cccatctgca ccattgatgt ctacatgatc atggtcaaat gttggatgat    3120
tgactctgaa tgtcggccaa gattccggga gttggtgtct gaattctccc gcatggccag    3180
ggacccccag cgctttgtgg tcatccagaa tgaggacttg ggcccagcca gtccctttga    3240
cagcaccttc taccgctcac tgctggagga cgatgacatg ggggacctgg tgatgctgaa    3300
ggagtatctg gtaccccagc agggcttctt ctgtccagac cctgccccgg gcgctggggg    3360
```

-continued

```
catggtccac cacaggcacc gcagctcatc taccaggagt ggcggtgggg acctgacact      3420
agggctggag ccctctgaag aggaggcccc caggtctcca ctggcaccct ccgaaggggc      3480
tggctccgat gtatttgatg gtgacctggg aatgggggca gccaagggc tgcaaagcct       3540 ccccacacat gaccccagcc ctctacagcg gtacagtgag acccccacag taccctgcc       3600 ctctgagact gatggctacg ttgcccccct gacctgcagc cccagcctg aatatgtgaa       3660 ccagccagat gttcggcccc agccccttc gccccgagag ggccctctgc ctgctgcccg       3720
acctgctggt gccactctgg aaaggcccaa gactctctcc ccagggaaga atggggtcgt      3780
caaagacgtt tttgcctttg ggggtgccgt ggagaacccc gagtacttga caccccaggg     3840
aggagctgcc cctcagcccc accctcctcc tgccttcagc ccagccttcg acaacctcta     3900
ttactgggac caggacccac cagagcgggg ggctccaccc agcaccttca aagggacacc     3960
tacggcagag aacccagagt acctgggtct ggacgtgcca gtgtgaacca aaggccaag      4020 tccgcagaag ccctgatgtg tcctcaggga gcagggaagg cctgacttct gctggcatca    4080
agaggtggga gggccctccg accacttcca ggggaacctg ccatgccagg aacctgtcct    4140
aaggaacctt ccttcctgct tgagttccca gatggctgga aggggtccag cctcgttgga   4200
agaggaacag cactggggag tctttgtgga ttctgaggcc ctgcccaatg agactctagg    4260
gtccagtgga tgccacagcc cagcttggcc ctttccttcc agatcctggg tactgaaagc    4320
cttagggaag ctggcctgag aggggaagcg gccctaaggg agtgtctaag aacaaaagcg    4380
acccattcag agactgtccc tgaaacctag tactgccccc catgaggaag gaacagcaat    4440
ggtgtcagta tccaggcttt gtacagagtg cttttctgtt tagtttttac ttttttttgtt  4500 ttgtttttttt aaagatgaaa taaagaccca gggggagaat gggtgttgta tgggaggca    4560 agtgtggggg gtccttctcc acccactt tgtccatttg caaatatatt ttggaaaaca      4620
gcta                                                                 4624
```

<210> SEQ ID NO 45
<211> LENGTH: 24
<212> TYPE: DNA
<213> ORGANISM: Artificial
<220> FEATURE:
<223> OTHER INFORMATION: primer

<400> SEQUENCE: 45
ctcgaggccg cgagcaccca agtg                                           24

<210> SEQ ID NO 46
<211> LENGTH: 27
<212> TYPE: DNA
<213> ORGANISM: Artificial
<220> FEATURE:
<223> OTHER INFORMATION: primer

<400> SEQUENCE: 46
actagtttaa tcctctgctg tcacctc                                        27

<210> SEQ ID NO 47
<211> LENGTH: 24
<212> TYPE: DNA
<213> ORGANISM: Artificial
<220> FEATURE:
<223> OTHER INFORMATION: primer

<400> SEQUENCE: 47
ctcgagtacc tttctacgga cgtg                                           24

-continued

<210> SEQ ID NO 48
<211> LENGTH: 26
<212> TYPE: DNA
<213> ORGANISM: Artificial
<220> FEATURE:
<223> OTHER INFORMATION: primer

<400> SEQUENCE: 48
actagtttac tctggccggt tggcag                                              26

<210> SEQ ID NO 49
<211> LENGTH: 24
<212> TYPE: DNA
<213> ORGANISM: Artificial
<220> FEATURE:
<223> OTHER INFORMATION: primer

<400> SEQUENCE: 49
ctcgagacgg tgccctggga ccag                                                24

<210> SEQ ID NO 50
<211> LENGTH: 26
<212> TYPE: DNA
<213> ORGANISM: Artificial
<220> FEATURE:
<223> OTHER INFORMATION: primer

<400> SEQUENCE: 50
actagtttag acgatggacg tcagag                                              26

<210> SEQ ID NO 51
<211> LENGTH: 24
<212> TYPE: DNA
<213> ORGANISM: Artificial
<220> FEATURE:
<223> OTHER INFORMATION: primer

<400> SEQUENCE: 51
ctcgagctgc tgcaggaaac ggag                                                24

<210> SEQ ID NO 52
<211> LENGTH: 26
<212> TYPE: DNA
<213> ORGANISM: Artificial
<220> FEATURE:
<223> OTHER INFORMATION: primer

<400> SEQUENCE: 52
actagtttaa gccccttcgg agggtg                                              26

<210> SEQ ID NO 53
<211> LENGTH: 21
<212> TYPE: DNA
<213> ORGANISM: Artificial
<220> FEATURE:
<223> OTHER INFORMATION: primer

<400> SEQUENCE: 53
ctcgaggctg aggagtatct g                                                   21

```
<210> SEQ ID NO 54
<211> LENGTH: 26
<212> TYPE: DNA
<213> ORGANISM: Artificial
<220> FEATURE:
<223> OTHER INFORMATION: primer

<400> SEQUENCE: 54
actagtttac actggcacgt ccagac                                          26
```

*LISTERIA*-BASED AND LLO-BASED VACCINES

CROSS REFERENCE TO RELATED APPLICATION

This application is a continuation-in-part of U.S. application Ser. No. 10/949,667, filed Sep. 24, 2004. This application is hereby incorporated in its entirety by reference herein.

STATEMENT REGARDING FEDERALLY SPONSORED RESEARCH OR DEVELOPMENT

The invention described herein was supported in part by grants from The National Institutes of Health (Grant No. CA72108) and the Department of Defense (W81XWH-04-1-0338). The U.S. Government may have certain rights in this invention.

FIELD OF INVENTION

This invention provides methods of treating and vaccinating against an antigen-expressing tumor and inducing an immune response against a sub-dominant epitope of antigen, comprising a fusion of an LLO fragment to the antigen or a recombinant *Listeria* strain expressing the antigen. The present invention also provides recombinant peptides comprising a listeriolysin (LLO) protein fragment fused to a Her-2 protein or fragment thereof, recombinant *Listeria* strains expressing a Her-2 protein, vaccines and immunogenic compositions comprising same, and methods of inducing an anti-Her-2 immune response and treating and vaccinating against a Her-2-expressing tumor, comprising same.

BACKGROUND OF THE INVENTION

Her-2/neu (referred to henceforth as "Her-2") is a 185 kDa glycoprotein that is a member of the epidermal growth factor receptor (EGFR) family of tyrosine kinases, and consists of an extracellular domain, a transmembrane domain, and an intracellular domain which is known to be involved in cellular signaling (Bargmann C I et al, Nature 319: 226, 1986; King C R et al, Science 229: 974, 1985). It is overexpressed in 25 to 40% of all breast cancers and is also overexpressed in many cancers of the ovaries, lung, pancreas, and gastrointestinal tract. The overexpression of Her-2 is associated with uncontrolled cell growth and signaling, both of which contribute to the development of tumors. Patients with cancers that overexpress Her-2 exhibit tolerance even with detectable humoral, $CD8^+$ T cell, and $CD4^+$ T cell responses directed against Her-2.

*Listeria monocytogenes* is an intracellular pathogen that primarily infects antigen presenting cells and has adapted for life in the cytoplasm of these cells. Host cells, such as macrophages, actively phagocytose *L. monocytogenes* and the majority of the bacteria are degraded in the phagolysosome. Some of the bacteria escape into the host cytosol by perforating the phagosomal membrane through the action of a hemolysin, listeriolysin O (LLO). Once in the cytosol, *L. monocytogenes* can polymerize the host actin and pass directly from cell to cell further evading the host immune system and resulting in a negligible antibody response to *L. monocytogenes*.

SUMMARY OF THE INVENTION

This invention provides methods of treating and vaccinating against an antigen-expressing tumor and inducing an immune response against a sub-dominant epitope of antigen, comprising a fusion of an LLO fragment to the antigen or a recombinant *Listeria* strain expressing the antigen. The present invention also provides recombinant peptides comprising a listeriolysin (LLO) protein fragment fused to a Her-2 protein or fragment thereof, recombinant *Listeria* strains expressing a Her-2 protein, vaccines and immunogenic compositions comprising same, and methods of inducing an anti-Her-2 immune response and treating and vaccinating against a Her-2-expressing tumor, comprising same.

In one embodiment, the present invention provides a recombinant polypeptide comprising an N-terminal fragment of a LLO protein fused to a fragment of a Her-2 protein, the fragment of a Her-2 protein having a length of about 150 to about 420 amino acids.

In another embodiment, the present invention provides a recombinant polypeptide comprising an N-terminal fragment of an LLO protein fused to a Her-2 protein or fused to a fragment thereof.

In another embodiment, the present invention provides a method of inducing an anti-Her-2 immune response in a subject, comprising administering to the subject a recombinant polypeptide comprising an N-terminal fragment of a LLO protein fused to a Her-2 protein or fused to a fragment thereof, or administering a recombinant nucleotide encoding the recombinant polypeptide, thereby inducing an anti-Her-2 immune response in a subjects.

In another embodiment, the present invention provides a method of impeding a growth of a Her-2-expressing tumor in a subject, comprising administering to the subject a recombinant polypeptide comprising an N-terminal fragment of a LLO protein fused to the Her-2 protein or a fragment thereof or a recombinant nucleotide encoding the recombinant polypeptide, whereby the subject mounts an immune response against the Her-2-expressing tumor, thereby impeding, the growth of a Her-2-expressing tumor in a subject.

In another embodiment, the present invention provides a method of shrinking a Her-2-expressing tumor in a subject, comprising administering to the subject a recombinant polypeptide comprising an N-terminal fragment of a LLO protein fused to the Her-2 protein or a fragment thereof or a recombinant nucleotide encoding the recombinant polypeptide, whereby the subject mounts an immune response against the Her-2-expressing tumor, thereby impeding a growth of a Her-2-expressing tumor in a subject.

In another embodiment, the present invention provides a method of impeding a growth of a Her-2-expressing tumor in a subject, comprising administering to the subject a recombinant form of *Listeria* comprising a recombinant nucleotide, the recombinant nucleotide encoding the antigen or a fragment thereof, whereby the subject mounts an immune response against the Her-2-expressing tumor, thereby impeding a growth of a Her-2-expressing tumor in a subject.

In another embodiment, the present invention provides a method of shrinking a Her-2-expressing tumor in a subject, comprising administering to the subject a recombinant form of *Listeria* comprising a recombinant nucleotide, the recombinant nucleotide encoding the antigen or a fragment thereof, whereby the subject mounts an immune response against the Her-2-expressing tumor, thereby impeding a growth of a Her-2-expressing tumor in a subject.

In another embodiment, the present invention provides a method of breaking immune tolerance of a subject to an antigen-expressing tumor, comprising administering to the subject a recombinant polypeptide comprising an N-terminal fragment of a LLO protein fused to a fragment of the antigen or a recombinant nucleotide encoding the recombinant polypeptide, wherein the antigen has one or more dominant CD8+ T cell epitopes and wherein the fragment does not contain any of the dominant CD8+ T cell epitopes, whereby the subject mounts an immune response against the antigen-expressing tumor, thereby breaking immune tolerance of a subject to an antigen-expressing tumor.

In another embodiment, the present invention provides a method of breaking immune tolerance of a subject to an antigen-expressing tumor, comprising administering to the subject a recombinant form of *Listeria* comprising a recombinant nucleotide, the recombinant nucleotide encoding a fragment of the antigen, wherein the antigen has one or more dominant CD8+ T cell epitopes and wherein the fragment does not contain any of the dominant CD8+ T cell epitopes, whereby the subject mounts an immune response against the antigen-expressing tumor, thereby breaking immune tolerance of a subject to an antigen-expressing tumor.

BRIEF DESCRIPTION OF THE FIGURES

FIG. 2. Recombinant *Listeria monocytogenes* is capable of secreting each of Her-2 fragments as a ΔLLO-fusion protein. (A) Map of rat Her-2 fragments. (B) Confirmation of secretion of the fusion peptides by Western blot. Marker (lane 1), Lm-ΔLLO-E7 (lane 2), Lm-ΔLLO-EC1 (lane 3), Lm-ΔLLO-EC2 (lane 4), Lm-ΔLLO-EC3 (lane 5), Lm-ΔLLO-IC1 (lane 6), and Lm-ΔLLO-IC2 (lane 7).

DETAILED DESCRIPTION OF THE INVENTION

Figure 1:
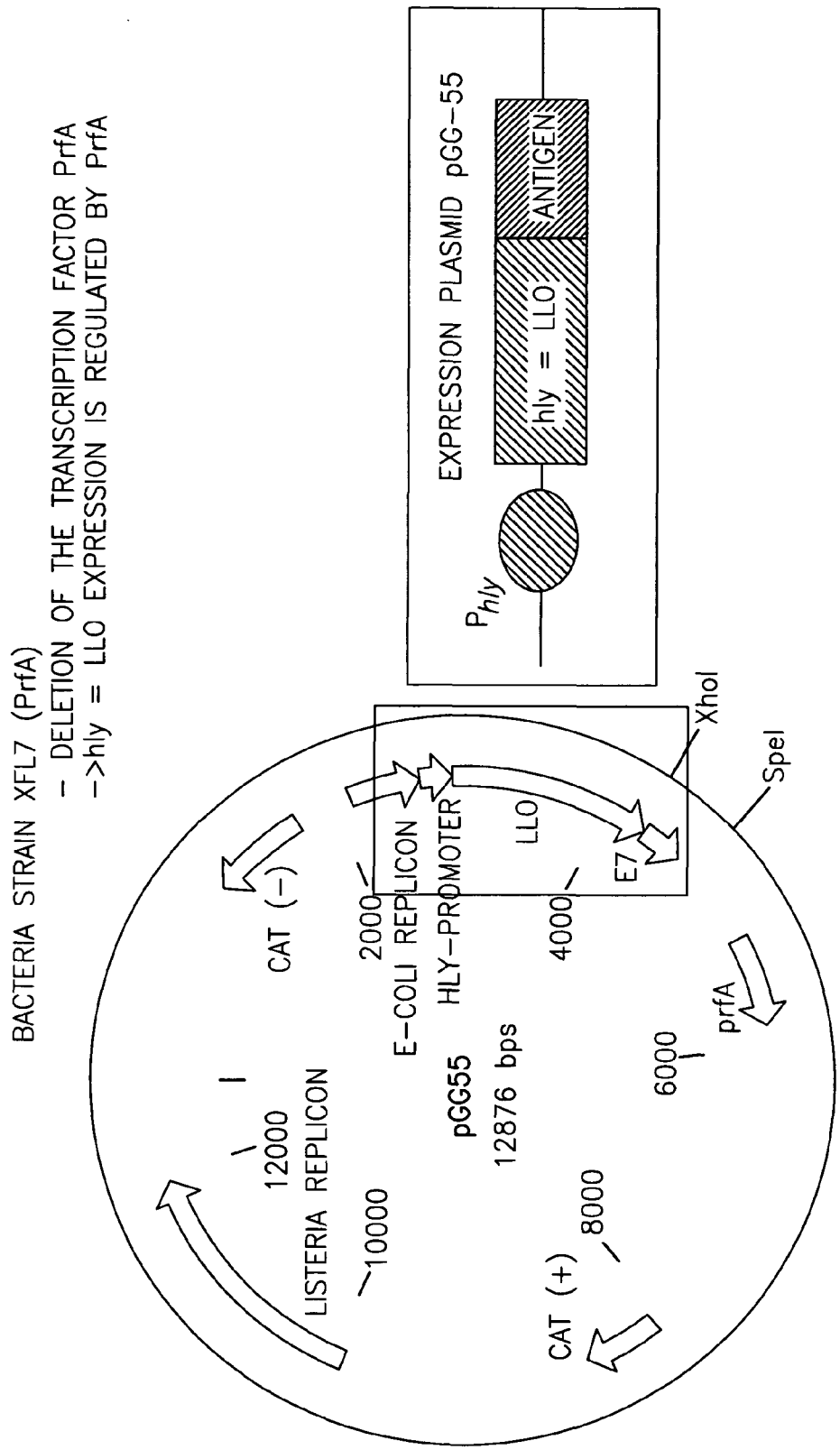
FIG. 1. Schematic representation of pGG55, used to construct the Lm-Δ-LLO-HER-2 vaccines.

This invention provides methods of treating and vaccinating against an antigen-expressing tumor and inducing an immune response against a sub-dominant epitope of antigen, comprising a fusion of an LLO fragment to the antigen or a recombinant *Listeria* strain expressing the antigen. The present invention also provides recombinant peptides comprising a listeriolysin (LLO) protein fragment fused to a Her-2 protein or fragment thereof, recombinant *Listeria* strains expressing a Her-2 protein, vaccines and immunogenic compositions comprising same, and methods of inducing an anti-Her-2 immune response and treating and vaccinating against a Her-2-expressing tumor, comprising same.

As provided herein, the results of the present invention demonstrate that administration of compositions of the present invention has utility for inducing formation of antigen-specific T cells (e.g. cytotoxic T cells) that recognize and kill tumor cells, thereby arresting the growth of and shrinking tumor cells and treating the resulting cancer (Examples herein).

In one embodiment, the present invention provides a recombinant polypeptide comprising an N-terminal fragment of a LLO protein fused to a fragment of a Her-2 protein, the fragment of a Her-2 protein having a length of about 150 to about 420 amino acids.

In another embodiment, the present invention provides a recombinant polypeptide comprising an N-terminal fragment of an LLO protein fused to a Her-2 protein or fused to a fragment thereof.

In another embodiment, the present invention provides a recombinant polypeptide comprising a fragment of a Her-2 protein. In one embodiment, the fragment consists of about AA 20-326 of the Her-2 protein. In another embodiment, the fragment consists of about AA 303-501 thereof. In another embodiment, the fragment consists of about AA 479-655 thereof. In another embodiment, the fragment consists of about AA 690-1081 thereof. In another embodiment, the fragment consists of about AA 1020-1255 thereof. In other embodiments, the fragment consists of any of the Her-2 fragments mentioned below. Each possibility represents a separate embodiment of the present invention.

In one embodiment, the Her-2 protein of methods and compositions of the present invention is a human Her-2 protein. In another embodiment, the Her-2 protein is a mouse Her-2 protein. In another embodiment, the Her-2 protein is a rat Her-2 protein. In another embodiment, the Her-2 protein is a primate Her-2 protein. In another embodiment, the Her-2 protein is a Her-2 protein of any other animal species known in the art. In another embodiment, the Her-2 protein is a variant of a Her-2 protein. In another embodiment, the Her-2 protein is a homologue of a Her-2 protein. Each possibility represents a separate embodiment of the present invention.

In another embodiment, the Her-2 protein is a rat Her-2 protein having the sequence:

(SEQ ID No: 40)
MIIMELAAWCRWGFLLALLPPGIAGTQVCTGTDMKLRLPASPETHLDMLR

HLYQGCQVVQGNLELTYVPANASLSFLQDIQEVQGYMLIAHNQVKRVPLQ

-continued
```
RLRIVRGTQLFEDKYALAVLDNRDPQDNVAASTPGRTPEGLRELQLRSLT

EILKGGVLIRGNPQLCYQDMVLWKDVFRKNNQLAPVDIDTNRSRACPPCA

PACKDNHCWGESPEDCQILTGTICTSGCARCKGRLPTDCCHEQCAAGCTG

PKHSDCLACLHFNHSGICELHCPALVTYNTDTFESMHNPEGRYTFGASCV

TTCPYNYLSTEVGSCTLVCPPNNQEVTAEDGTQRCEKCSKPCARVCYGLG

MEHLRGARAITSDNVQEFDGCKKIFCSLAFLPESFDGDPSSGIAPLRPEQ

LQVFETLEEITGYLYISAWPDSLRDLSVFQNLRIIRGRILHDGAYSLTL

QGLGIHSLGLRSLRELGSGLALIHRNAHLCFVHTVPWDQLFRNPHQALLH

SGNRPEEDCGLEGLVCNSLCAHGHCWGPGPTQCVNCSHFLRGQECVEECR

VWKGLPREYVSDKRCLPCHPECQPQNSSETCFGSEADQCAACAHYKDSSS

CVARCPSGVKPDLSYMPIWKYPDEEGICQPCPINCTHSCVDLDERGCPAE

QRASPVTFIIATVEGVLLFLILVVVVGILIKRRRQKIRKYTMRRLLQETE

LVEPLTPSGAMPNQAQMRILKETELRKVKVLGSGAFGTVYKGIWIPDGEN

VKIPVAIKVLRENTSPKANKEILDEAYVMAGVGSPYVSRLLGICLTSTVQ

LVTQLMPYGCLLDHVREHRGLGSQDLLNWCVQIAKGMSYLEDVRLVHRD

LAARNVLVKSPNHVKITDFGLARLLDIDETEYHADGGKVPIKWMALESIL

RRRFTHQSDVWSYGVTVWELMTFGAKPYDGIPAREIPDLLEKGERLPQPP

ICTIDVYMIMVKCWMIDSECRPRFRELVSEFSRMARDPQRFVVIQNEDLG

PSSPMDSTFYRSLLEDDDMGDLVDAEEYLVPQQGFFSPDPTPGTGSTAHR

RHRSSSTRSGGGELTLGLEPSEEGPPRSPLAPSEGAGSDVFDGDLAMGVT

KGLQSLSPHDLSPLQRYSEDPTLPLPPETDGYVAPLACSPQPEYVNQSEV

QPQPPLTPEGPLPPVRPAGATLERPKTLSPGKNGVVKDVFAFGGAVENPE

YLVPREGTASPPHPSPAFSPAFDNLYYWDQNSSEQGPPPSNFEGTPTAEN

PEYLGLDVPV.
``` was used to create the fragments in Example 1. In another embodiment, the Her-2 protein is encoded for by the nucleic acid sequence set forth in SEQ ID No: 41.

In another embodiment, the Her-2 protein is a human Her-2 protein having the sequence:

```
                                        (SEQ ID No: 43)
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL
```

-continued
```
PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV.
```

SEQ ID No: 43 is used to create the fragments in Example 10. In another embodiment, the Her-2 protein is encoded for by the nucleic acid sequence set forth in SEQ ID No: 44.

In other embodiments, the Her-2 protein has a sequence set forth in GenBank Accession No. NM_004448 or NM_001005862. These Her-2 proteins have transmembrane (TM) regions spanning AA 653-675 and 623-645, respectively. The human Her-2 protein set forth in SEQ ID No: 43 has a TM region spanning 653-676. Thus, in another embodiment, the generation of Her-2 fragments corresponding to those of the present invention from variations of SEQ ID No: 40 such as these requires adjustment of the residue numbers defining the fragments, as described below.

In other embodiments, a Her-2 protein is a protein referred to as "HER-2/neu," "Erbb2," "v-erb-b2," "c-erb-b2," "neu," or "cNeu." Each possibility represents a separate embodiment of the present invention.

In another embodiment, the fragment of a Her-2 protein of methods and compositions of the present invention consists of about amino acid (AA) 20-326 (EC1 of Example 1; SEQ ID No: 35). In another embodiment, the fragment consists of about AA 303-501 (EC2; SEQ ID No: 36) of the Her-2 protein. In another embodiment, the fragment consists of about AA 479-655 (EC3; SEQ ID No: 37) of the Her-2 protein. In another embodiment, the fragment of a Her-2 protein consists of about AA 690-1081 (IC1; SEQ ID No: 38) of the Her-2 protein. In another embodiment, the fragment consists of about AA 1020-255 (IC2; SEQ ID No: 39) of the Her-2- protein. Each possibility represents a separate embodiment of the present invention.

The AA numbers and ranges listed above are based on the rat Her-2 sequence, for which the TM domain spans residues 656-689. In another embodiment, corresponding regions of other Her-2 proteins (e.g. Her-2 proteins from other species) are determined by aligning the TM domains of the other Her-2 proteins and adjusting the AA ranges. For example, for human Her-2 transcript variant 2, GenBank Accession No. NM_001005862, the TM region spans AA 623-645. Thus, in this embodiment, the region of this protein corresponding to EC3 is about AA 446-622, determined by subtracting 33 from the AA numbers to account for the 33 AA difference in the extracellular border of the TM domain. Similarly, the region of this protein corresponding to IC 1 is 646-1037, determined by subtracting 44 from the numbers to account for the 44 AA difference in the intracellular border of the TM domain. In another embodiment, corresponding regions of other Her-2 proteins are determined by alignment with the ends of the protein. Each possibility represents a separate embodiment of the present invention.

In another embodiment, the fragment is a fragment of the extracellular domain of the Her-2 protein. In another embodiment, the fragment consists of about one-third to one-half of the extracellular domain of the Her-2 protein. In another embodiment, the fragment consists of about one-tenth to one-fifth thereof. In another embodiment, the fragment consists of about one-fifth to one-fourth thereof. In another embodiment, the fragment consists of about one-fourth to one-third thereof. In another embodiment, the fragment consists of about one-third to one-half thereof. In another embodiment, the fragment consists of about one-half to three quarters thereof. In another embodiment, the fragment consists of about three quarters to the entire extracellular domain. In another embodiment, the fragment consists of about 5-10% thereof. In another embodiment, the fragment consists of about 10-15% thereof. In another embodiment, the fragment consists of about 15-20% thereof. In another embodiment, the fragment consists of about 20-25% thereof. In another embodiment, the fragment consists of about 25-30% thereof. In another embodiment, the fragment consists of about 30-35% thereof. In another embodiment, the fragment consists of about 35-40% thereof. In another embodiment, the fragment consists of about 45-50% thereof. In another embodiment, the fragment consists of about 50-55% thereof. In another embodiment, the fragment consists of about 55-60% thereof. In another embodiment, the fragment consists of about 5-15% thereof. In another embodiment, the fragment consists of about 10-20% thereof. In another embodiment, the fragment consists of about 15-25% thereof. In another embodiment, the fragment consists of about 20-30% thereof. In another embodiment, the fragment consists of about 25-35% thereof. In another embodiment, the fragment consists of about 30-40% thereof. In another embodiment, the fragment consists of about 35-45% thereof. In another embodiment, the fragment consists of about 45-55% thereof. In another embodiment, the fragment consists of about 50-60% thereof. In another embodiment, the fragment consists of about 55-65% thereof. In another embodiment, the fragment consists of about 60-70% thereof. In another embodiment, the fragment consists of about 65-75% thereof. In another embodiment, the fragment consists of about 70-80% thereof. In another embodiment, the fragment consists of about 5-20% thereof. In another embodiment, the fragment consists of about 10-25% thereof. In another embodiment, the fragment consists of about 15-30% thereof. In another embodiment, the fragment consists of about 20-35% thereof. In another embodiment, the fragment consists of about 25-40% thereof. In another embodiment, the fragment consists of about 30-45% thereof. In another embodiment, the fragment consists of about 35-50% thereof. In another embodiment, the fragment consists of about 45-60% thereof. In another embodiment, the fragment consists of about 50-65% thereof. In another embodiment, the fragment consists of about 55-70% thereof. In another embodiment, the fragment consists of about 60-75% thereof. In another embodiment, the fragment consists of about 65-80% thereof. In another embodiment, the fragment consists of about 70-85% thereof. In another embodiment, the fragment consists of about 75-90% thereof. In another embodiment, the fragment consists of about 80-95% thereof. In another embodiment, the fragment consists of about 85-100% thereof. In another embodiment, the fragment consists of about 5-25% thereof. In another embodiment, the fragment consists of about 10-30% thereof. In another embodiment, the fragment consists of about 15-35% thereof. In another embodiment, the fragment consists of about 20-40% thereof. In another embodiment, the fragment consists of about 30-50% thereof. In another embodiment, the fragment consists of about 40-60% thereof. In another embodiment, the fragment consists of about 50-70% thereof. In another embodiment, the fragment consists of about 60-80% thereof. In another embodiment, the fragment consists of about 70-90% thereof. In another embodiment, the fragment consists of about 80-100% thereof. In another embodiment, the fragment consists of about 5-35% thereof. In another embodiment, the fragment consists of about 10-40% thereof. In another embodiment, the fragment consists of about 15-45% thereof. In another embodiment, the fragment consists of about 20-50% thereof. In another embodiment, the fragment consists of about 30-60% thereof. In another embodiment, the fragment consists of about 40-70% thereof. In another embodiment, the fragment consists of about 50-80% thereof. In another embodiment, the fragment consists of about 60-90% thereof. In another embodiment, the fragment consists of about 70-100% thereof. In another embodiment, the fragment consists of about 5-45% thereof. In another embodiment, the fragment consists of about 10-50% thereof. In another embodiment, the fragment consists of about 20-60% thereof. In another embodiment, the fragment consists of about 30-70% thereof. In another embodiment, the fragment consists of about 40-80% thereof. In another embodiment, the fragment consists of about 50-90% thereof. In another embodiment, the fragment consists of about 60-100% thereof. In another embodiment, the fragment consists of about 5-55% thereof. In another embodiment, the fragment consists of about 10-60% thereof. In another embodiment, the fragment consists of about 20-70% thereof. In another embodiment, the fragment consists of about 30-80% thereof. In another embodiment, the fragment consists of about 40-90% thereof. In another embodiment, the fragment consists of about 50-100% thereof. In another embodiment, the fragment consists of about 5-65% thereof. In another embodiment, the fragment consists of about 10-70% thereof. In another embodiment, the fragment consists of about 20-80% thereof. In another embodiment, the fragment consists of about 30-90% thereof. In another embodiment, the fragment consists of about 40-100% thereof. In another embodiment, the fragment consists of about 5-75% thereof. In another embodiment, the fragment consists of about 10-80% thereof. In another embodiment, the fragment consists of about 20-90% thereof. In another embodiment, the fragment consists of about 30-100% thereof. In another embodiment, the fragment consists of about 10-90% thereof. In another embodiment, the fragment consists of about 20-100% thereof. In another embodiment, the fragment consists of about 10-100% thereof.

In another embodiment, the fragment consists of about 5% of the extracellular domain. In another embodiment, the fragment consists of about 6% thereof. In another embodiment, the fragment consists of about 8% thereof. In another embodiment, the fragment consists of about 10% thereof. In another embodiment, the fragment consists of about 12% thereof. In another embodiment, the fragment consists of about 15% thereof. In another embodiment, the fragment consists of about 18% thereof. In another embodiment, the fragment consists of about 20% thereof. In another embodiment, the fragment consists of about 25% thereof. In another embodiment, the fragment consists of about 30% thereof. In another embodiment, the fragment consists of about 35% thereof. In another embodiment, the fragment consists of about 40% thereof. In another embodiment, the fragment consists of about 45% thereof. In another embodiment, the fragment consists of about 50% thereof. In another embodiment, the fragment consists of about 55% thereof. In another embodiment, the fragment consists of about 60% thereof. In another embodiment, the fragment consists of about 65% thereof. In another embodiment, the fragment consists of about 70% thereof. In another embodiment, the fragment consists of about 75% thereof. In another embodiment, the fragment consists of about 80% thereof. In another embodiment, the fragment consists of about 85% thereof. In another embodiment, the fragment consists of about 90% thereof. In another embodiment, the fragment consists of about 95% thereof. In another embodiment, the fragment consists of about 100% thereof. Each possibility represents a separate embodiment of the present invention.

In another embodiment, the fragment is a fragment of the intracellular domain of the Her-2 protein. In one embodiment, the fragment is from about one third to one-half of the intracellular domain. In another embodiment, the fragment of the intracellular domain is any of the amounts, fractions, or ranges listed above for the extracellular domain. Each possibility represents a separate embodiment of the present invention.

In another embodiment, the fragment of a Her-2 protein of methods and compositions of the present invention does not include a signal sequence thereof. In one embodiment, omission of the signal sequence enables the Her-2 fragment to be successfully expressed in *Listeria*, due the high hydrophobicity of the signal sequence. Each possibility represents a separate embodiment of the present invention.

In another embodiment, the fragment of a Her-2 protein of methods and compositions of the present invention does not include a TM domain thereof. In one embodiment, omission of the TM enables the Her-2 fragment to be successfully expressed in *Listeria*, due the high hydrophobicity of the TM. Each possibility represents a separate embodiment of the present invention.

The LLO utilized in methods and compositions of the present invention is, in one embodiment is a *Listeria* LLO. In one embodiment, the *Listeria* from which the LLO is derived is *Listeria* monocytogenes (LM). In another embodiment, the *Listeria* is *Listeria ivanovii*. In another embodiment, the *Listeria* is *Listeria welshimeri*. In another embodiment, the *Listeria* is *Listeria seeligeri*. In another embodiment, the LLO protein is a non-*Listerial* LLO protein.

In another embodiment, the LLO protein has the sequence:

MKKIMLVFITLILVSLPIAQQTEAKDASAFNKENSISSMAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYPNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

-continued
QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINIDHSGGYVAQFNISWDEVNYDPEGNEIVQH

KNWSENNKSKLAHFTSSIYLPGNARNINVYAKECTGLAWEWWRTVIDDRN

LPLVKNRNISIWGTTLYPKYSNKVDNPIE;

GenBank Accession No. P13128; SEQ ID NO: 34; nucleic acid sequence is set forth in GenBank Accession No. X15127; SEQ ID NO: 33). The first 25 amino acids of the proprotein corresponding to this sequence are the signal sequence and are cleaved from LLO when it is secreted by the bacterium. Thus, in this embodiment, the full length active LLO protein is 504 residues long. In other embodiments, the LLO protein has a sequence set forth in GenBank Accession No. DQ054588, DQ054589, AY878649, U25452, or U25452. In another embodiment, the LLO protein is a variant of an LLO protein. In another embodiment, the LLO protein is a homologue of an LLO protein. Each possibility represents a separate embodiment of the present invention.

In another embodiment, "truncated LLO" or "ΔLLO" refers to a fragment of LLO that comprises the PEST-like domain. In another embodiment, the terms refer to an LLO fragment that does not contain the activation domain at the amino terminus and does not include cystine 484. In another embodiment, the LLO fragment consists of a PEST sequence. In another embodiment, the LLO fragment comprises a PEST sequence. In another embodiment, the LLO fragment consists of about the first 441 amino acids of the LLO protein. In another embodiment, the LLO fragment is a non-hemolytic form of the LLO protein.

In one embodiment, the PEST-like domain referred to above has the sequence set forth in SEQ ID NO: 42. In another embodiment, the PEST-like domain is any other PEST-like domain known in the art. Each possibility represents a separate embodiment of the present invention.

In another embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1-75. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350 In another embodiment, the LLO fragment consists of about residues 1-375 In another embodiment, the LLO fragment consists of about residues 1-400. In another embodiment, the LLO fragment consists of about residues 1-425. Each possibility represents a separate embodiment of the present invention.

In another embodiment, the present invention provides a vaccine comprising a recombinant polypeptide of the present invention.

In another embodiment, the present invention provides a nucleotide molecule encoding a recombinant polypeptide of the present invention. In another embodiment, the present invention provides a vaccine comprising the nucleotide molecule.

In another embodiment, the present invention provides a nucleotide molecule encoding a recombinant polypeptide of the present invention.

In another embodiment, the present invention provides a vaccine comprising a nucleotide molecule or recombinant polypeptide of the present invention.

In another embodiment, the present invention provides an immunogenic composition comprising a nucleotide molecule or recombinant polypeptide of the present invention.

In another embodiment, the present invention provides a vector comprising a nucleotide molecule or recombinant polypeptide of the present invention.

In another embodiment, the present invention provides a recombinant form of Listeria comprising a nucleotide molecule of the present invention.

In another embodiment, the present invention provides a vaccine comprising a recombinant form of Listeria of the present invention.

In another embodiment, the present invention provides a culture of a recombinant form of Listeria of the present invention.

In another embodiment, the Listeria of methods and compositions of the present invention is LM. In another embodiment, the Listeria is Listeria ivanovii. In another embodiment, the Listeria is Listeria welshimeri. In another embodiment, the Listeria is Listeria seeligeni. Each type of Listeria represents a separate embodiment of the present invention.

In another embodiment, the present invention provides a recombinant form of Listeria comprising a nucleotide molecule encoding a Her-2 protein or a fragment thereof.

In another embodiment, the present invention provides a method of inducing an anti-Her-2 immune response in a subject, comprising administering to the subject a recombinant polypeptide comprising an N-terminal fragment of a LLO protein fused to a Her-2 protein or fused to a fragment thereof, thereby inducing an anti-Her-2 immune response in a subject.

In one embodiment, the fusion protein of methods and compositions of the present invention comprises an LLO signal sequence from LLO. In another embodiment, the two molecules of the protein (the LLO fragment and the antigen) are joined directly. In another embodiment, the two molecules are joined by a short spacer peptide, consisting of one or more amino acids. In one embodiment, the spacer has no specific biological activity other than to join the proteins or to preserve some minimum distance or other spatial relationship between them. In another embodiment, the constituent amino acids of the spacer are selected to influence some property of the molecule such as the folding, net charge, or hydrophobicity. Each possibility represents a separate embodiment of the present invention.

In another embodiment, the present invention provides a method of inducing an anti-Her-2 immune response in a subject, comprising administering to the subject a recombinant nucleotide encoding a recombinant polypeptide comprising an N-terminal fragment of a LLO protein fused to a Her-2 protein or fused to a fragment thereof, thereby inducing an anti-Her-2 immune response in a subject.

In one embodiment, the step of administering a recombinant polypeptide or recombinant nucleotide of the present invention is performed with a recombinant form of Listeria comprising the recombinant nucleotide or expressing the recombinant polypeptide. In another embodiment, the administering is performed with a different bacterial vector. In another embodiment, the administering is performed with a viral vector. In another embodiment, the administering is performed with a DNA vaccine (e.g. a naked DNA vaccine). In another embodiment, administration of a recombinant polypeptide of the present invention is performed by producing the protein recombinantly, then administering the recombinant protein to a subject. Each possibility represents a separate embodiment of the present invention.

In another embodiment, the immune response elicited by methods and compositions of the present invention comprises a $CD8^+$ T cell mediated response. In another embodiment, the immune response consists primarily of a $CD8^+$ T cell-mediated response. In another embodiment, the only detectable component of the immune response is a $CD8^+$ T cell-mediated response.

In another embodiment, the immune response elicited by methods and compositions of the present invention comprises a $CD4^+$ T cell-mediated response. In another embodiment, the immune response consists primarily of a $CD4^+$ T cell-mediated response. In another embodiment, the only detectable component of the immune response is a $CD4^+$ T cell-mediated response. In another embodiment, the $CD4^+$ T cell-mediated response is accompanied by a measurable antibody response against the antigen. In another embodiment, the $CD4^+$ F cell-mediated response is not accompanied by a measurable antibody response against the antigen.

In another embodiment, the immune response elicited by methods and compositions of the present invention comprises an immune response to a subdominant epitope of the antigen. In another embodiment, the immune response does not comprise an immune response to a subdominant epitope. In another embodiment, the immune response consists primarily of an immune response to a subdominant epitope. In another embodiment, the only measurable component of the immune response is an immune response to a subdominant epitope.

Each type of immune response represents a separate embodiment of the present invention.

Methods of measuring immune responses are well known in the art, and include, e.g. measuring suppression of tumor growth (Examples 2, 5, 8, and 9 herein), flow cytometry (FACS; Example 3), target cell lysis assays (e.g. chromium release assay; Examples 4 and 6), the use of tetramers, and others. Each method represents a separate embodiment of the present invention.

In another embodiment, the present invention provides a method of impeding a growth of a Her-2-expressing tumor in a subject, comprising administering to the subject a recombinant polypeptide comprising an N-terminal fragment of a LLO protein fused to the Her-2 protein or a fragment thereof or a recombinant nucleotide encoding the recombinant polypeptide, whereby the subject mounts an immune response against the Her-2-expressing tumor, thereby impeding a growth of a Her-2-expressing tumor in a subject.

In another embodiment, the present invention provides a method of shrinking a Her-2-expressing tumor in a subject, comprising administering to the subject a recombinant polypeptide comprising an N-terminal fragment of a LLO protein fused to the Her-2 protein or a fragment thereof or a recombinant nucleotide encoding the recombinant polypeptide, whereby the subject mounts an immune response against the Her-2-expressing tumor, thereby impeding a growth of a Her-2-expressing tumor in a subject.

In another embodiment, the present invention provides a method of breaking immune tolerance of a subject to a Her-2-expressing tumor, comprising administering to the subject a recombinant polypeptide comprising an N-terminal fragment of a LLO protein fused to the Her-2 protein or a fragment thereof or a recombinant nucleotide encoding the recombinant polypeptide, whereby the subject mounts an immune response against the Her-2-expressing tumor, thereby breaking immune tolerance of a subject to a Her-2-expressing tumor.

In another embodiment, the present invention provides a method of impeding a growth of a Her-2-expressing tumor in a subject, comprising administering to the subject a recombinant form of Listeria comprising a recombinant nucleotide, the recombinant nucleotide encoding the antigen or a fragment thereof, whereby the subject mounts an immune response against the Her-2-expressing tumor, thereby impeding a growth of a Her-2-expressing tumor in a subject.

In another embodiment, the present invention provides a method of shrinking, a Her-2-expressing tumor in a subject, comprising administering to the subject a recombinant form of Listeria comprising a recombinant nucleotide, the recombinant nucleotide encoding the antigen or a fragment thereof, whereby the subject mounts an immune response against the Her-2-expressing tumor, thereby impeding a growth of a Her-2-expressing tumor in a subject.

In another embodiment, the present invention provides a method of breaking immune tolerance of a subject to a Her-2-expressing tumor, comprising administering to the subject a recombinant form of Listeria comprising a recombinant nucleotide, the recombinant nucleotide encoding the antigen or a fragment thereof, whereby the subject mounts an immune response against the Her-2-expressing tumor, thereby breaking immune tolerance of a subject to a Her-2-expressing tumor.

In another embodiment, the present invention provides a method of improving an antigenicity of a Her-2 protein, comprising the step of fusing a nucleotide encoding an N-terminal fragment of a LLO protein to a nucleotide encoding the Her-2 protein or a fragment thereof to create a recombinant nucleotide, thereby improving an antigenicity of a Her-2 protein.

In another embodiment, a method of the present invention of improving an antigenicity of a Her-2 protein further comprising engineering a Listeria strain to express the recombinant nucleotide. In another embodiment, a different bacteria vector is used to express the recombinant nucleotide. In another embodiment, a viral vector is used to express the recombinant nucleotide. In another embodiment, a DNA vaccine (e.g. a naked DNA vaccine) is used to express the recombinant nucleotide. In another embodiment, administration of the LLO-Her-2 fusion peptide encoded by the nucleotide is performed by producing the protein recombinantly, then administering the recombinant protein to a subject. Each possibility represents a separate embodiment of the present invention.

In another embodiment, the anti-Her-2 immune response elicted by methods and compositions of the present invention comprises a first immune response against an epitope of the Her-2 protein that is present in the fragment and a second immune response to an epitope of the Her-2 protein that is not present in the fragment, as further detailed hereinbelow.

In another embodiment, the present invention provides a method of breaking immune tolerance of a subject to an antigen-expressing tumor, comprising administering to the subject a recombinant polypeptide comprising an N-terminal fragment of a LLO protein fused to a fragment of the antigen or a recombinant nucleotide encoding the recombinant polypeptide, wherein the antigen has one or more dominant $CD8^+$ T cell epitopes and wherein the fragment does not contain any of the dominant $CD8^+$ T cell epitopes, whereby the subject mounts an immune response against the antigen-expressing tumor, thereby breaking immune tolerance of a subject to an antigen-expressing tumor.

In another embodiment, the present invention provides a method of breaking immune tolerance of a subject to an antigen-expressing tumor, comprising administering to the subject a recombinant form of Listeria comprising a recombinant nucleotide, the recombinant nucleotide encoding a fragment of the antigen, wherein the antigen has one or more dominant $CD8^+$ T cell epitopes and wherein the fragment does not contain any of the dominant $CD8^+$ T cell epitopes, whereby the subject mounts an immune response against the antigen-expressing tumor, thereby breaking immune tolerance of a subject to an antigen-expressing tumor.

In another embodiment, the present invention provides a method of identifying a $CD8^+$ T cell epitope of an antigen, comprising the steps of (a) fusing a nucleotide molecule encoding the antigen to a nucleotide molecule encoding an N-terminal fragment of a LLO protein, thereby creating a recombinant nucleotide an LLO-antigen fusion protein; (b) administering the LLO-antigen fusion to a subject; (c) isolating a $CD8^+$ T cell from the subject; and (d) determining the epitope recognized by the $CD8^+$ T cell; thereby identifying a $CD8^+$ T cell epitope of an antigen. In one embodiment, the $CD8^+$ T cell epitope is a subdominant epitope. Each possibility represents a separate embodiment of the present invention.

"Dominant $CD8^+$ T cell epitope," in one embodiment, refers to an epitope that is recognized by over 30% of the antigen-specific $CD8^+$ T cells that are elicited by vaccination, infection, or a malignant growth with a protein or a pathogen or cancer cell containing the protein. In another embodiment, the term refers to an epitope recognized by over 35% of the antigen-specific $CD8^+$ T cells that are elicited thereby. In another embodiment, the term refers to an epitope recognized by over 40% of the antigen-specific $CD8^+$ T cells. In another embodiment, the term refers to an epitope recognized by over 45% of the antigen-specific $CD8^+$ T cells. In another embodiment, the term refers to an epitope recognized by over 50% of the antigen-specific $CD8^+$ T cells. In another embodiment, the term refers to an epitope recognized by over 55% of the antigen-specific $CD8^+$ T cells. In another embodiment, the term refers to an epitope recognized by over 60% of the antigen-specific $CD8^+$ T cells. In another embodiment, the term refers to an epitope recognized by over 65% of the antigen-specific $CD8^+$ T cells. In another embodiment, the term refers to an epitope recognized by over 70% of the antigen-specific $CD8^+$ T cells. In another embodiment, the term refers to an epitope recognized by over 75% of the antigen-specific $CD8^+$ T cells. In another embodiment, the term refers to an epitope recognized by over 80% of the antigen-specific $CD8^+$ T cells. In another embodiment, the term refers to an epitope recognized by over 85% of the antigen-specific $CD8^+$ T cells. In another embodiment, the term refers to an epitope recognized by over 90% of the antigen-specific $CD8^+$ T cells. In another embodiment, the term refers to an epitope recognized by over 95% of the antigen-specific $CD8^+$ T cells. In another embodiment, the term refers to an epitope recognized by over 96% of the antigen-specific $CD8^+$ T cells. In another embodiment, the term refers to an epitope recognized by over 97% of the antigen-specific $CD8^+$ T cells. In another, embodiment, the term refers to an epitope recognized by over 98% of the antigen specific $CD8^+$ T cells.

"Subdominant CD8+ T cell epitope," in one embodiment, refers to an epitope recognized by fewer than 30% of the antigen-specific CD8+ T cells that are elicited by vaccination, infection, or a malignant growth with a protein or a pathogen or cancer cell containing the protein. In another embodiment, the term refers to an epitope recognized by fewer than 28% of the antigen-specific CD8+ T cells. In another embodiment, the term refers to an epitope recognized by over 26% of the antigen-specific CD8+ T cells. In another embodiment, the term refers to an epitope recognized by fewer than 24% of the antigen-specific CD8+ T cells. In another embodiment, the term refers to an epitope recognized by over 22% of the antigen-specific CD8+ T cells. In another embodiment, the term refers to an epitope recognized by fewer than 20% of the antigen-specific CD8+ T cells. In another embodiment, the term refers to an epitope recognized by over 18% of the antigen-specific CD8+ T cells. In another embodiment, the term refers to an epitope recognized by fewer than 16% of the antigen-specific CD8+ T cells. In another embodiment, the term refers to an epitope recognized by over 14% of the antigen-specific CD8+ T cells. In another embodiment, the term refers to an epitope recognized by over 12% of the antigen-specific CD8+ T cells. In another embodiment, the term refers to an epitope recognized by fewer than 10% of the antigen-specific CD8+ T cells. In another embodiment, the term refers to an epitope recognized by over 8% of the antigen-specific CD8+ T cells. In another embodiment, the term refers to an epitope recognized by fewer than 6% of the antigen-specific CD8+ T cells. In another embodiment, the term refers to an epitope recognized by fewer than 5% of the antigen-specific CD8+ T cells. In another embodiment, the term refers to an epitope recognized by over 4% of the antigen-specific CD8+ T cells. In another embodiment, the term refers to an epitope recognized by fewer than 3% of the antigen-specific CD8+ T cells. In another embodiment, the term refers to an epitope recognized by fewer than 2% of the antigen-specific CD8+ T cells. In another embodiment, the term refers to an epitope recognized by fewer than 1% of the antigen-specific CD8+ T cells. In another embodiment, the term refers to an epitope recognized by fewer than 0.5% of the antigen-specific CD8+ T cells.

In another embodiment, the "subdominant epitope" refers to an epitope not revealed by other methods of vaccination. For example, Ercolini et al (J Immunol 2003, 170: 4273-4280) vaccinated subjects with both neu-expressing tumor cells transfected with GM-CSF and recombinant vaccinia expressing Her-2, yet found a single dominant epitope, AA 420-429. By contrast, use of the ΔLLO-Her-2 fusions in the experiments described herein revealed additional epitopes in addition to AA 420-429. Delivering the fusions with recombinant LM reveals yet more epitopes.

In another embodiment, the dominant epitope or subdominant epitope is dominant or subdominant, respectively, in the subject being treated. In another embodiment, the dominant epitope or subdominant epitope is dominant or subdominant in a population being treated.

Each type of the dominant epitope and subdominant epitope represents a separate embodiment of the present invention.

In another embodiment, the present invention provides a method of breaking an immune tolerance of a subject to an antigen-expressing tumor, wherein the antigen is expressed at a detectable level on a non-tumor cell of the subject, comprising administering to the subject a recombinant polypeptide comprising an N-terminal fragment of a LLO protein fused to the antigen or fused to a fragment thereof or a recombinant nucleotide encoding the recombinant polypeptide, whereby the subject mounts an immune response against the antigen-expressing tumor, thereby breaking an immune tolerance of a subject to an antigen-expressing tumor.

In another embodiment, the present invention provides a method of breaking an immune tolerance of a subject to an antigen-expressing tumor, wherein the antigen is expressed at a detectable level on a non-tumor cell of the subject, comprising administering to the subject a recombinant form of *Listeria* comprising a recombinant nucleotide, the recombinant nucleotide encoding the antigen, whereby the subject mounts an immune response against the antigen-expressing tumor, thereby breaking an immune tolerance of a subject to an antigen-expressing tumor.

"Detectable level" refers, in one embodiment, to a level detectable by a standard assay. In one embodiment, the assay is an immunological assay. In one embodiment, the assay is enzyme-linked immunoassay (ELISA). In another embodiment, the assay is Western blot (Example 1). In another embodiment, the assay is FACS (Example 3). In another embodiment, a detectable level is determined relative to the background level of a particular assay. Methods for performing each of these techniques are well known to those skilled in the art, and each technique represents a separate embodiment of the present invention.

The antigen in methods and compositions of the present invention is, in one embodiment, expressed at a detectable level on a non-tumor cell of the subject. In another embodiment, the antigen is expressed at a detectable level on at least a certain percentage (e.g. 0.01%, 0.03%, 0.1%, 0.3%, 1%, 2%, 3%, or 5%) of non-tumor cells of the subject. In one embodiment, "non-tumor cell" refers to a cell outside the body of the tumor. In another embodiment, "non-tumor cell" refers to a non-malignant cell. In another embodiment, "non-tumor cell" refers to a non-transformed cell. In another embodiment, the non-tumor cell is a somatic cell. In another embodiment, the non-tumor cell is a germ cell. Each possibility represents a separate embodiment of the present invention.

In another embodiment, the present invention provides a method of inducing a CD8+ T cell-mediated immune response in a subject against a subdominant CD8+ T cell epitope of an antigen, comprising the steps of (a) fusing a nucleotide molecule encoding the antigen or a fragment thereof to a nucleotide molecule encoding an N-terminal fragment of a LLO protein, thereby creating a recombinant nucleotide encoding an LLO-antigen fusion protein; and (b) administering the recombinant nucleotide or the LLO-antigen fusion to the subject; thereby inducing a CD8+ T cell-mediated immune response against a subdominant CD8+ T cell epitope of an antigen.

In another embodiment, the present invention provides a method of inducing an immune response to a first epitope of an antigen, in an animal expressing the antigen on a tumor or an infectious agent, by vaccinating an animal with a recombinant *Listeria* expressing a fragment of the antigen, wherein the fragment used in vaccination does not include the first epitope. Rather, the fragment contains a second epitope of the same antigen, against which the animal mounts an immune response. A continuing immune response against the tumor or infectious agent results in recognition of the first epitope by epitope spreading, as shown herein.

In another embodiment, the present invention provides a method of inducing an immune response to a first epitope of an antigen, in an animal expressing the antigen on a tumor or an infectious agent, by vaccinating an animal with a vaccine comprising LLO fused to a fragment of the antigen, wherein the fragment used in vaccination does not include the first epitope. Rather, the fragment contains a second epitope, against which the animal mounts an immune response. A continuing immune response against the tumor or infectious agent results in recognition of the first epitope by epitope spreading, as shown herein.

In one embodiment, the immune response to the first epitope is initiated at least 2 weeks following the step of administering. In another embodiment, the immune response to the first epitope is initiated at least 2 weeks following conclusion of the step of administering. In another embodiment, the time frame is 1 week. In another embodiment, the time frame is 10 days. In another embodiment, the time frame is 17 days. In another embodiment, the time frame is 3 weeks. In another embodiment, the time frame is 4 weeks. Each possibility represents a separate embodiment of the present invention.

As provided herein, the results of the present invention further demonstrate that vaccination with recombinant antigen-expressing LM induces epitope spreading. In another embodiment, vaccination with LLO-antigen fusions, even outside the context of LM, induces epitope spreading as well. Each possibility represents a separate embodiment of the present invention.

In another embodiment, the present invention provides a method of impeding a growth of an antigen-expressing tumor in a subject, comprising administering to the subject a recombinant polypeptide comprising an N-terminal fragment of a LLO protein fused to a fragment of the antigen or a recombinant nucleotide encoding the recombinant polypeptide, wherein the antigen has one or more dominant $CD8^+$ T cell epitopes and wherein the fragment does not contain any of the dominant $CD8^+$ T cell epitopes, whereby the subject mounts an immune response against the antigen-expressing tumor, thereby impeding a growth of an antigen-expressing tumor in a subject.

In another embodiment, the present invention provides a method of impeding a growth of an antigen-expressing tumor in a subject, comprising administering to the subject a recombinant form of *Listeria* comprising a recombinant nucleotide, the recombinant nucleotide encoding a fragment of the antigen, wherein the antigen has one or more dominant $CD8^+$ T cell epitopes and wherein the fragment does not contain any of the dominant $CD8^+$ T cell epitopes, whereby the subject mounts an immune response against the antigen-expressing tumor, thereby impeding a growth of an antigen-expressing tumor in a subject.

In another embodiment, the antigen of methods of the present invention is a Her-2 protein. In another embodiment, the antigen is a HPV-16 E7 protein. In another embodiment, the antigen is bcr/abl. In another embodiment, the antigen is HPV E6 in another embodiment, the antigen is MZ2-E. In another embodiment, the antigen is MAGE-1. In another embodiment, the antigen is MUC-1. In another embodiment, the antigen is NY/ESO-1. In another embodiment, the antigen is Wilms tumor antigen. In another embodiment, the antigen is telomerase. In another embodiment, the antigen is Proteinase 3'. In another embodiment, the antigen is Tyrosinase related protein 2. In another embodiment, the antigen is HIV-1 Gag protein. In another embodiment, the antigen is SIV-1 Gag protein. In another embodiment, the antigen is HIV-1 Env protein. In another embodiment, the antigen is any other tumor antigen known in the art. In another embodiment, the antigen is any other infectious disease antigen known in the art. Each possibility represents a separate embodiment of the present invention.

In other embodiments, the antigen is derived from a tumor or an infectious organism, including, but not limited to fungal pathogens, bacteria, parasites, helminths, viruses, and the like. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Muc1, or pSA.

In other embodiments, the antigen is an antigen associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever; the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthriti des, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthienia gravis, Lambert-Eaton syndrome, sclera, episciera, uveitis, chronic m ucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutiopenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

In other embodiments, the antigen is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers: the HPV 16/18 antigens associated with cervical cancers, KLH antigen associated with breast carcinoma, CEA (carcinoembryonic antigen) associated with colorectal cancer, gp100, a MARTI antigen associated with melanoma, or the PSA antigen associated with prostate cancer.

The skilled artisan will appreciate that any of the above antigens can be fused to an LLO fragment. Each of the above antigens represents a separate embodiment of the present invention.

In another embodiment, the present invention provides a method for, suppressing formation of tumors in a host, comprising administering to the host a composition of the present invention, thereby suppressing formation of tumors in a host.

In another embodiment, the present invention provides a method for inducing formation of tumor-infiltrating $CD8^+$ T cells in a host having cancer, comprising administering to the host a composition of the present invention, thereby inducing formation of tumor-infiltrating CD8$^+$ T cells in a host having cancer.

In another embodiment, the present invention provides a method for inducing formation of cytotoxic T cells in a host having cancer, comprising administering to the host a composition of the present invention, thereby inducing formation of cytotoxic T cells in a host having cancer.

In another embodiment, the present invention provides a method of reducing an incidence of cancer, comprising administering a composition of the present invention. In another embodiment, the present invention provides a method of ameliorating cancer, comprising administering a composition of the present invention. Each possibility represents a separate embodiment of the present invention.

In one embodiment of methods of the present invention, the composition is administered to the cells of the subject ex vivo, in another embodiment, the composition is administered to the cells of a donor ex vivo, in another embodiment, the composition is administered to the cells of a donor in vivo, then is transferred to the subject. Each possibility represents a separate embodiment of the present invention.

In one embodiment, the cancer treated by a method of the present invention is breast cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. Each possibility represents a separate embodiment of the present invention.

In another embodiment of the methods of the present invention, the subject mounts an immune response against the antigen-expressing tumor or target antigen, thereby mediating the anti-tumor effects.

In another embodiment, the present invention provides an immunogenic composition for treating cancer, the composition comprising a fusion of a truncated LLO to a Her-2 protein. In another embodiment, the immunogenic composition further comprises a *Listeria* strain expressing the fusion. Each possibility represents a separate embodiment of the present invention.

In another embodiment, the present invention provides an immunogenic composition for treating cancer, the composition comprising a *Listeria* strain expressing a Her-2 protein.

In one embodiment, a treatment protocol of the present invention is therapeutic. In another embodiment, the protocol is prophylactic. In another embodiment, the vaccines of the present invention are used to protect people at risk for cancer because of familial genetics or other circumstances that predispose them to certain types of cancer, e.g., cervical cancer in women whose husbands have papilloma virus. In another embodiment, the vaccines are used as a cancer immunotherapy after debulking of tumor growth by surgery, conventional chemotherapy or radiation treatment. Following such treatments, the vaccines of the present invention are administered so that the CTL response to the tumor antigen of the vaccine, destroys remaining metastases and prolongs remission from the cancer. In another embodiment, vaccines of the present invention are used to effect the growth of previously established tumors and to kill existing tumor cells. Each possibility represents a separate embodiment of the present invention.

In other embodiments, the vaccines and immunogenic compositions utilized in any of the methods described above have any of the characteristics of vaccines and immunogenic compositions of the present invention. Each characteristic represents a separate embodiment of the present invention.

Various embodiments of dosage ranges are contemplated by this invention. In one embodiment, in the case of vaccine vectors, the dosage is in the range of 0.001 $LD_{50}$/dose. In another embodiment, the dosage is 0.002 $LD_{50}$/dose. In another embodiment the dosage is 0.003 $LD_{50}$/dose. In another embodiment the dosage is 0.004 $LD_{50}$/dose. In another embodiment the dosage is 0.006 $LD_{50}$/dose. In another embodiment the dosage is 0008 $LD_{50}$/dose. In another embodiment the dosage is 0.01 $LD_{50}$/dose. In another embodiment the dosage is 0.02 $LD_{50}$/dose. In another embodiment the dosage is 0.03 $LD_{50}$/dose. In one embodiment, the dosage is 0.04 $LD_{50}$/dose. In another embodiment, the dosage is 0.06 $LD_{50}$/dose. In another embodiment, the dosage 0.08 $LD_{50}$/dose. In another embodiment, the dosage is 0.1 $LD_{50}$/dose. In another embodiment, the dosage is 0.15 $LD_{50}$/dose. In another embodiment, the dosage is 0.2 $LD_{50}$/dose. In another embodiment, the dosage is 0.25 $LD_{50}$/dose. In another embodiment, the dosage in 0.3 $LD_{50}$/dose. In another embodiment, the dosage is 0.4 $LD_{50}$/dose. In another embodiment, the dosage is 0.5 $LD_{50}$/dose.

In another embodiment, the dosage is $10^7$ bacteria/dose. In another embodiment, the dosage is $1.5\times10^7$ bacteria/dose. In another embodiment, the dosage is $2\times10^7$ bacteria/dose. In another embodiment, the dosage is $3\times10^7$ bacteria/dose. In another embodiment, the dosage is $4\times10^7$ bacteria/dose. In another embodiment, the dosage is $6\times10^7$ bacteria/dose. In another embodiment, the dosage is $8\times10^7$ bacteria/dose. In another embodiment, the dosage is $1\times10^8$ bacteria/dose. In another embodiment, the dosage is $1.5\times10^8$ bacteria/dose. In another embodiment, the dosage is $2\times10^8$ bacteria/dose. In another embodiment, the dosage is $3\times10^8$ bacteria/dose. In another embodiment, the dosage is $4\times10^8$ bacteria/dose. In another embodiment, the dosage is $6\times10^8$ bacteria/dose. In another embodiment, the dosage is $8\times10^8$ bacteria/dose. In another embodiment, the dosage is $1\times10^9$ bacteria/dose. In another embodiment, the dosage is $1.5\times10^9$ bacteria/dose. In another embodiment, the dosage is $2\times10^9$ bacteria/dose. In another embodiment, the dosage is $3\times10^9$ bacteria/dose. In another embodiment, the dosage is $5\times10^9$ bacteria/dose. In another embodiment, the dosage is $6\times10^9$ bacteria/dose. In another embodiment, the dosage is $8\times10^9$ bacteria/dose. In another embodiment, the dosage is $1\times10^{10}$ bacteria/dose. In another embodiment, the dosage is $1.5\times10^{10}$ bacteria/dose. In another embodiment, the dosage is $2\times10^{10}$ bacteria/dose. In another embodiment, the dosage is $3\times10^{10}$ bacteria/dose. In another embodiment, the dosage is $5\times10^{10}$ bacteria/dose. In another embodiment, the dosage is $6\times10^{10}$ bacteria/dose. In another embodiment, the dosage is $8\times10^{10}$ bacteria/dose. In another embodiment, the dosage is $8\times10^9$ bacteria/dose. In another embodiment, the dosage is $1\times10^{11}$ bacteria/dose. In another embodiment, the dosage is $1.5\times10^{11}$ bacteria/dose. In another embodiment, the dosage is $2\times10^{11}$ bacteria/dose. In another embodiment, the dosage is $3\times10^{11}$ bacteria/dose. In another embodiment, the dosage is $5\times10^{11}$ bacteria/dose. In another embodiment, the dosage is $6\times10^{11}$ bacteria/dose. In another embodiment, the dosage is $8\times10^{11}$ bacteria/dose. Each possibility represents a separate embodiment of the present invention.

In another embodiment, in the case of recombinant polypeptides, the dosage is 1 mg/dose. In another embodiment, the dosage is 1.5 mg/dose. In another embodiment, the dosage is 2 mg/dose. In another embodiment, the dosage is 3 mg/dose. In another embodiment, the dosage is 4 mg/dose. In another embodiment, the dosage is 6 mg/dose. In another embodiment, the dosage is 8 mg/dose. In another embodiment, the dosage is 10 mg/dose. In another embodiment, the dosage is 15 mg/dose. In another embodiment, the dosage is 20 mg/dose. In another embodiment, the dosage is 30 mg/dose. In another embodiment, the dosage is 40 mg/dose. In another embodiment, the dosage is 60 mg/dose. In another embodiment, the dosage is 80 mg/dose. In another embodiment, the dosage is 100 mg/dose. In another embodiment, the dosage is 150 mg/dose. In another embodiment, the dosage is 200 mg/dose. In another embodiment, the dosage is 300 mg/dose. In another embodiment, the dosage is 400 mg/dose. In another embodiment, the dosage is 600 mg/dose. In another embodiment, the dosage is 800 mg/dose. In another embodiment, the dosage is 1000 mg/dose.

Each of the above doses represents a separate embodiment of the present invention.

In one embodiment, a vaccine or immunogenic composition of the present invention is administered alone to a subject. In another embodiment, the vaccine or immunogenic composition is administered together with another cancer therapy. Each possibility represents a separate embodiment of the present invention.

The recombinant *Listeria* of methods and compositions of the present invention is, in one embodiment, stably transformed with a construct encoding an antigen or an LLO-antigen fusion. In one embodiment, the construct contains a polylinker to facilitate further subcloning. Several techniques for producing recombinant *Listeria* are known.

In one embodiment, the construct or heterologous gene is integrated into the *Listerial* chromosome using homologous recombination. Techniques for homologous recombination are well known in the art, and are described, for example, in Baloglu S, Boyle S M, et al, Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7; and Jiang L L, Song H H, et al, Characterization of a mutant *Listeria monocytogenes* strain expressing green fluorescent protein. Acta Biochim Biophys Sin (Shanghai) 2005, 37(1): 19-24. In another embodiment, homologous recombination is performed as described in U.S. Pat. No. 6,855,320. In this case, a recombinant LM strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants. Each technique represents a separate embodiment of the present invention.

In another embodiment, the construct or heterologous gene is integrated into the *Listerial* chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or heterologous gene is integrated into the *Listerial* chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg rRNA gene). In another embodiment, endogenous prophages are cured from the attachment site utilized prior to integration of the construct or heterologous gene. In another embodiment, this method results in single-copy integrants. Each possibility represents a separate embodiment of the present invention.

In another embodiment, the construct is carried by the *Listeria* strain on a plasmid. Cloning of the gene into a prfA-containing vector and using this plasmid to complement a prfA(–) *Listeria* mutant has been used to construct DP-L2028. DP-L2028 is the influenza NP expressing strain used in the tumor protection experiments. An LM vector that expresses an E7 fusion protein has also been constructed via this technique. Lm-GG/E7 was made by complementing a prfA-deletion mutant with a plasmid containing a copy of the prfA gene and a copy of the E7 gene fused to a form of the LLO (hly) gene truncated to eliminate the hemolytic activity of the enzyme, as described in U.S. Pat. No. 6,565,852. Functional LLO is maintained by the organism via the endogenous chromosomal copy of hly.

In other embodiments, one of several approaches is taken to express the tumor antigen in *Listeria*. In one embodiment, a fusion protein of the selected tumor antigen and a *Listerial* protein, such as PI-PLC, or a construct encoding same, is generated. In another embodiment, a signal sequence, of a secreted *Listerial* protein such as hemolysin or phospholipases, is fused to the antigen-encoding gene.

In another embodiment, the construct is contained in the *Listeria* strain in an episomal fashion. In another embodiment, the foreign antigen is expressed from a vector harbored by the recombinant *Listeria* strain. Each possibility represents a separate embodiment of the present invention.

In other embodiments, one of various promoters is used to express the antigen or fusion protein containing same. In one embodiment, an LM promoter is used, eg, promoters for the genes hly, actA, pica, plcB and mpl, which encode the *Listerial* proteins hemolysin, act A, phosphiotidylinositol-specific phospholipase, phospholipase C, and metal loprotease, respectively. Each possibility represents a separate embodiment of the present invention.

Panels of antigens are, in one embodiment, useful in immunotherapy against cancer to compensate for the fact that antigen-loss variants of the tumors can grow out under immune system pressure (Zhang et al, Clin Cancer Res 1998 4: 2669; Kawashima et al, Hum Immunol 1998 59: 1). Thus, in another embodiment, methods and compositions of the present invention comprise a cocktail of recombinant fusion proteins, each fusion protein comprising a different tumor associated antigen fused to a truncated LLO, or a cocktail of recombinant LM strains, each expressing a different tumor associated antigen. Each possibility represents a separate embodiment of the present invention.

In another embodiment, methods and compositions of the present invention utilize a homologue of a Her-2 or LLO sequence of the present invention (e.g. SEQ ID No: 33, 34, 40, 41, 43, and 44). The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

Homology is, in one embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 33, 34, 40, 41, 43, and 44 of greater than 70%. In another embodiment, "homology" refers to identity to a sequence selected from SEQ ID No: 33, 34, 40, 41, 43, and 44 of greater than 72%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%, in another embodiment, the identity is greater than 92%. In another embodiment, the identity is greater than 93%. In another embodiment, the identity is greater than 95%. In another embodiment the identity is greater than 96%. In another embodiment, the identity is greater than 97%. In another embodiment, the identity is greater than 98%. In another embodiment, the identity is greater than 99%. In another embodiment, the identity is 100%. Each possibility represents a separate embodiment of the present invention.

In another embodiment, homology is determined is via determination of candidate sequence hybridization, methods of which are well described in the art (See, for example, "Nucleic Acid Hybridization" Hames, B. D., and Higgins S. J., Eds, (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

In one embodiment of the present invention, "nucleic acids" refers to a string of at least two base-sugar-phosphate combinations. The term includes, in one embodiment, DNA and RNA "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

The terms "contacting" or "administering," in one embodiment, refer to directly contacting the cancer cell or tumor with a composition of the present invention. In another embodiment, the terms refer to indirectly contacting the cancer cell or tumor with a composition of the present invention. In another embodiment, methods of the present invention include methods in which the subject is contacted with a composition of the present invention after which the composition is brought in contact with the cancer cell or tumor by diffusion or any other active transport or passive transport process known in the art by which compounds circulate within the body. Each possibility represents a separate embodiment of the present invention.

Pharmaceutical Compositions

The pharmaceutical compositions containing vaccines and compositions of the present invention can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the vaccines or compositions are administered by intravenous, intra-arterial, or intramuscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intramuscular administration.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease. The terms "reducing", "suppressing" and "inhibiting" refer in another embodiment to lessening or decreasing. Each possibility represents a separate embodiment of the present invention.

EXPERIMENTAL DETAILS SECTION

Example 1

Generation of L. Monocytogenes Strains that Secrete LLO Fragments Fused to Her-2 Fragments Bacteria Bacteria were grown in brain heart infusion medium (BD, Sparks, Md.) with 50 μg/ml chloramphenicol and were frozen in 1 ml aliquots at −80° C.

Western Blots

ΔLLO-Her-2 expressing strains were grown overnight at 37° C. in Luria-Bertani (LB) medium with 50 microgram per milliliter (μg/ml) chloramphenicol. Supernatants were TCA precipitated and resuspended in 1×LDS sample buffer (Invitrogen, San Diego, Calif.). 15 microliter (μl) of each sample was loaded on a 4-12% Bis-Tris SDS-PAGE gel (Invitrogen, San Diego, Calif.). Gels were transferred to a Immobilon-P polyvinylidene fluoride membrane (Millipore, Billerica, Mass.) and blotted with a polyclonal rabbit serum recognizing residues 1-30 of LLO, followed by HRP-conjugated anti-rabbit antibody (Amersham Pharmacia Biotech, UK).

Statistical Analyses

Statistical analyses were performed using Student's t-test throughout the Examples.

Results

Five recombinant LM strains were constructed that express and secrete overlapping fragments of the rat Her-2 gene fused to the N-terminal portion of *L. monocytogenes* LLO protein (FIG. 2A). The signal sequence and transmembrane domain of Her-2 were not included among the fragments due to their hydrophobicity and the inability of LM to secrete extremely hydrophobic domains. Secretion of each Her-2 fragment was confirmed by Western blot (FIG. 2B). Molecular weights of the proteins Lm-ΔLLO-EC1 Lm-ΔLLO-EC2 Lm-ΔLLO-EC3, Lm-ΔLLO-IC1, and Lm-ΔLLO-IC2 were 83, 70, 68, 92.5, and 74-kDa (kilodalton), respectively. The strains were attenuated relative to the wild-type 10403S strain, exhibiting virulences comparable to Lm-ΔLLO-E7; namely $1 \times 10^8$, $5 \times 10^8$, $1 \times 10^9$, $1 \times 10^8$, and $1 \times 10^8$ colony forming units (CFU), respectively.

Example 2

Vaccination with LLO-Her-2 Constructs Halts and Reverses Growth of Her-2-Expressing Tumors Materials and Experimental Methods Mice Six to eight week old female FVB/N mice were purchased from Charles River Laboratories (Wilmington, Mass.).

Cell Lines

The FVB/N syngeneic NT-2 tumor cell line, derived from a spontaneously occurring mammary tumor in an FVB/N Her-2 transgenic mouse (Reilly R T et al, Canc Res 60: 3569, 2000), constitutively expresses low levels of rat Her-2 and is tumorigenic in wild type syngeneic mice. NT-2 cells were grown in RPMI 1640 medium with 20% FCS, 10.2 mM HEPES, 2 millimolar (mM) L-glutamine, 100 micromolar (μM) nonessential amino acids, 1 mM sodium pyruvate, 50 U (units)/ml penicillin G, 50 μg/ml streptomycin, 20 μg/ml insulin, and 2 μg/ml gentamycin at 37° C. with 5% $CO_2$.

Experimental Setup 6-8 week-old FVB/N mice (n=8) were injected subcutaneously in the right flank with $2 \times 10^6$ NT-2 tumor-cells in 200 μl PBS. Seven days post-tumor inoculation, palpable tumors of 4-5 mm were observed, after which mice were injected intraperitoneally with recombinant LM or PBS on days 7, 14, and 21. The shortest and longest surface diameters of the tumors were measured every 2 days with calipers. Mice were sacrificed if they reached a point at which mean tumor diameter reached 20 mm.

Results

LM strains expressing ΔLLO-Her-2 fusions were compared to PBS and Lm-ΔLLO-E7 (negative controls) for their ability to induce immunity against and reduction of tumors composed of the rat Her-2 expressing tumor line, NT-2. FVB/N mice were injected with NT-2 tumors, then, on days 7, 14, and 21 following tumor inoculation, were administered 0.1 $LD_{50}$ of recombinant LM or PBS. Injection of LM expressing the ΔLLO-Her-2 fusions halted tumor growth after the first injection (FIGS. 2A and B); the cessation in tumor growth continued through the last timepoint, more than nine weeks after the last Her-2 vaccination. Moreover, a complete regression of tumors was subsequently observed in three out of 8 of the Lm-ΔLLO-EC2 and Lm-ΔLLO-EC3 mice and 1 of 8 of the Lm-ΔLLO-EC1 and Lm-ΔLLO-IC1 mice. Additional mice from all five of the ΔLLO-Her-2 groups exhibited a reduction in tumor size. As expected, tumors grew continually in mice injected with PBS and Lm-ΔLLO-E7.

These findings demonstrate that fusions of a LLO fragment to Her-2 are capable of eliciting immunity against Her-2-expressing tumors. These findings further indicate that the elicited immunity (a) is strong enough to induces the complete regression of greater than 75% of established Her-2-expressing tumors; and (b) lasts over the course of over at least several months.

Example 3

Immune Responses Induced by the Lm-LLO-Her-2 Vaccine Include CD8+ T Cells

Materials and Experimental Methods

CD8+ T Cell Depletion

CD8+ T cells were depleted by injection with 0.5 mg of the anti-CD8 antibody 2.43 (Sarmiento M et al, J Immunol 125 (6): 2665-72, 1980) on days 6, 7, 8, 11, 14, 17, 20, and 23 post-tumor injection. CD8+ T cell populations were reduced by greater than 95% as measured by flow cytometric analysis on day 24.

Flow Cytometric Analysis

Three color flow cytometry for CD8 (53-6.7, FITC conjugated), CD62 ligand (Mel-14, APC conjugated) (BD Biosciences Pharmingen, San Diego, Calif.), and Her-2H-$2^q$ tetramer (PE conjugated) was performed using a FACSCalibur flow cytometer with CellQuest software (Becton Dickinson, San Jose, Calif.). Tetramers, provided by the NIAID Tetramer Core Facility of Emory University and the NIH AIDS Research and Reference Reagent Program, were loaded with an H-$2^q$ specific PDSLRDLSVF peptide. Splenocytes were stained at room temperature (rt) with the tetramer for one hour (hr) at 1:200 dilution, then at 4° C. with anti-CD8 and anti-CD62L antibodies for 30 minutes (min). The CD8+, CD62L$^{low}$ subset was selected ("gated on"), and percentages of tetramer+ cells were compared using FlowJo software (Tree Star, Inc, Ashland, Oreg.).

Results

Figure 3A:
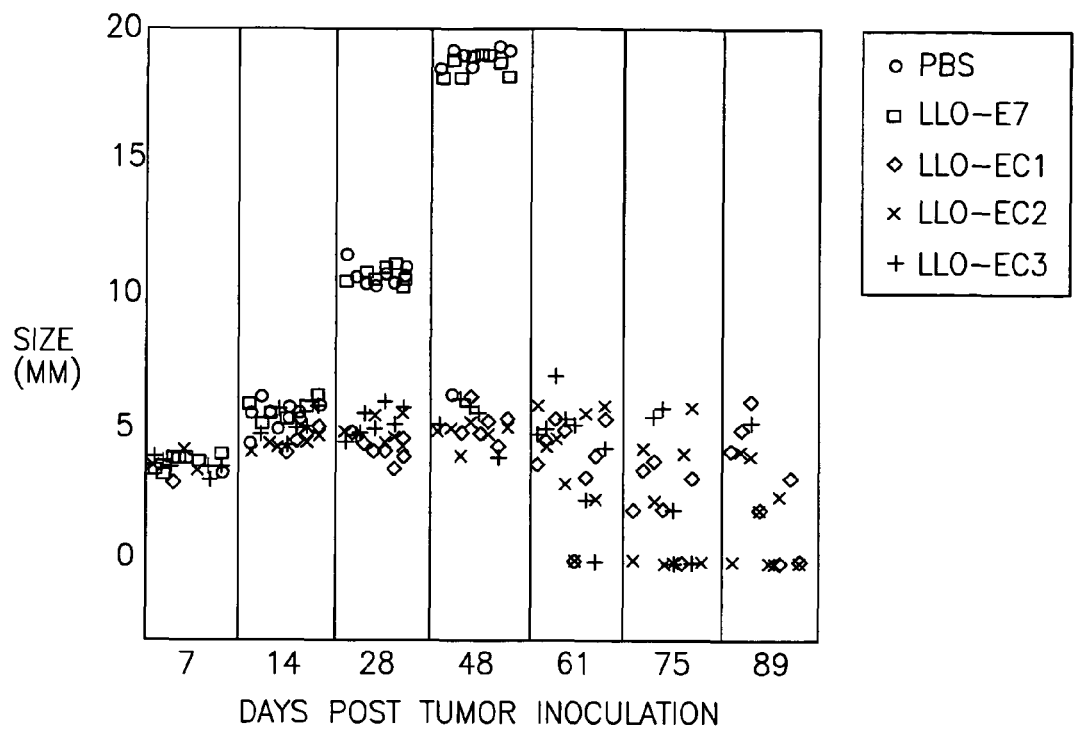
FIG. 3. Lm-ΔLLO-Her-2 vaccines each induce a halt in tumor growth of established NT-2 tumors. Each data point represents the average of shortest and longest surface tumor diameter of one mouse at a given time point. Mice were sacrificed when the average tumor diameter reached 2.0 cm; tumor measurements are only shown for the surviving mice at a given time point. Representative figures of two experiments are shown. (A) Lm-ΔLLO-EC1, Lm-ΔLLO-EC2, and Lm-ΔLLO-EC3; (B) Lm-ΔLLO-IC1, and Lm-ΔLLO-IC2.
Figure 3B:
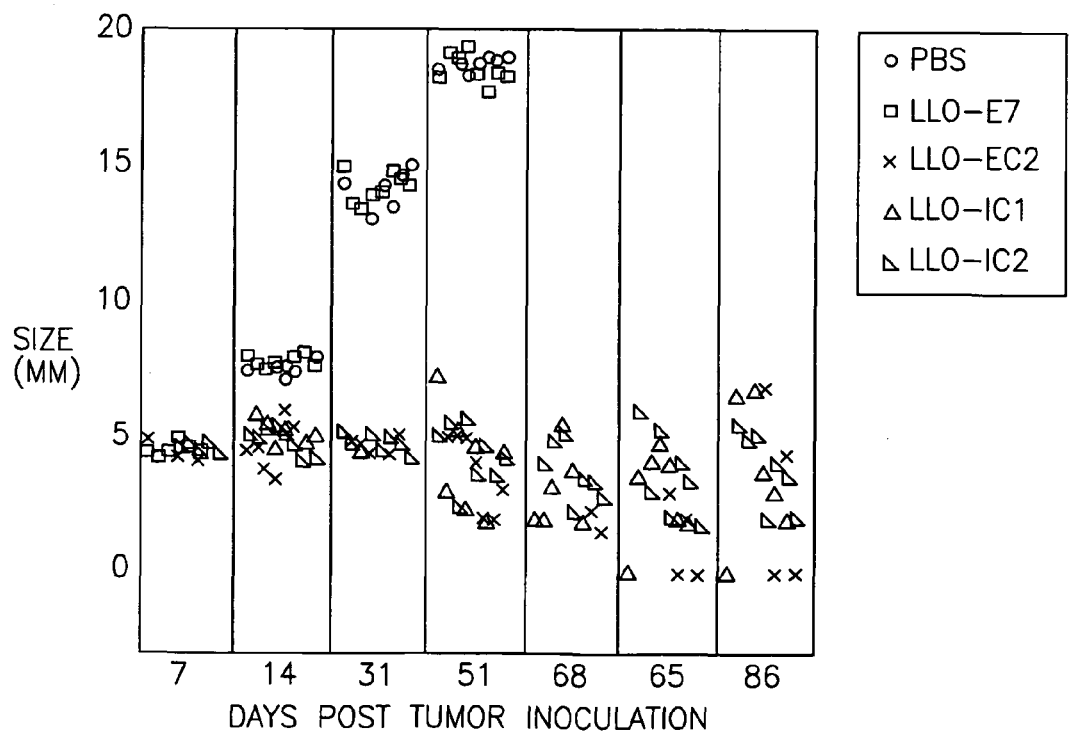
Figure 4A:
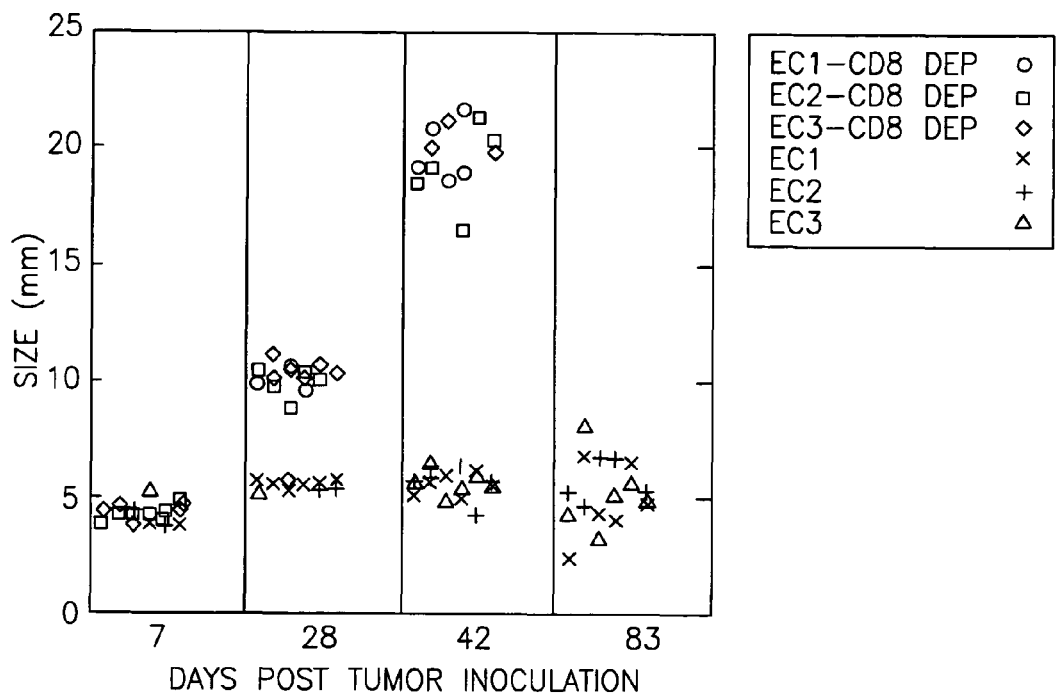
FIG. 4. CD8+ T cells participate in Lm-LLO-Her-2 induced tumor stasis. Tumor measurements are shown only for the surviving mice at a given time point. (A) Lm-ΔLLO-EC1, Lm-ΔLLO-EC2, and Lm-ΔLLO-EC3 both depleted and undepleted for CD8+ T cells. (B) Lm-ΔLLO-IC1 and Lm-ΔLLO-IC2 both depleted and undepleted for CD8+ T cells.
Figure 4B:
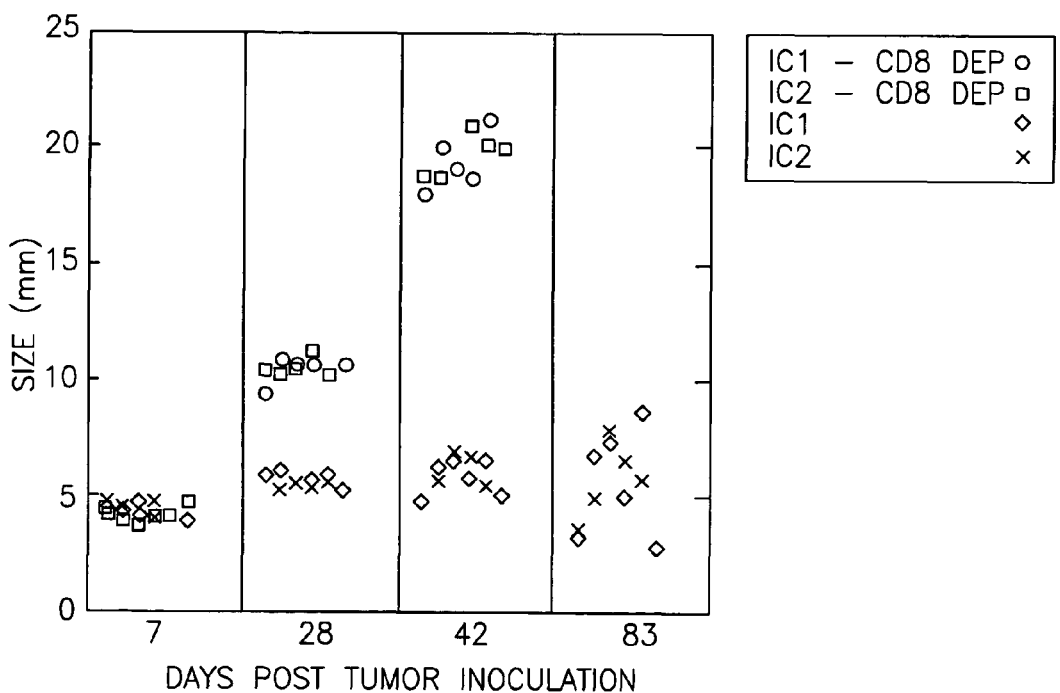

In order to determine the type of T cells that were mediating the observed anti-Her-2 immune responses, FVB/N mice with NT-2 tumors were depleted of CD8+ T cells, beginning 1 day prior to vaccination with Lm-ΔLLO-Her-2 vaccines, then vaccinated as described in Example 2. In the CD8+-injected mice, each of the Lm-ΔLLO-Her-2 vaccines lost effectiveness (FIGS. 3A and B); while in the non-depleted mice, tumor growth was controlled, as observed in Example 2.

Figure 5:
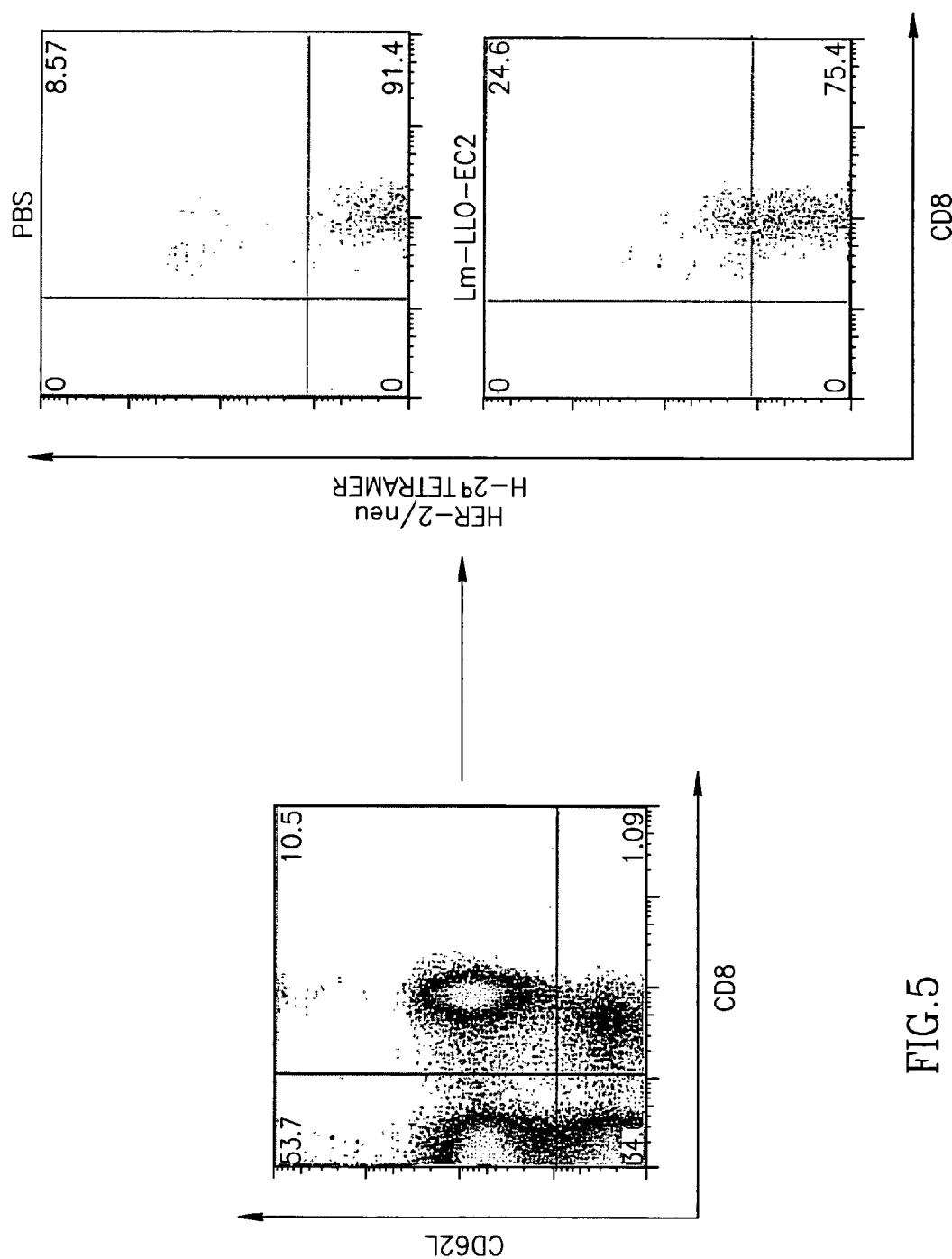
FIG. 5. Lm-ΔLLO-EC2 induces a 3-fold increase in tetramer+, CD8+ T cells. FVB/N mice were immunized with Lm-ΔLLO-EC2 or PBS. Subsequently, splenocytes were stained with an H-2$^q$ Her-2 tetramer, anti-CD8, and anti-CD62L.

Tetramer analysis was next used to confirm the above results. Non-tumor bearing 6-8 week-old FVB/N mice were immunized with either PBS or 0.1 $LD_{50}$ Lm-ΔLLO-EC2 and boosted 21 days later. Splenocytes were harvested 5 day's after the boost and were stained with an H-$2^q$ tetramer specific for the epitope defined by amino acids 420-429 (PDSLRDLVF), A three-fold increase in tetramer, positive cells was observed in the Lm-ΔLLO-EC2-vaccinated mice (FIG. 5).

These results show that CD8+ T cells are featured in the immunity elicited by the LLO-Her-2 fusion vaccines.

Example 4

LLO-Her-2 Fusion Vaccines Induce Immune Responses to Sub-Dominant CD8+ T Cell Epitopes Materials and Experimental Methods Cells NIH 3T3 cells, a mouse fibroblast line, were obtained from the American Type Culture Collection (ATCC). The NIH 3T3 and all the derived cells were cultured in DMEM supplemented with 10% FCS, 2 mM L-glutamine, 100 μM nonessential amino acids, 1 mM sodium pyruvate, 50 U/ml penicillin G, and 50 μg/ml streptomycin. Culture media for the 3T3-neu cell lines was supplemented with 1 mg/ml G418. Cells were grown at 37° C. with 5% $CO_2$.

3T3-Her-2 Lines

Briefly, wild type 3T3 cells were transduced with overlapping fragments of the rat Her-2 gene, creating nine 3T3 Her-2 fragment lines, and one 3T3 line expressing the full-length rat Her-2. Her-2 fragments were created using the following PCR primers:

```
Fragment 1 (bp 1-508):
                                  (SEQ ID No: 11)
5'-CCGGGCCGAATTCGCAATGATC
and (SEQ ID No: 12)
3'-CCCCGAATTCCTACTGAGGGTTCCCACGGATCAA.

Fragment 2 (bp 458-886):
                                  (SEQ ID No: 13)
5'-GACATGAAGTTGCGGCTCCCTAGTCTCACAGAGATCCTGAAG
and (SEQ ID No: 14)
3'-CCCCGAATTCCTACTCAGGGTTGTGCATGGACTC.

Fragment 3 (bp 836-1294):
                                  (SEQ ID No: 15)
5'-GACATGAAGTTGCGGCTCCCTGCCCTCGTCACCTACAACACA
and (SEQ ID No: 16)
3'-CCCCGAATTCCTAGAGGTCACGGAGACTGTCTGG.

Fragment 4 (bp 1244-1675):
                                  (SEQ ID No: 17)
5'-GACATGAAGTTGCGGCTCCCTATCACAGGTTACCTGTACATC
and (SEQ ID No: 18)
3'-CCCCGAATTCCTACTTCCATACTCGGCACTCCTC.

Fragment 5 (bp 1607-2077):
                                  (SEQ ID No: 19)
5'-GACATGAAGTTGCGGCTCCCTACCCAGTGTGTCAACTGCAGT
and (SEQ ID No: 20)
3'-CCCCGGTACCCTAGATCTTCTGTCTCCTTCGTTT.

Fragment 6 (bp 2009-2476):
                                  (SEQ ID No: 21)
5'-GACATGAAGTTGCGGCTCCCTGGCGTCCTGCTGTTCCTGATC
and (SEQ ID No: 22)
3'-CCCCGGTACCCTAACCTCGGTGTTCTCGGACATG.

Fragment 7 (bp 2405-2872),
                                  (SEQ ID No: 23)
5'-GACATGAAGTTGCGGCTCCCTTCCACAGTACAGCTGGTGACA
and (SEQ ID No: 24)
3'-CCCCGGTACCCTAGCAGATTGGAGGCTGAGGTAG.

Fragment 8 (bp 2801-3271),
                                  (SEQ ID No: 25)
5'-GACATGAAGTTGCGGCTCCCTGATGGAATCCCAGCCCGGGAG
and (SEQ ID No: 26)
3'-CCCCGGTACCCTACCCTTCCGAGGGAGCCAGTGG.

Fragment 9 (bp 3203-3796),
                                  (SEQ ID No: 27)
5'-GACATGAAGTTGCGGCTCCCTGAGCTGACACTGGGCCTGGAG
and (SEQ ID No: 28)
3'-CCCCGGTACCCTATACAGGTACATCCAGGCCTAG.
```

Fragments 1-9 span amino acids 1-165, 148-291, 274-426, 410-553, 531-687, 655-820, 797-952, 929-1085, 1063-1255 of Her-2, respectively. Each fragment was ligated into the pcDNA3.1 mammalian transfection vector, which contains a cytomegalovirus (CMV) promoter (Invitrogen, Carlsbad, Calif.), at the multicloning site. Constructs were transfected into 3T3 cells using electroporation (20 μg/1×$10^7$ cells) or Lipofectamine (1.5 μg/3×$10^5$ cells; Life Technologies). Several clones of each fragment were isolated by limiting dilution. Expression of Her-2 fragments in the clones was determined by RT-PCR.

Chromium Release Assay

FVB/N mice were immunized with 0.1 $LD_{50}$ of each of the Lm-ΔLLO-Her-2 vaccines. Splenocytes were harvested 9 days later and cultured for four days with irradiated (20,000 rads) NT-2 tumor cells at a 100:1 ratio of splenocytes to tumor cells with 20 U/ml IL-2 (Roche, Indianapolis, Ind.). Splenocytes were then used as effector cells in a standard $^{51}$Cr release assay. Target cells were labeled with chromium-51 ($^{53}$Cr) and cultured for four hours with splenocytes at effector:target ratios of 200:1, 100:1, 50:1, and 25:1 in triplicate. Following the incubation, 100 μl of supernatant was assayed for $^{51}$Cr release. The percent specific lysis was determined as

[(experimental counts per minute−spontaneous counts per minute)/(total counts per minute−spontaneous counts per minute)]×100. "Total counts per minute" refers to the total number of counts in the target cell population, measured by lysing the cells after labeling and counting the label. In other words, this is the maximum amount of $^{51}$Cr that could be released.

Results

Figure 6:
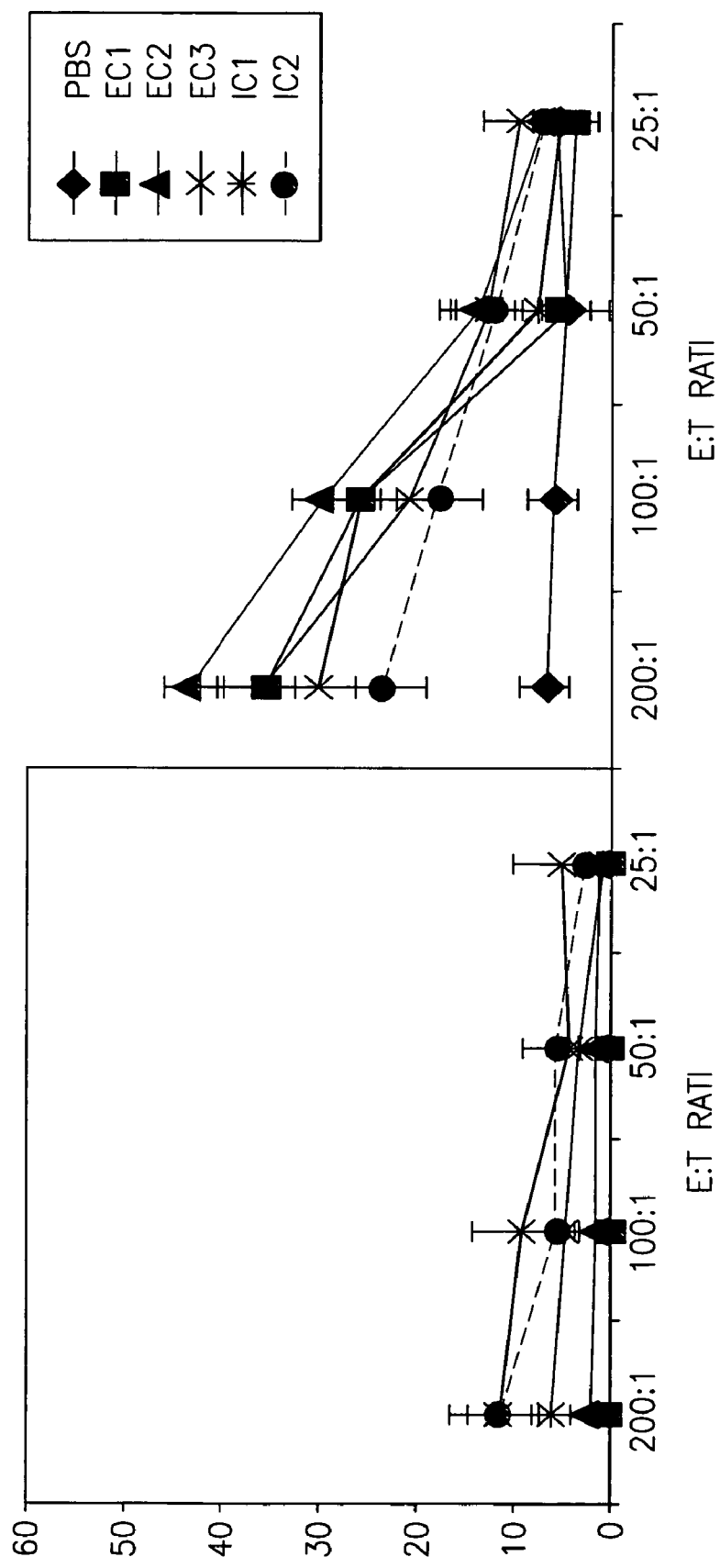
FIG. 6. Each of the Lm-ΔLLO-Her-2 vaccine constructs induces similar levels of anti-Her-2 CTL activity. A wildtype 3T3 (negative control). B. 3T3-neu (full length Her-2). Results are shown as the mean of triplicate cultures, and are representative of 5 experiments.

CTL assays were performed in order to confirm that each of the Lm-ΔLLO-Her-2 vaccines elicit anti-Her-2 CD8$^+$ T cell immune responses. Mice were vaccinated with each of the ΔLLO-Her-2 fusion vaccines, and splenocytes were isolated and tested for ability to induce lysis, as measured by $^{51}$Cr release assay, of 3T3 cells transduced with full length rat Her-2 (B), using wild-type 3T3 cells as a negative control (A). Each vaccine induced an anti-Her-2 CTL response, as evidenced by significant levels of lysis at E:T ratios of 200:1 or 100:1. Splenocytes from PBS-vaccinated mice, an additional negative control, induced only background levels of lysis (FIG. 6). These findings provide further evidence that each of the ΔLLO-Her-2 fusion vaccines induces anti-Her-2 CTL immune responses.

To delineate the epitopes recognized by the CTL, elicited by each vaccine, a panel of 3T3 cells expressing each of 9 Her-2 fragments were used as target cells in the above-described lysis assay, following vaccination with the corresponding ΔLLO-Her-2 fusion vaccine. Each vaccine elicited a CTL response to at least one Her-2 fragment. For several of the Her-2 fragments, levels of lysis over background reached statistical significance (p<0.05). Based on a combination of the negative and positive results, regions of Her-2 containing sub-dominant epitopes were delineated (Table 1). Thus, vaccination with the Lm-ΔLLO-Her-2 fragment vaccines revealed sub-dominant epitopes within Her-2 protein.

TABLE 1

Regions of Her-2/neu with potential H-2q epitopes, based on percent specific lysis in the CTL assay. Percent (specific lysis - background lysis by splenocytes from PBS-vaccinated mice) is depicted for the E:T ratios of 200:1 and 100:1. Assays were performed in triplicate; results of a representative experiment are shown.

| LM strain | Neu region spanned | | Percent Specific Lysis of Target Cells | | Neu regions containing an epitope |
|---|---|---|---|---|---|
| | | | 200:1 | 100:1 | |
| Lm-ΔLLO-EC1 | 20-326 | 3T3-neu-1 | 14.3* | 0.7 | 20-148 |
| | | 3T3-neu-2 | 0 | 0 | |
| | | 3T3-neu-3 | 6.5* | 3.5 | 291-326 |
| Lm-ΔLLO-EC2 | 303-501 | 3T3-neu-3 | 10.9* | 7.4 | 303-426 |
| | | 3T3-neu-4 | 23.8* | 8.4* | 410-501 |
| Lm-ΔLLO-EC3 | 479-655 | 3T3-neu-4 | 1 | 0 | |
| | | 3T3-neu-5 | 34.4* | 25.3* | 531-655 |
| Lm-ΔLLO- | 690-1081 | 3T3-neu-6 | 6.9* | 9* | 690-797 |

TABLE 1-continued

Regions of Her-2/neu with potential H-2q epitopes, based on percent specific lysis in the CTL assay. Percent (specific lysis - background lysis by splenocytes from PBS-vaccinated mice) is depicted for the E:T ratios of 200:1 and 100:1. Assays were performed in triplicate; results of a representative experiment are shown.

| LM strain | Neu region spanned | | Percent Specific Lysis of Target Cells | | Neu regions containing an epitope |
|---|---|---|---|---|---|
| | | | 200:1 | 100:1 | |
| IC1 | | 3T3-neu-7 | 0 | 2.3 | |
| | | 3T3-neu-8 | 18.2* | 6.4 | 952-1081 |
| Lm-ΔLLO-IC2 | 1020-1255 | 3T3-neu-8 | 10.3* | 8.2* | 1020-1085 |
| | | 3T3-neu-9 | 16.5 | 0 | 1063-1255 |

*Denotes statistically significant lysis above background (p < 0.05).

Example 5

Fusion to LLO and Delivery by LM Enhances the Immunogenicity of Her-2

Materials and Experimental Methods

DNA Vaccines

DNA vaccines were constructed using pcDNA 3.1. Her-2 and the EC1 fragment were amplified by PCR using the following primers:

Full length, unfused Her-2: 5' CCGG GCTAGCATGGTCATCATGGAGCTGGCCGG (Nhe I site underlined; SEQ ID No: 29) and 3' CCGG GATATCTTACTGTCATCGTCGTCCTTGTAGTCTCAT-ACAGGTACATCCA GGCC (EcoRV site underlined, FLAG tag in italics, stop codon in bold; SEQ ID No: 30). The above 5' primer was also used for amplifying unfused EC1, and the 3' primer for amplifying ΔLLO-full length Her-2.

ΔLLO-full length Her-2: 5' CCGG GTCGACATGGTCATCATGGAGCTGGCCGG (Sal I site underlined; SEQ ID No: 31). This primer was also used for amplifying ΔLLO-EC1.

Unfused EC1: 3' CCGG GATATCTTACTTGTCATCGTCGTCCTTGTAGTCTCA-GACCTCTTGGTTATTCGGGGG (EcoRV site underlined, FLAG tag in italics, stop codon in bold; SEQ ID No: 32). This primer was also used for amplifying unfused EC1 fused to ΔLLO.

Fragments were cloned into the multicloning site of pcDNA3.1, and used to transform *Escherichia coli*. Bacteria were grown in Luria-Bertani media (BD, Sparks, Md.) with 50 micrograms per milliliter (μg/ml) ampicillin.

Tumor Regression Experiments

Tumor regression experiments were performed as described in Example 2, except that 7×10$^5$ NT-2 cells were utilized, and vaccinations were administered on days 3, 10, and 18. DNA vaccines (50 μg each of the pcDNA plasmid+ and the GM-CSF plasmid or GM-CSF alone) were administered intra-muscularly and Lm administered intraperitoneally.

Results

Several factors were present in the Lm-ΔLLO-Her-2 vaccines that may have contributed to the recognition of sub-dominant epitopes: (a) delivery by LM; (b) fusion of the target antigen to ΔLLO; (c) breaking Her-2 into fragments. To determine which one or more of these factors contributed to the recognition of sub-dominant epitopes, as evidence by enhanced anti-Her-2 immune responses, mice were vaccinated with (a) pcDNA 3.1-full length Her-2 (a. DNA vaccine; "pcDNA neu"); (b) pcDNA 3.1 ΔLLO-full length Her-2 (pcDNA LLO-neu); (c) pcDNA 3.1-EC1 (pcDNA EC1); (d) pcDNA 31-ΔLLO-EC1 (pcDNA LLO-EC1); or (e) Lm-ΔLLO-EC1, and a tumor regression experiment was performed GM-CSF was included with the DNA vaccines because of its ability to enhance the efficacy of DNA vaccines (McKay P F, Barouch D H et al, Eur J Immunol 2004 April; 34(4): 1011-20).

Figure 7A:
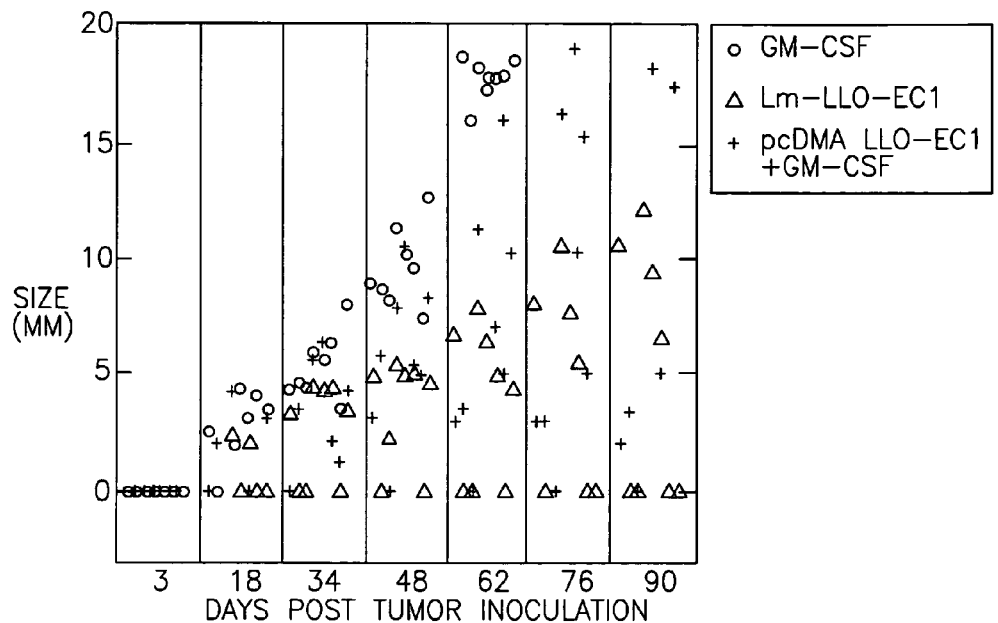
FIG. 7. Delivery by LM and fusion to ΔLLO increases the anti-tumor immune response of Her-2 vaccines. Average tumor diameter for each mouse is depicted. Tumor measurements are shown only for the surviving mice at a given time point. (A) Lm-ΔLLO-EC1 vs. pcDNA ΔLLO-EC1+GM-CSF, (B) pcDNA EC1+GM-CSF vs. pcDNA ΔLLO-EC1+GM-CSF, (C) pcDNA neu+GM-CSF vs. pcDNA ΔLLO-neu+GM-CSF, (D) pcDNA ΔLLO-neu+GM-CSF vs. pcDNA ΔLLO-EC1+GM-CSF and (E) pcDNA neu+GM-CSF vs. pcDNA EC1+GM-CSF.
Figure 7B:
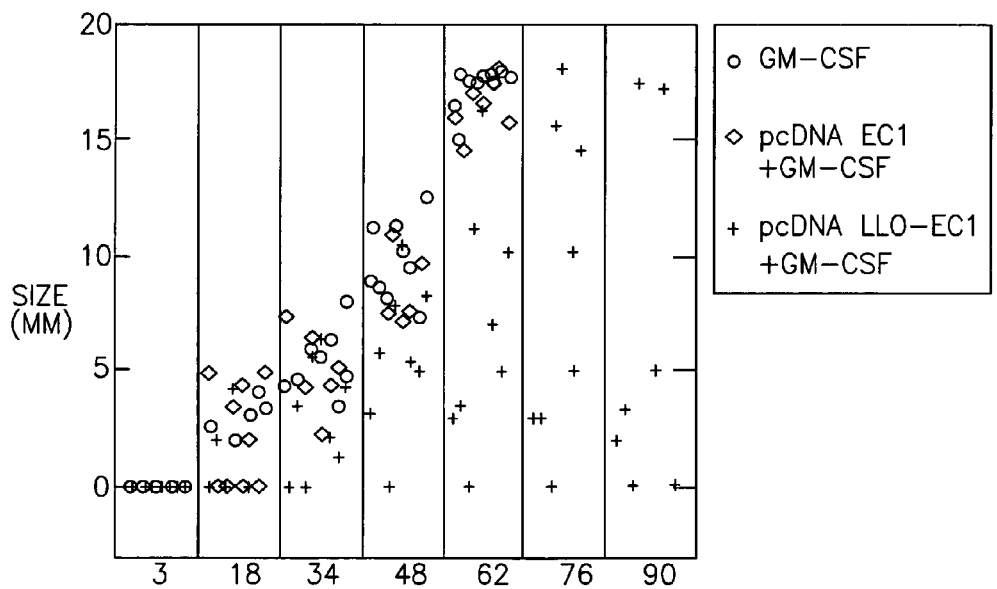
Figure 7C:
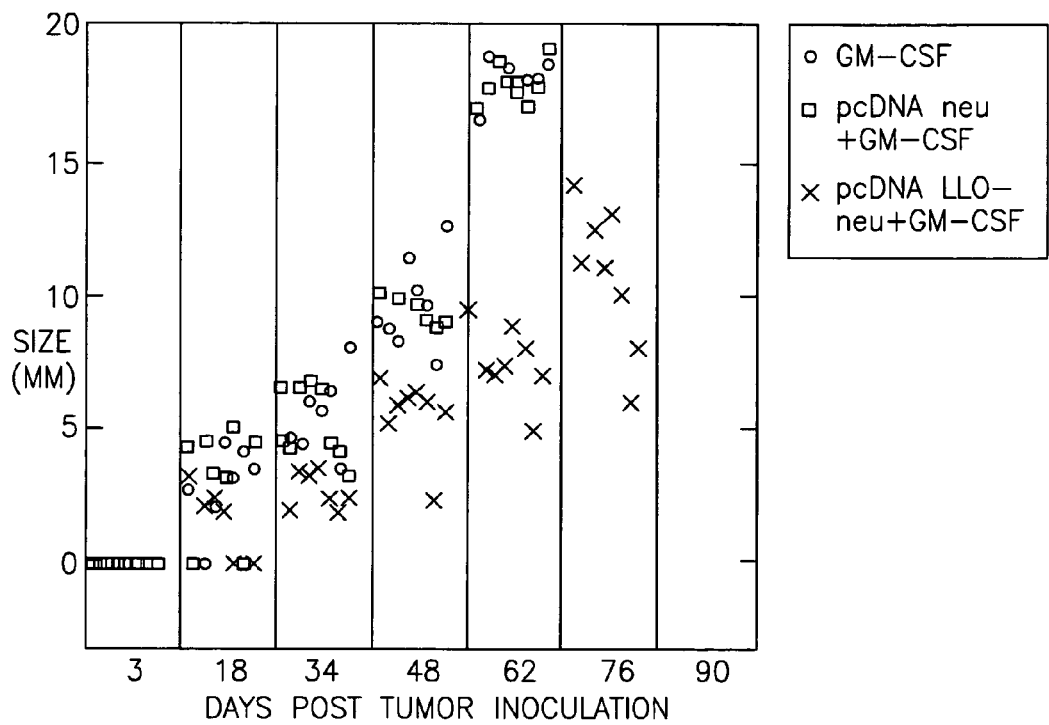
Figure 7D:
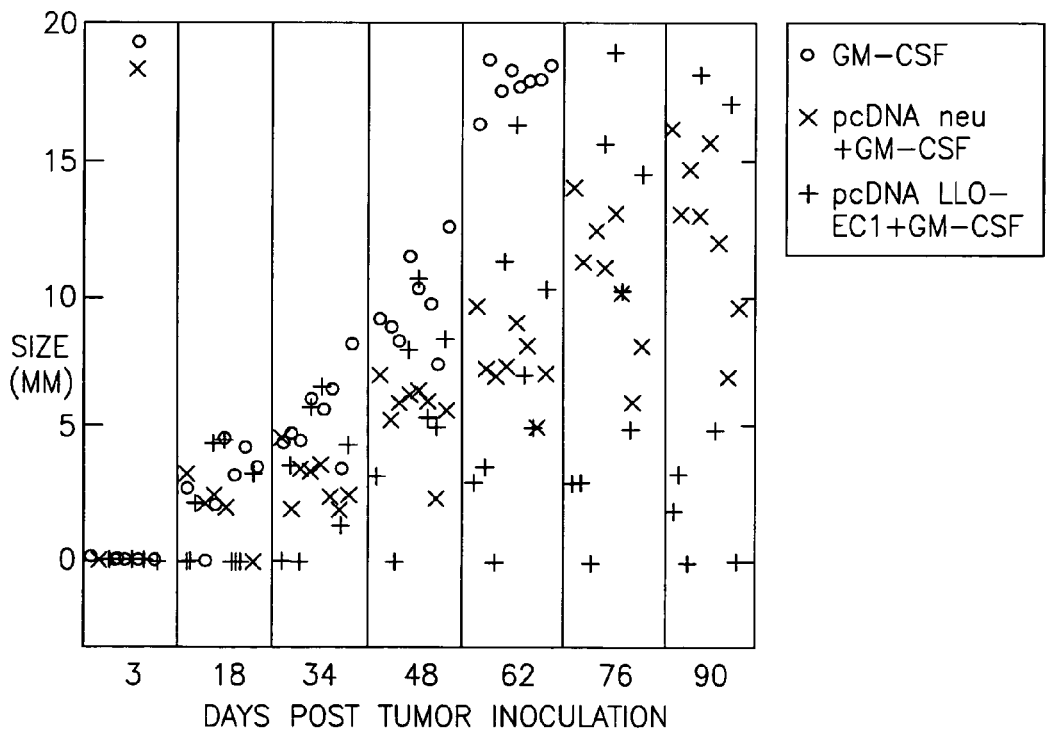
Figure 7E:
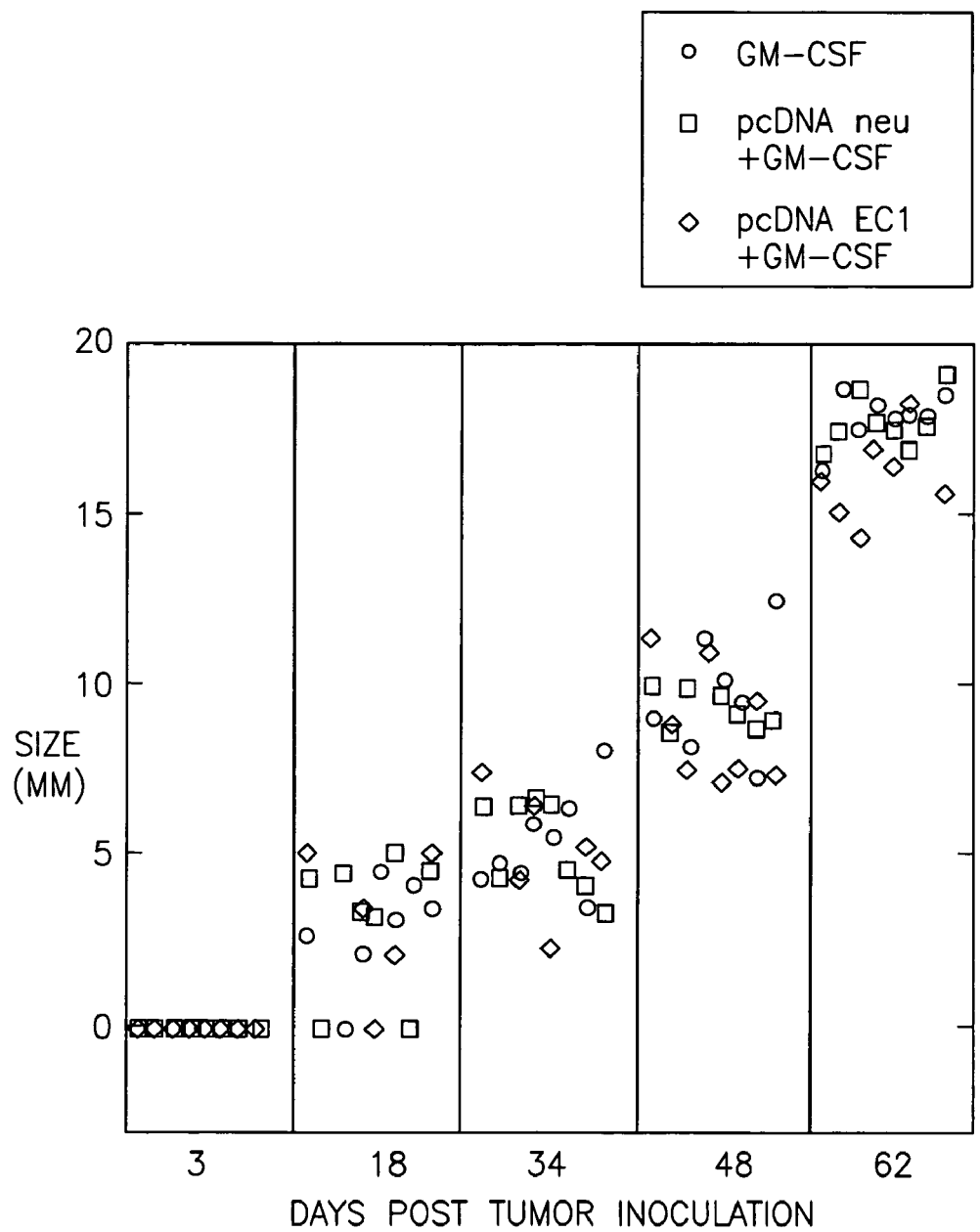

As depicted in FIG. 7A, the best control of tumor growth was observed with Lm-ΔLLO-EC1; 2/8 of the mice never developed palpable tumors; the tumor completely regressed in another two; and the other 4 mice exhibited slower (retarded) tumor growth than the mock-vaccinated controls. In the case of pcDNA ΔLLO-EC1, one mouse never developed a tumor, and several of the other mice exhibited retarded tumor growth. Fusion to ΔLLO enhanced immunogenicity of EC1, as seen by comparison of pcDNA EC1 vs. pcDNA ΔLLO-EC1 and pcDNA neu vs. pcDNA ΔLLO-neu (FIGS. 6B-C); vaccines in which the antigen was unfused exhibited tumors that grew at the same rate as mock-vaccinated controls. An enhancing effect of dividing Her-2 into smaller fragments, in the case of the ΔLLO fusions, is seen from a comparison of pcDNA ΔLLO-neu vs. pcDNA ΔLLO-EC1, in which the latter group exhibited superior tumor control (FIG. 7D). No effect was seen for the unfused antigens, as seen from a comparison of pcDNA neu vs. pcDNA EC1 (FIG. 7E).

Example 6

LLO-Her-2 DNA Vaccines Induce Immune Responses to Sub-Dominant CD8+ T Cell Epitopes Immune responses to the DNA vaccines were further analyzed by measuring lysis of 3T3 cells transduced with Her-2 fragments, as described in Example 4. T cells from mice vaccinated with pcDNA 3.1-ΔLLO-Her-2 or pcDNA 3.1-ΔLLO-EC1 lysed cells from more 3T3-Her-2 target cell groups than did the corresponding non-fused DNA vaccines (Table 2).

TABLE 2

Regions of Her-2/neu with potential epitopes based on DNA vaccinations of wt FVB mice.

| LM strain | Neu region spanned | | Percent Specific Lysis of Target Cells | | Neu regions containing an epitope |
|---|---|---|---|---|---|
| | | | 200:1 | 100:1 | |
| pcDNA neu + GM-CSF | 1-1255 | 3T3-neu-1 | 17.4* | 12.4* | 20-148 |
| | | 3T3-neu-2 | 0 | 0.1 | |
| | | 3T3-neu-3 | 0 | 1.6 | |
| | | 3T3-neu-4 | 23.4* | 19.5* | 410-479 |
| | | 3T3-neu-5 | 0 | 0.3 | |
| | | 3T3-neu-6 | 2.6 | 0 | |
| | | 3T3-neu-7 | 0 | 0.6 | |
| | | 3T3-neu-8 | 0 | 1.2 | |
| | | 3T3-neu-9 | 0 | 0.1 | |
| pcDNA ΔLLO-neu + GM-CSF | 1-1255 | 3T3-neu-1 | 30.9* | 20.5* | 20-148 |
| | | 3T3-neu-2 | 0.4 | 0 | |
| | | 3T3-neu-3 | 1.9 | 1.7 | |
| | | 3T3-neu-4 | 31.2* | 25.5* | 410-501 |
| | | 3T3-neu-5 | 6.4* | 6.4 | 479-531 |
| | | 3T3-neu-6 | 0 | 0 | |
| | | 3T3-neu-7 | 0 | 2.5 | |
| | | 3T3-neu-8 | 0 | 4 | |
| | | 3T3-neu-9 | 21* | 15.8* | 1085-1255 |
| pcDNA EC1 + GM-CSF | 1-326 | 3T3-neu-1 | 7.8 | 1.9 | |
| | | 3T3-neu-2 | 0 | 2.1 | |
| | | 3T3-neu-3 | 8.5* | 0 | 291-326 |
| pcDNA ΔLLO-EC1 + GM-CSF | 1-326 | 3T3-neu-1 | 14.6* | 8.5* | 20-148 |
| | | 3T3-neu-2 | 0 | 0.5 | |
| | | 3T3-neu-3 | 9.9* | 5.1 | 291-326 |

*denotes statistically significant lysis above background ($p < 0.05$). Percent specific lysis was calculated as % = 100 × ((experimental lysis − spontaneous lysis)/(total lysis − spontaneous lysis)).

Thus, fusion of an LLO fragment to full length Her-2 or a Her-2 fragment resulted in a broadening of the regions recognized by CTLs. Accordingly, based on the results of Examples 5-6, subdominant CD8+ antigen epitopes can be revealed by either (a) expression by LM; (b) fusion of the antigen to an LLO fragment; or (c) dividing the antigen into smaller fragments.

Example 7

Vaccination with LLO-Her-2 Induces Epitope Spreading Materials and Experimental Methods FVB/N are injected with NT-2 tumors, then vaccinated with each of the LM-ΔLLO-Her-2 fragment strains, as described in Example 2, or with DNA ΔLLO-Her-2 fragment vaccines, as described in Example 5. Lymphocytes are isolated from the draining lymph nodes of the tumor site at various time points following vaccination. Epitopes recognized by the lymphocytes are determined by a lysis assay, using 3T3 cells expressing each of 9H er-2 fragments, as described in Example 4.

Results

The induction of tumor regression at more than one month after the final boost is in contrast with observations using other types of vaccines, and suggests that the number of T cell subsets is being expanded by epitope spreading. For example, antigen presenting cells such as dendridic cells may be acquiring pieces of the dying cells, traveling to the draining lymph nodes, and presenting Her-2 epitopes not present in the vaccine fragment, resulting in a broadening of the and Her-2 CD8+ T cell response. To confirm this conclusion, mice are injected with NT-2 tumors, then vaccinated with each of the LM-ΔLLO-Her-2 fragment strains or DNA ΔLLO-Her-2 fragment vaccines. Lymphocytes are isolated tumor draining lymph nodes at various time points, and the epitopes recognized by the lymphocytes are determined. Emergence is observed of reactivity to epitopes not present in the vaccine fragment. This broadening of the T cell response approximately correlates with temporally tumor regression.

This result demonstrates that vaccination with recombinant antigen-expressing LM induces epitope spreading. In addition, vaccination with LLO-antigen fusions, even outside the context of LM, induces epitope spreading as well.

Example 8

Vaccination with LLO-Her-2 Overcomes Immune Tolerance to a Self Antigen

Materials and Experimental Methods

Rat Her-2/neu transgenic mice were provided by Dr. William Muller. Young, virgin HER-2/neu transgenic mice that had not spontaneously developed tumors were injected with $5 \times 10^4$ NT-2 cells. Because the transgenic mouse is profoundly tolerant to HER-2/neu, the minimum dose required for tumor growth in 100% of animals is much lower than wild-type mice (Reilly R T, Gottlieb M B et al, Cancer Res. 2000 Jul. 1; 60(13): 3569-76) NT-2 cells were injected into the subcutaneous space of the flank. Mice received 0.1 $LD_{50}$ of the Listeria vaccine when 4-5 mm palpable tumors were detected (typically on day 7 after tumor implantation) and weekly thereafter, for an additional 4 weeks.

Results

The rat Her-2/neu gene differs from the rat neu by 5-6% of amino acid residues, and thus is immunogenic in the mouse (Nagata Y, Furugen R et al, J Immunol 159:1336-43). A transgenic mouse that over expresses rat Her-2/neu under the transcriptional control of the Mouse Mammary Tumor Virus (MMTV) promoter and enhancer is immunologically tolerant to rat Her-2/neu. These mice spontaneously develop breast cancer. The MMTV promoter also operates in hematopoietic cells, rendering the mice profoundly tolerant to HER-2/neu. This, this mouse is considered to be stringent model for human breast cancer and in general for tumors expressing antigens, such as Her-2/neu, that are expressed at low levels in normal tissue (Muller W. J. (1991) Expression of activated oncogenes in the murine mammary gland: transgenic models for human breast cancer. Canc Metastasis Rev 10: 217-27).

Figure 8:
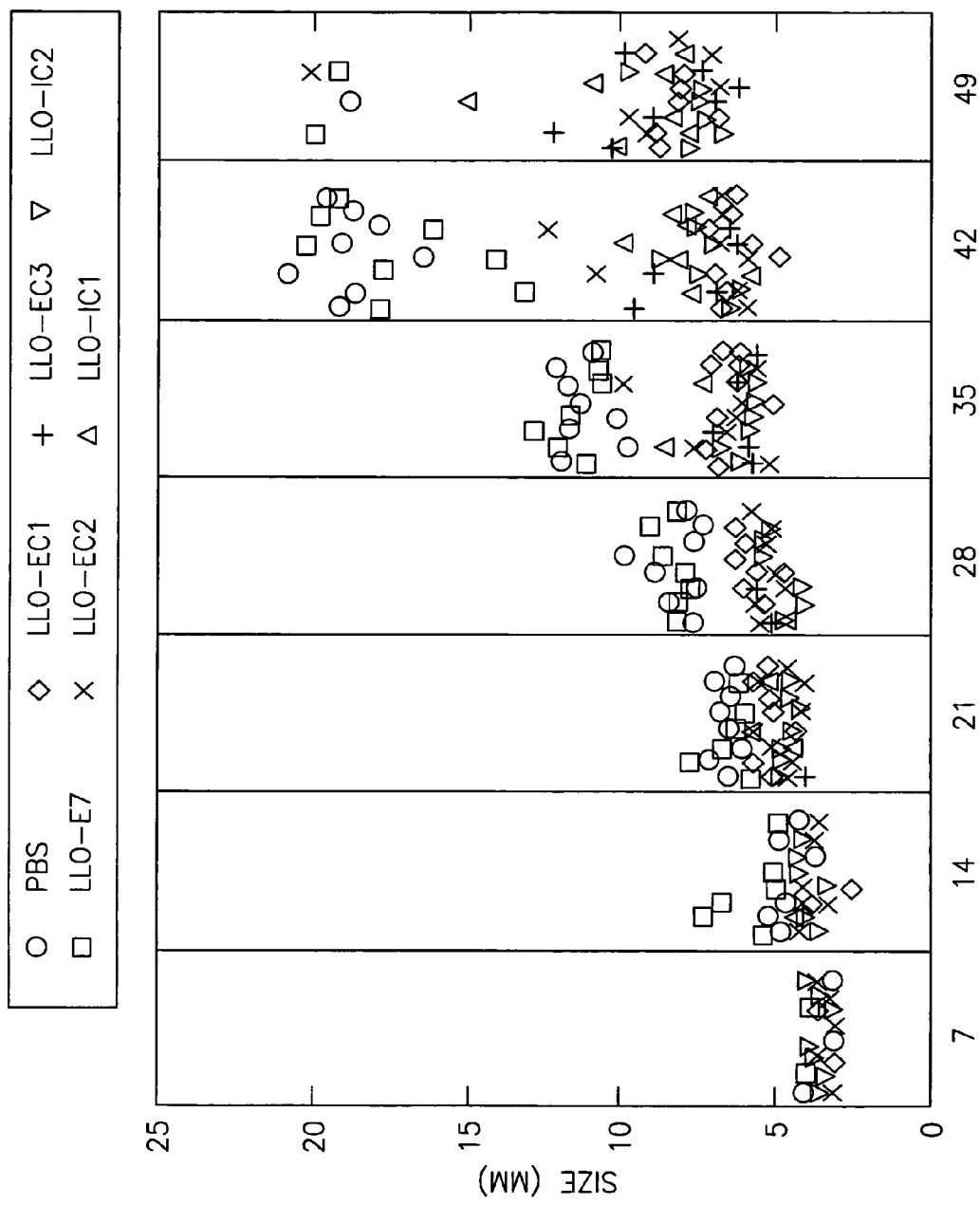
FIG. 8. Lm-ΔLLO-Her-2 vaccine slow the growth of established rat Her-2 expressing tumors in rat Her-2/neu transgenic mice, in which rat Her-2 is expressed as a self-antigen.

6-8 week-old HER-2/neu transgenic mice were injected with NT-2 cells, then immunized with each of the LM-$\Delta$LLO-Her-2 vaccines, or with PBS or $\Delta$LLO-E7 (negative controls). While most control mice had to be sacrificed by day 42 because of their tumor burden, tumor growth was controlled in all of the vaccinated mice (FIG. 8).

Thus, the $\Delta$LM-LLO-Her-2 and Listeria-based Her-2 vaccines are able to break tolerance to self antigen expressed on a tumor cell, as evidenced by their ability to induce the regression of established NT-2 tumors.

Example 9

LLO-HER-2 Vaccines Control Spontaneous Tumor Growth in HER-2/NEU Transgenic Mice Materials and Experimental Methods $\Delta$LM-LLO-Her-2 vaccines were administered in the following amounts: Lm-LLO-EC1: 1×10^7 cfu; Lm-Lm-LLO-IC2: 5×10^7 cfu; LLO-EC3: 1×10^8 cfu; Lm-LLO-IC2: 1×10^7 cfu; Lm-LLO-IC1: 1×10^7.

Results

Figure 9:
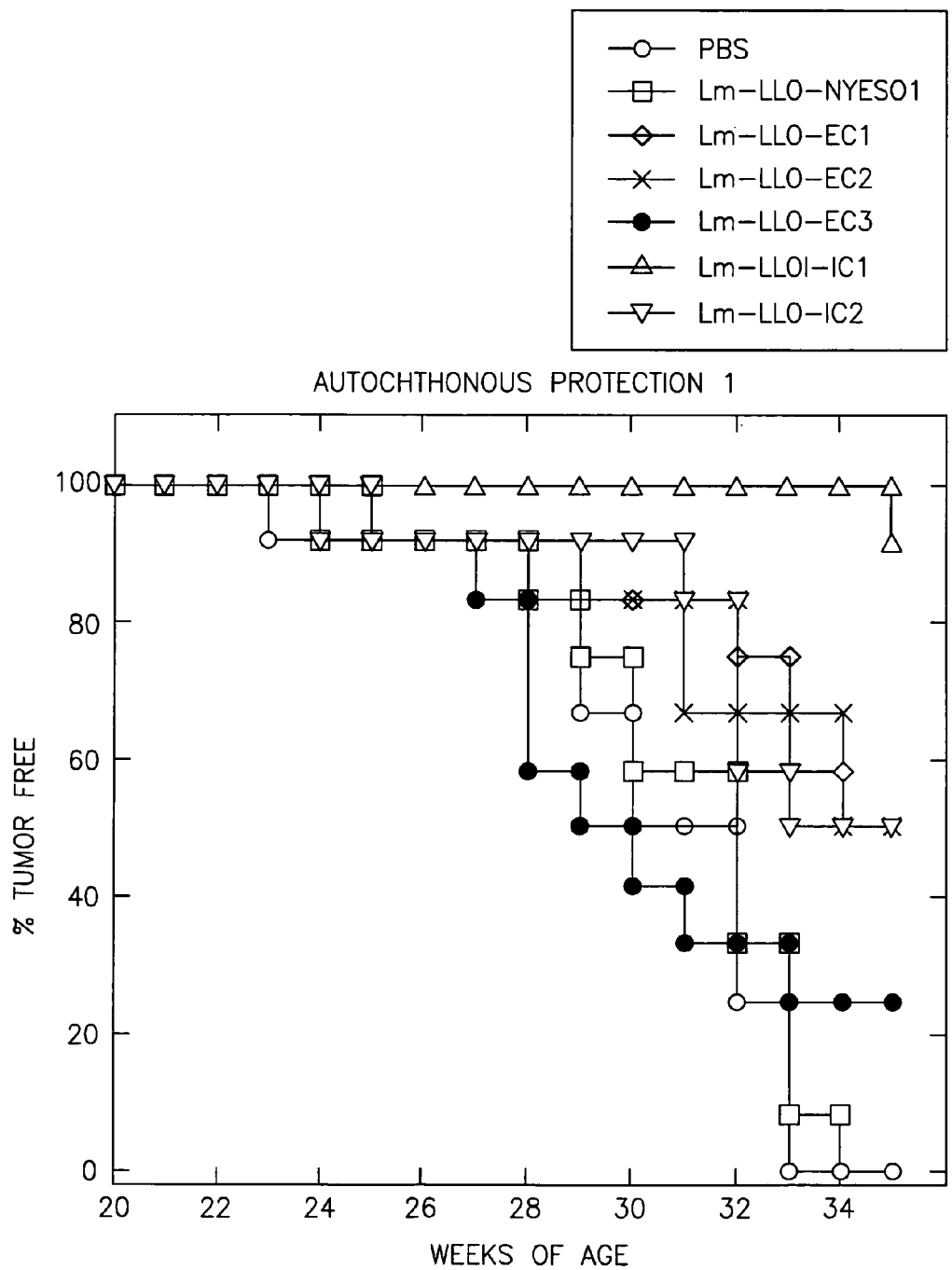
FIG. 9. LLO-Her-2 vaccines control spontaneous tumor growth in Her-2/neu transgenic mice.

The $\Delta$LM-LLO-Her-2 vaccines were also evaluated for ability to prevent spontaneous tumor growth in the Her-2/neu transgenic mice. The transgenic mice (n=12 per vaccine group) were immunized 5 times with 0.1 $LD_{50}$ of one of the vaccine strains, beginning at age 6 weeks and continuing once every three weeks. Mice were monitored for tumor formation in the mammary glands. By week 35, all of the control mice (PBS or Lm-LLO-NY-ESO-1-immunized) had developed tumors. By contrast, 92% of the Lm-LLO-IC1 group were tumor free, as were 50% of the mice Lm-LLO-EC2, Lm-LLO-EC1, and Lm-LLO-IC2, and 25% of the mice immunized with Lm-LLO-EC3 (FIG. 9).

This finding confirm the results of the previous Example, showing that $\Delta$LM-LLO-Her-2 and Listeria-based Her-2 vaccines are able to break tolerance to self antigens.

Example 10

Generation of LLO-HER-2 Vaccines Containing Fragments of Human HER-2 Protein

Figure 10:
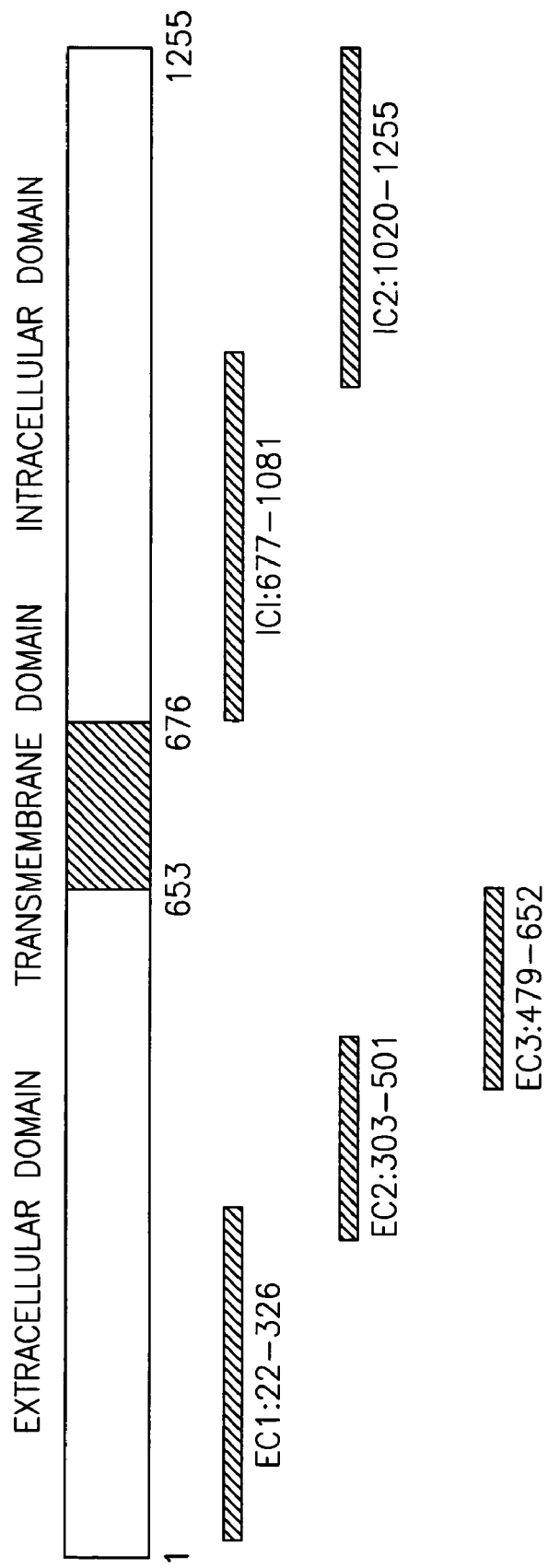
FIG. 10. Schematic representation of human Her-2 fragments used to create LLO-human Her-2 vaccines.

A similar strategy was used to express human Her-2/neu as was used for rat Her-2 (Example 1). The full-length HER-2 gene was split into five fragments, constituting overlapping fragments of the extracellular domain, (EC-1, EC-2 and EC-3) and the cytoplasmic domain (IC-1 and IC-2) (FIG. 10). Hydrophobic regions were not included in the constructs. These sequences differed from the rat sequences slightly due to the small disimilarities between the two sequences. The human fragments corresponding to the rat fragments were 22-326, 303-501, 479-652, 677-1081, and 1020-1255.

The human HER-2 sequences are isolated from a human breast cell cancer line erg. SK-BR3 (ATCC) by reverse transcription PCR (RT-PCR) using standard molecular biology methods. For example, total cellular RNA is isolated using the RNeasy Minipreparation® kit (Qiagen) and a cDNA pool is generated (Titan-One-Tube PCR system®, Roche) using an oligo-dT primer. The HER-2 sequences of interest are specifically amplified by the second step PCR using the following primers:

| Construct | 5' Primer | | 3' Primer | |
|---|---|---|---|---|
| EC1 | ctcgaggccgcgagcacccaagtg | (SEQ ID No: 45) | actagtttaatcctctgctgtcacctc | (SEQ ID No: 46) |
| EC2 | ctcgagtacctttctacggacgtg | (SEQ ID No: 47) | actagtttactctggccggttggcag | (SEQ ID No: 48) |
| EC3 | ctcgagacggtgccctgggaccag | (SEQ ID No: 49) | actagtttagacgatggacgtcagag | (SEQ ID No: 50) |
| IC1 | ctcgagctgctgcaggaaacggag | (SEQ ID No: 51) | actagtttaagcccccttcggagggtg | (SEQ ID No: 52) |
| IC2 | ctcgaggctgaggagtatctg | (SEQ ID No: 53) | actagtttacactggcacgtccagac | (SEQ ID No: 54) |

Restriction sites XhoI (5') and SpeI (3') are added to allow for subsequent cloning into the *Listeria* vaccine vector, and an ochre stop codon is included in the reverse primers to terminate translation of the fusion protein. There are no XhoI or SpeI sequences located in these fragments of the human HER-2 gene. The PCR products are purified (Qiaquick® PCR Purification Kit, Qiagen) and cloned into intermediate *E. coli* vector pCR2.1 TOPO® (Invitrogen) After transformation of TOP10 cells (Invitrogen), plasmid containing colonies are identified by PCR using primers M13 forward and M13 reverse (Invitrogen). One positive clone for each construct is grown up, plasmid DNA will be prepared (Qiafilter Midipreparation®, Qiagen) and the sequence of the HER-2/neu insert is verified by sequencing.

In order to introduce the HER-2/neu antigen sequences into the *Listeria* vector, pLLO-E7 is digested completely with XhoI and partially with SpeI, thereby removing the E7 gene. The HER-electrophoresis, and the pLLO-E7 vector and the HER-2/neu insert sequences are purified (Qiaquick). The HER-2/neu antigen sequences are ligated into pLLO-E7, and the ligation mix is transformed into d-alanine racemase-deficient *E. coli* strain MB2159 by electroporation. Colonies are tested by PCR for the presence of the HER-2/neu sequence and expanded in Luria Broth (LB) media, and plasmid DNA is prepared, then the sequence verified by restriction digestion with EcoRI, SmaI, NcoI or with HindIII which yields a specific band pattern for each construct. Plasmids are transformed into *Listeria* strain Lm(DA-) by electroporation, and individual clones are grown up in LB media containing 50 µg/ml streptomycin. The presence and sequence of the plasmid is again verified by restriction analysis. Expression and secretion of LLO-HER-2/neu fusion proteins is verified by Western blot of TCA-precipitated culture media, using a polyclonal PEST sequence-specific antibody.

Example 11

Testing OF LLO-HER-2 Vaccines Containing Fragments of Human HER-2 Protein

The LLO-human Her-2 strains are tested for immunogenicity in mice and in human volunteers. Next, the vaccine strains are tested for their ability to protect mice against a challenge with tumor cells expressing human Her-2, as described in the above Examples Successful strains are administered to humans having Her-2-expressing tumors, and tested for their ability to induce tumor regression. In addition, the strains are tested for their ability to protect human subjects at risk for developing Her-2-expressing cancer, due to genetic or environmental factors. The vaccine strains are found to be immunogenic and to exhibit substantial anti-tumor activity.

What is claimed is:

1. A recombinant form of *Listeria* comprising a nucleotide molecule encoding a recombinant polypeptide comprising an N-terminal fragment of a listeriolysin (LLO) protein fused to a fragment of a Her-2 protein, wherein said fragment of a Her-2 protein consists of amino acids 303-501, 479-655, or 1020-1255 of SEQ ID NO: 40 or amino acids 303-501, 479-652, or 1020-1255 of SEQ ID NO: 43.

2. The recombinant form of *Listeria* of claim 1, wherein said N-terminal fragment of a listeriolysin (LLO) protein is non-hemolytic.

3. An immunogenic composition comprising the recombinant form of *Listeria* of claim 1.

4. A recombinant form of *Listeria* comprising a nucleotide molecule encoding a fragment of a Her-2 protein wherein said fragment of a Her-2 protein consists of amino acids 303-501, 479-655, or 1020-1255 of SEQ ID NO: 40 or amino acids 303-501, 479-652, or 1020-1255 of SEQ ID NO: 43.

5. The recombinant form of *Listeria* of claim 4, wherein said Her-2 protein is a human Her-2 protein.

6. An immunogenic composition comprising the recombinant form of *Listeria* of claim 4.

7. A recombinant *L. monocytogenes* strain expressing a recombinant fusion polypeptide comprising an N-terminal listeriolysin (LLO) fragment fused to a fragment of a Her-2 protein, wherein said fragment consists of amino acids 303-501 or 479-655 of SEQ ID NO: 40 or amino acids 303-501 or 479-652 of SEQ ID NO: 43.

8. A recombinant *L. monocytogenes* strain expressing a recombinant fusion polypeptide comprising an N-terminal listeriolysin (LLO) fragment fused to a fragment of a Her-2 protein, wherein said fragment consists of amino acids 1020-1255 of SEQ ID NO: 40 or amino acids 1020-1255 of SEQ ID NO: 43.

9. The recombinant form of *Listeria* of claim 1, wherein said fragment of a Her-2 protein consists of amino acids 303-501 of SEQ ID NO: 40.

10. The recombinant form of *Listeria* of claim 1, wherein said fragment of a Her-2 protein consists of amino acids 303-501 of SEQ ID NO: 43.

11. The recombinant form of *Listeria* of claim 1, wherein said fragment of a Her-2 protein consists of amino acids 479-655 of SEQ ID NO: 40.

12. The recombinant form of *Listeria* of claim 1, wherein said fragment of a Her-2 protein consists of amino acids 479-652 of SEQ ID NO: 43.

13. The recombinant form of *Listeria* of claim 1, wherein said fragment of a Her-2 protein consists of amino acids 1020-1255 of SEQ ID NO: 40.

14. The recombinant form of *Listeria* of claim 1, wherein said fragment of a Her-2 protein consists of amino acids 1020-1255 of SEQ ID NO: 43.

15. The recombinant form of *Listeria* of claim 4, wherein said fragment of a Her-2 protein consists of amino acids 303-501 of SEQ ID NO: 40.

16. The recombinant form of *Listeria* of claim 4, wherein said fragment of a Her-2 protein consists of amino acids 303-501 of SEQ ID NO: 43.

17. The recombinant form of *Listeria* of claim 4, wherein said fragment of a Her-2 protein consists of amino acids 479-655 of SEQ ID NO: 40.

18. The recombinant form of *Listeria* of claim 4, wherein said fragment of a Her-2 protein consists of amino acids 479-652 of SEQ ID NO: 43.

19. The recombinant form of *Listeria* of claim 4, wherein said fragment of a Her-2 protein consists of amino acids 1020-1255 of SEQ ID NO: 40.

20. The recombinant form of *Listeria* of claim 4, wherein said fragment of a Her-2 protein consists of amino acids 1020-1255 of SEQ ID NO: 43.

21. A method of inducing an anti-Her-2 immune response in a subject, comprising administering to said subject the recombinant form of *Listeria* of claim 1, thereby inducing an anti-Her-2 immune response in said subject.

22. The method of claim 21, wherein said immune response comprises a CD8+ T cell-mediated response.

23. The method of claim 21, whereby said immune response comprises an immune response to a subdominant epitope of said Her-2 protein.

24. A method of impeding the growth of a Her-2-expressing tumor in a subject, comprising administering to said subject the recombinant form of *Listeria* of claim 1, whereby said subject mounts an immune response against said Her-2-expressing tumor, thereby impeding the growth of said Her-2-expressing tumor in said subject.

25. The method of claim 24, wherein said immune response comprises a CD8+ T cell-mediated response.

26. The method of claim 24, whereby said immune response against said Her-2-expressing tumor comprises an immune response to a subdominant epitope of said Her-2 protein.

27. A method of shrinking a Her-2-expressing tumor in a subject, comprising administering to said subject the recombinant form of *Listeria* of claim 1, whereby said subject mounts an immune response against said Her-2-expressing tumor, thereby shrinking said Her-2-expressing tumor in said subject.

28. The method of claim 27, wherein said immune response comprises a CD8$^+$ T cell-mediated response.

29. The method of claim 27, whereby said immune response against said Her-2-expressing tumor comprises an immune response to a subdominant epitope of said Her-2 protein.

30. A method of breaking an immune tolerance of a subject to an antigen-expressing tumor, comprising administering to said subject the recombinant form of *Listeria* of claim 1, wherein said Her-2 protein has one or more dominant CD8$^+$ T cell epitopes and wherein said fragment does not contain said any of said dominant CD8$^+$ T cell epitopes, whereby said subject mounts an immune response against said antigen-expressing tumor, thereby breaking an immune tolerance of a subject to an antigen-expressing tumor.

31. The method of claim 30, wherein said Her-2 protein is expressed at a detectable level on a non-tumor cell of said subject.

32. The method of claim 30, wherein at least part of said immune response is a CD8$^+$ T cell response directed against an epitope of said Her-2 protein that is not any of said dominant CD8$^+$ T cell epitopes.

33. A method of inducing a CD8$^+$ T cell-mediated immune response in a subject against a subdominant CD8$^+$ T cell epitope of an antigen, comprising administering to said subject the recombinant form of *Listeria* of claim 1, thereby inducing a CD8$^+$ T cell-mediated immune response against a subdominant CD8$^+$ T cell epitope of an antigen.

34. A method of inducing an anti-Her-2 immune response in a subject, comprising administering to said subject the recombinant form of *Listeria* of claim 4, thereby inducing an anti-Her-2 immune response in said subject.

35. The method of claim 34, wherein said immune response comprises a CD8+ T cell-mediated response.

36. The method of claim 34, whereby said immune response comprises an immune response to a subdominant epitope of said Her-2 protein.

37. A method of impeding the growth of a Her-2-expressing tumor in a subject, comprising administering to said subject the recombinant form of *Listeria* of claim 4, whereby said subject mounts an immune response against said Her-2-expressing tumor, thereby impeding the growth of said Her-2-expressing tumor in said subject.

38. The method of claim 37, wherein said immune response comprises a CD8+ T cell-mediated response.

39. The method of claim 37, whereby said immune response against said Her-2-expressing tumor comprises an immune response to a subdominant epitope of said Her-2 protein.

40. A method of shrinking a Her-2-expressing tumor in a subject, comprising administering to said subject the recombinant form of *Listeria* of claim 4, whereby said subject mounts an immune response against said Her-2-expressing tumor, thereby shrinking said Her-2-expressing tumor in said subject.

41. The method of claim 40, wherein said immune response comprises a CD8$^+$ T cell-mediated response.

42. The method of claim 40, whereby said immune response against said Her-2-expressing tumor comprises an immune response to a subdominant epitope of said Her-2 protein.

43. A method of breaking an immune tolerance of a subject to an antigen-expressing tumor, comprising administering to said subject the recombinant form of *Listeria* of claim 4, wherein said Her-2 protein has one or more dominant CD8$^+$ T cell epitopes and wherein said fragment does not contain said any of said dominant CD8$^+$ T cell epitopes, whereby said subject mounts an immune response against said antigen-expressing tumor, thereby breaking an immune tolerance of a subject to an antigen-expressing tumor.

44. The method of claim 43, wherein said Her-2 protein is expressed at a detectable level on a non-tumor cell of said subject.

45. The method of claim 43, wherein at least part of said immune response is a CD8$^+$ T cell response directed against an epitope of said Her-2 protein that is not any of said dominant CD8$^+$ T cell epitopes.

46. A method of inducing a CD8$^+$ T cell-mediated immune response in a subject against a subdominant CD8$^+$ T cell epitope of an antigen, comprising administering to said subject the recombinant form of *Listeria* of claim 4, thereby inducing a CD8$^+$ T cell-mediated immune response against a subdominant CD8$^+$ T cell epitope of an antigen.

47. A method of inducing an anti-Her-2 immune response in a subject, comprising administering to said subject the recombinant form of *Listeria* of claim 7, thereby inducing an anti-Her-2 immune response in said subject.

48. The method of claim 47, wherein said immune response comprises a CD8+ T cell-mediated response.

49. The method of claim 47, whereby said immune response comprises an immune response to a subdominant epitope of said Her-2 protein.

50. A method of impeding the growth of a Her-2-expressing tumor in a subject, comprising administering to said subject the recombinant form of *Listeria* of claim 7, whereby said subject mounts an immune response against said Her-2-expressing tumor, thereby impeding the growth of said Her-2-expressing tumor in said subject.

51. The method of claim 50, wherein said immune response comprises a CD8+ T cell-mediated response.

52. The method of claim 50, whereby said immune response against said Her-2-expressing tumor comprises an immune response to a subdominant epitope of said Her-2 protein.

53. A method of shrinking a Her-2-expressing tumor in a subject, comprising administering to said subject the recombinant form of *Listeria* of claim 7, whereby said subject mounts an immune response against said Her-2-expressing tumor, thereby shrinking said Her-2-expressing tumor in said subject.

54. The method of claim 53, wherein said immune response comprises a CD8$^+$ T cell-mediated response.

55. The method of claim 53, whereby said immune response against said Her-2-expressing tumor comprises an immune response to a subdominant epitope of said Her-2 protein.

56. A method of breaking an immune tolerance of a subject to an antigen-expressing tumor, comprising administering to said subject the recombinant form of *Listeria* of claim 7, wherein said Her-2 protein has one or more dominant CD8$^+$ T cell epitopes and wherein said fragment does not contain said any of said dominant CD8$^+$ T cell epitopes, whereby said subject mounts an immune response against said antigen-expressing tumor, thereby breaking an immune tolerance of a subject to an antigen-expressing tumor.

57. The method of claim 56, wherein said Her-2 protein is expressed at a detectable level on a non-tumor cell of said subject.

58. The method of claim 56, wherein at least part of said immune response is a CD8$^+$ T cell response directed against an epitope of said Her-2 protein that is not any of said dominant CD8$^+$ T cell epitopes.

59. A method of inducing a CD8$^+$ T cell-mediated immune response in a subject against a subdominant CD8$^+$ T cell epitope of an antigen, comprising administering to said subject the recombinant form of *Listeria* of claim 7, thereby inducing a CD8$^+$ T cell-mediated immune response against a subdominant CD8$^+$ T cell epitope of an antigen.

60. A recombinant amino acid sequence consisting of the amino acid sequence of SEQ ID NO: 36.

61. A recombinant amino acid sequence consisting of the amino acid sequence of SEQ ID NO: 37.

62. A recombinant amino acid sequence consisting of the amino acid sequence of SEQ ID NO: 39.

* * * * *